US012424326B2

(12) United States Patent
Hayter et al.

(10) Patent No.: US 12,424,326 B2
(45) Date of Patent: Sep. 23, 2025

(54) SYSTEMS, DEVICES, AND METHODS FOR EPISODE DETECTION AND EVALUATION

(71) Applicant: ABBOTT DIABETES CARE INC., Alameda, CA (US)

(72) Inventors: Gary A. Hayter, Oakland, CA (US); Timothy C. Dunn, San Francisco, CA (US); Nathan Crouther, San Francisco, CA (US); Daniel M. Bernstein, El Granada, CA (US); Eric L. Davis, Castro Valley, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 515 days.

(21) Appl. No.: 17/226,636

(22) Filed: Apr. 9, 2021

(65) Prior Publication Data
US 2021/0225524 A1 Jul. 22, 2021

Related U.S. Application Data

(63) Continuation of application No. 15/573,736, filed as application No. PCT/US2016/041014 on Jul. 5, 2016, now Pat. No. 11,004,566.
(Continued)

(51) Int. Cl.
| A61B 5/00 | (2006.01) |
| A61B 5/145 | (2006.01) |
| G06F 11/362 | (2025.01) |
| G06F 30/20 | (2020.01) |
| G16H 10/40 | (2018.01) |
(Continued)

(52) U.S. Cl.
CPC .......... *G16H 50/30* (2018.01); *A61B 5/0004* (2013.01); *A61B 5/14532* (2013.01); *A61B 5/7275* (2013.01); *A61B 5/7282* (2013.01); *A61B 5/7435* (2013.01); *A61B 5/7475* (2013.01); *G06F 11/366* (2013.01); *G06F 30/20* (2020.01); *G16H 10/40* (2018.01); *G16H 10/60* (2018.01); *G16H 40/67* (2018.01); *A61B 5/4839* (2013.01)

(58) Field of Classification Search
CPC ............................ G16H 50/30; A61B 5/14532
See application file for complete search history.

(56) References Cited

U.S. PATENT DOCUMENTS

| 5,590,329 A | 12/1996 | Goodnow, II et al. |
| 5,841,969 A | 11/1998 | Fye |
(Continued)

FOREIGN PATENT DOCUMENTS

| CN | 1688244 A | 10/2005 |
| JP | 2000-271090 | 10/2000 |
(Continued)

OTHER PUBLICATIONS

JP, 2017-558396 Third Office Action, Jun. 9, 2021.
(Continued)

*Primary Examiner* — Reginald R Reyes
(74) *Attorney, Agent, or Firm* — ONE LLP

(57) ABSTRACT

Systems, devices, and methods are provided that allow detection of episodes in analyte measurement, prompting a patient to self-report possible causes for the episodes. Correlation of possible causes with detected episodes assists patient behavior modification to reduce the occurrence of episodes.

22 Claims, 36 Drawing Sheets

Related U.S. Application Data

(60) Provisional application No. 62/191,208, filed on Jul. 10, 2015, provisional application No. 62/189,137, filed on Jul. 6, 2015.

(51) Int. Cl.
*G16H 10/60* (2018.01)
*G16H 40/67* (2018.01)
*G16H 50/30* (2018.01)

(56) References Cited

U.S. PATENT DOCUMENTS

| | | | |
|---|---|---|---|
| 6,442,749 | B1 | 8/2002 | Hirao et al. |
| 6,748,555 | B1 | 6/2004 | Teegan et al. |
| 6,996,808 | B1 | 2/2006 | Niewiadomski et al. |
| 7,225,428 | B1 | 5/2007 | Fetzer et al. |
| 7,818,199 | B2 | 10/2010 | Watanabe et al. |
| 7,912,674 | B2 | 3/2011 | Killoren Clark et al. |
| 8,078,788 | B2 | 12/2011 | Chang et al. |
| 8,913,946 | B2 | 12/2014 | Katsuki |
| 9,940,444 | B1 | 4/2018 | Murphy et al. |
| 2004/0049418 | A1 | 3/2004 | Watanabe et al. |
| 2005/0022115 | A1 | 1/2005 | Baumgartner et al. |
| 2005/0076237 | A1 | 4/2005 | Cohen et al. |
| 2005/0154277 | A1 | 7/2005 | Tang et al. |
| 2007/0050780 | A1 | 3/2007 | O'Dea et al. |
| 2007/0173726 | A1 | 7/2007 | Kim et al. |
| 2008/0076969 | A1 | 3/2008 | Kraft et al. |
| 2008/0300534 | A1 | 12/2008 | Blomquist |
| 2009/0177702 | A1 | 7/2009 | Stahmann et al. |
| 2010/0305965 | A1 | 12/2010 | Benjamin et al. |
| 2011/0174638 | A1 | 7/2011 | Katsuki |
| 2011/0213225 | A1 | 9/2011 | Bernstein et al. |
| 2011/0287528 | A1 | 11/2011 | Fern et al. |
| 2013/0085358 | A1 | 4/2013 | Crouther et al. |
| 2013/0311863 | A1 | 11/2013 | Gutkin et al. |
| 2014/0088392 | A1 | 3/2014 | Bernstein et al. |
| 2014/0088393 | A1* | 3/2014 | Bernstein ............... G16H 80/00 600/365 |
| 2014/0149329 | A1* | 5/2014 | Shaw ............... G16H 50/20 706/46 |
| 2014/0187887 | A1 | 7/2014 | Dunn et al. |
| 2014/0188400 | A1 | 7/2014 | Dunn et al. |
| 2014/0273042 | A1* | 9/2014 | Saint ............... A61B 5/14532 435/14 |
| 2014/0350369 | A1 | 11/2014 | Budiman et al. |
| 2015/0143117 | A1 | 5/2015 | Freeman et al. |
| 2015/0143179 | A1 | 5/2015 | Desai et al. |
| 2015/0205930 | A1 | 7/2015 | Shaanan et al. |
| 2015/0205947 | A1 | 7/2015 | Berman et al. |
| 2015/0241407 | A1* | 8/2015 | Ou ............... G16Z 99/00 702/19 |
| 2015/0341438 | A1 | 11/2015 | Sloan et al. |
| 2016/0070636 | A1 | 3/2016 | Furtwangler et al. |

FOREIGN PATENT DOCUMENTS

| | | |
|---|---|---|
| JP | 2004-344571 | 12/2004 |
| JP | 2005-62528 | 3/2005 |
| JP | 2007-172340 | 7/2007 |
| JP | 2008-140257 | 6/2008 |
| JP | 2008-154662 | 7/2008 |
| KR | 10-2015-0025626 A | 3/2015 |
| WO | WO 00/18449 A2 | 4/2000 |
| WO | WO 2008/052374 A1 | 5/2008 |
| WO | WO 2012/067854 A2 | 5/2012 |
| WO | WO 2013/032965 A1 | 3/2013 |
| WO | WO 2014/022711 A1 | 2/2014 |
| WO | WO 2014/145049 A2 | 9/2014 |
| WO | WO 2015/040167 A1 | 3/2015 |

OTHER PUBLICATIONS

JP, 2021-166113 Office Action, Sep. 7, 2022.
EP, 16821881.6 Supplementary Search Report, Feb. 11, 2019.
CN, 201680040093.8 Office Action, Oct. 20, 2020.
JP, 2017-558396 Office Action, Aug. 12, 2020.
WO, PCT/US2016/041014 ISR and Written Opinion, Mar. 15, 2017.
"Decorator pattern" from Wikipedia, the free encyclopedia retrieved from https://en.wikipedia.org/wiki/Decorator_pattern, pp. 1-7.
"Dependency injection" from Wikipedia, the free encyclopedia retrieved from https://en.wikipedia.org/wiki/ Dependency_injection, pp. 1-12.
Comstock, J., "Glooko, Joslin to launch HypoMap, new platform for hypoglycemia" retrieved from https://www.mobihealthnews.com/33705/glooko-joslin-to-launch-hypomap-new-platform-for-hypoglycemia, 2014, pp. 1-3.
Comstock, J., "Joslin, Glooko add activity tracker data to their HypoMap diabetes management system" retrieved from https://www.mobihealthnews.com/38161/joslin-glooko-add-activity-tracker-data-to-their-hypomap-diabetes-management-system, 2014, pp. 1-4.
"Joslin and Glooko Launch HypoMap software to Identify and Improve Hypoglycemia Unawareness" retrieved from https://diatribe.org/issues/65/new-now-next/6, 2014, 1 page.
"Glooko partners with Dexcom® and Insulet® to add leading insulin pump and CGM devices to its platform", retrieved from https://www.glooko.com/press-release/glooko-partners-with-dexcom-and-insulet-to-add-leading-insulin-pump-and-cgm-devices-to-its-platform/, 2015, pp. 1-5.
Liu, L., et al., "XWRAPComposer: A Multi-Page Data Extraction Service", International Journal of Web Services Research, 2006, vol. 3, No. 2, pp. 33-60.
JP, 2017-558396 Second Office Action, Feb. 10, 2021.
CA, 2,984,912 Examiner's Report, Jun. 7, 2023.
JP, 2023-34518 Office Action, Feb. 21, 2024.
CN, 202210007127.0 Second Office Action, Apr. 3, 2024.
CN, 202210007127.0 First Office Action, Sep. 15, 2023.
AU, AU2021269314 Examination Report No. 3, Dec. 22, 2023.
CA, 2,984,912 Examiner's Report, Apr. 26, 2024.
CN, 202210007127.0 Final Office Action, Aug. 21, 2024.
EP, 16821881.6 Examination Report, Jul. 17, 2024.
JP, 2023-34518 Office Action, Aug. 7, 2024.

* cited by examiner

SYSTEMS, DEVICES, AND METHODS FOR EPISODE DETECTION AND EVALUATION

CROSS-REFERENCE TO RELATED APPLICATIONS

This application is a continuation of U.S. application Ser. No. 15/573,736, filed Nov. 13, 2017, which is a national phase entry under 35 U.S.C. § 371 of PCT Application No. PCT/US16/41014, filed Jul. 5, 2016, which claims the benefit of and priority to U.S. Provisional Application Ser. No. 62/189,137, filed on Jul. 6, 2015, and U.S. Provisional Application Ser. No. 62/191,208, filed Jul. 10, 2015, all of which are incorporated by reference herein in their entirety for all purposes.

FIELD

The subject matter described herein relates to systems, devices, and methods capable of determining or predicting the occurrence of an episode in analyte data and evaluating the circumstances relating to and potentially causing that episode.

BACKGROUND

A number of systems have been developed for the automatic monitoring of analytes, like glucose, in bodily fluid such as in blood, in interstitial fluid (ISF), dermal fluid of the dermal layer, or in other biological fluid.

These systems can provide a determination of analyte levels, or readings, over time to a health care provider (HCP), a diabetic patient, and/or a caregiver. Knowing the current analyte level and how it may change over time can be useful in determining a course of action for mitigating potentially significant variations in the analyte level, referred to as excursions. However, an understanding of what causes, symptoms, and/or treatments impact the occurrence of excursions would be beneficial in reducing their frequency and severity.

For example, a reduction in the frequency and/or severity of excursions can lessen analyte level variability, and thus is beneficial to the diabetic patient. Diabetics with relatively high analyte variability may find it difficult to treat high analyte level excursions by the administration of a medication, such as insulin, to lower their analyte level, since doing so can increase the risk of low level excursions, due to the large analyte level swings that define high variability. Conversely, treatment of low level excursions through the consumption of food or carbohydrates, to raise the diabetic's analyte level can accompany an increased risk of high level excursions resulting from the subsequent raised analyte level and high variability. The reduction of the frequency and/or severity of excursions can be an important prerequisite to a reduction in variability.

A number of metrics are available to HCPs and patients to characterize or describe the variation of analyte levels (e.g., averages, medians, percentile variations, variability metrics, risk metrics, rates of change, etc.). Analyte monitoring devices and systems are capable of generating a vast amount of data that can overwhelm and confuse users to the point that little or no insight can be gained as to the reasons driving the occurrence of excursions or high variability. Additionally, recording information that may be beneficial to understanding causation can be burdensome, since it is unclear to the patient what information should be recorded.

One of the primary challenges in the investigation of causes of excursions and variability is the disassociation between the analyte level monitoring mechanism, responsible for gathering the data that is the foundation of the analysis, and the relevant conditions leading up to the occurrence of the excursions or in those times contributing most heavily to variability. Investigation into those activities is typically performed by a question and answer session between the diabetic and the HCP, which may occur days or weeks after the fact. Such sessions are disadvantageous because the diabetics often cannot remember the actions and conditions leading up to the excursion, or those actions and conditions are unknown because the diabetic was not aware of the need to track those conditions, e.g., by investigating the dose of recent administrations of medication, the carbohydrate content of recently consumed foods, the duration of recent exercise, activity, or sleep, and the like. Further, when questioned directly by an HCP, diabetics can feel obligated to supply answers that make the diabetic appear to be leading a healthier lifestyle than may, in fact, be true.

For these and other reasons, needs for improved variability and excursion monitoring, investigation, and evaluation exist.

SUMMARY

Provided herein are a number of example embodiments directed to systems, devices, and methods for investigating the reasons that cause the occurrence of analyte excursions and/or relatively high analyte variability. For example, to assist in the reduction of analyte variability, these embodiments can identify and/or investigate the occurrence of analyte episodes that contribute to excessive variability. In many embodiments, these episodes can include the occurrence of an actual analyte excursion beyond clinically safe levels, but can include other variations that may not typically qualify as an excursion.

For example, certain embodiments can provide for the monitoring of a diabetic's analyte levels, determining whether one or more analyte-related episodes have occurred (or predicting their future occurrence) based on the monitored analyte levels, prompting the diabetic for information about the episode in an improved fashion, and investigating (or enabling the investigation) of actions and other conditions that may contribute to the episode. Many of these embodiments can utilize an in vivo sensor control device that receives measurements of analyte levels from a sensor in the diabetic's body, a reader device that receives the measurement data from the sensor control device, and a monitoring application that resides on the reader device and analyzes the measurement data.

Episode investigative software (EIS) can be provided on the reader device, e.g., as a smartphone app, and/or on one or more other computing devices, for example, via a web server, that facilitates the collection of information from the diabetic user and performs or enables the subsequent investigation into the underlying root causes and conditions of episodes and variability.

Also described herein are example embodiments for operating software on a computing device with one or more wrappers. The computing device can be a reader device or other device. The wrappers can allow for the modification of data passing through interfaces between various software modules or functions.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 11-15 are diagrams depicting example embodiments of graphical user interface screens that can be displayed on the display of a reader device or other computing device executing or accessing an example embodiment of the episode investigative software.

DETAILED DESCRIPTION

Figure 1A:
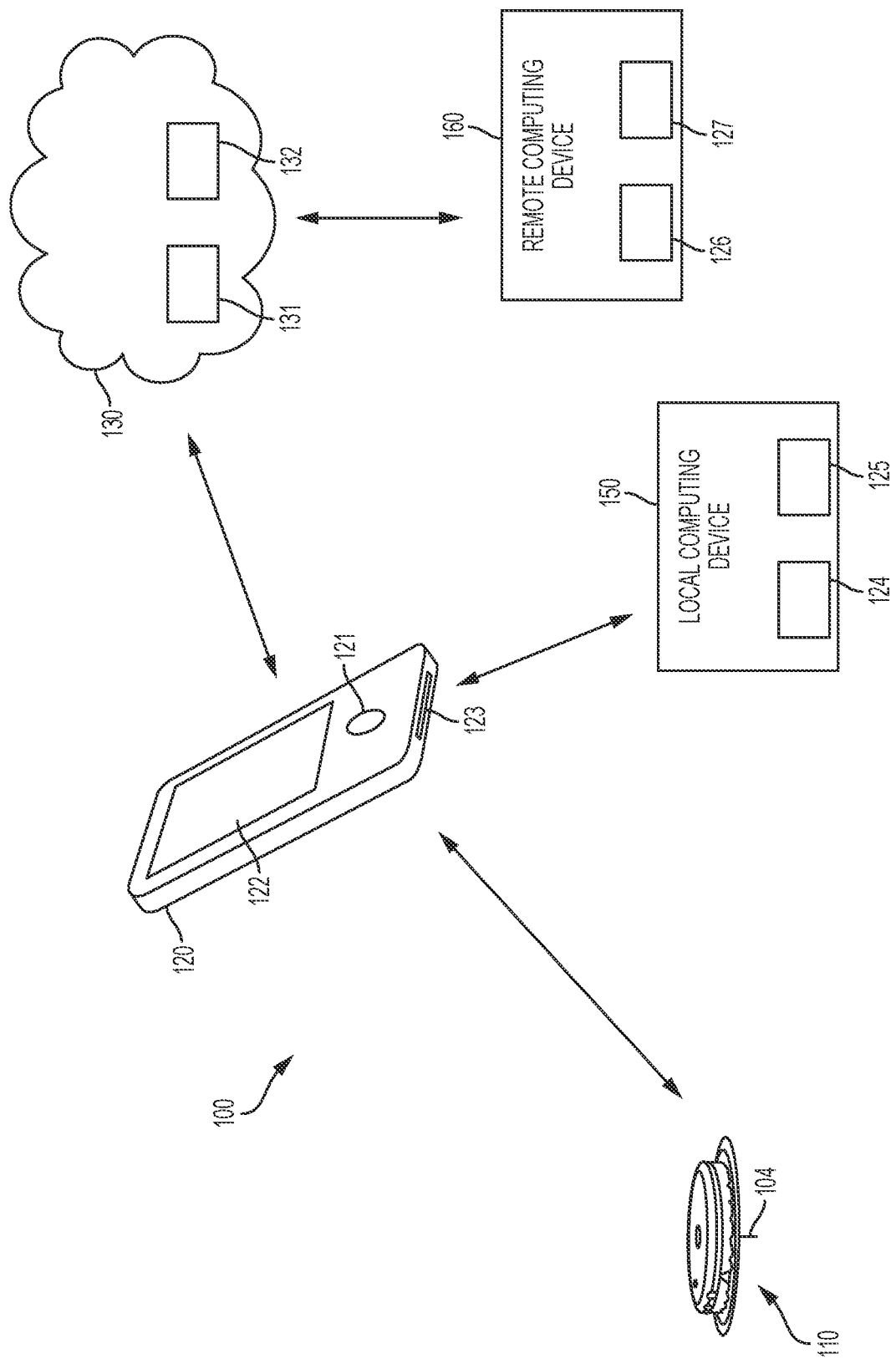
FIG. 1A is a high level diagram depicting an example embodiment of an analyte monitoring system for real-time analyte (e.g., glucose) measurement, data acquisition and/or processing using a monitoring application on a reader device.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Example Embodiments of Analyte Monitoring Systems

As mentioned, a number of systems have been developed for the automatic monitoring of the analyte(s), including but not limited to glucose, in bodily fluid such as in blood, in interstitial fluid (ISF), dermal fluid of the dermal layer, or in other biological fluid. Some of these systems are configured so that at least a portion of a sensor is positioned in a patient, e.g., in a blood vessel or in the subcutaneous tissue or dermal layer of a patient, to obtain information about at least one analyte of the body. As such, these systems can be referred to as "in vivo" analyte monitoring systems.

In vivo analyte monitoring systems include "Continuous Analyte Monitoring" systems (or "Continuous Glucose Monitoring" systems) that can transfer data by broadcast of the data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with a Radio Frequency Identification (RFID), Near Field Communication (NFC) or other protocol. An in vivo analyte monitoring system has been developed that also can operate without the need for finger stick calibration.

In vivo analyte monitoring systems can be differentiated from "in vitro" systems that contact a biological sample outside of the body (or rather "ex vivo") and that typically include a meter device that has a port for receiving an analyte test strip carrying bodily fluid of the patient, which can be analyzed to determine the patient's blood sugar level. While in many of the present embodiments the monitoring is accomplished in vivo, the embodiments disclosed herein can be used with in vivo analyte monitoring systems that incorporate ex vitro capability, as well has purely in vitro or ex vivo analyte monitoring systems.

The sensor can be part of the sensor control device that resides on the body of the patient and contains the electronics and power supply that enable and control the analyte sensing. The sensor control device, and variations thereof, also can be referred to as a "sensor control unit," a "sensor electronics" device or unit, an "on-body electronics" device or unit, an "on-body" device or unit, or a "sensor data communication" device or unit, to name a few.

In vivo monitoring systems also can include a device that receives sensed analyte data from the sensor control device and processes and/or displays that sensed analyte data, in any number of forms, to the user. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in vivo and in vitro monitoring systems.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

Many of the example embodiments described herein make reference to the monitoring of glucose; however, such references recognize only that glucose is a commonly monitored analyte and those references should not be interpreted as excluding operation with analytes other than glucose.

An in vivo system manufacturer can provide patients with both the sensor control device and the corresponding reader device; in some cases, the two can be sold as a set. The sensor control device can have a limited lifespan and can be replaced periodically (e.g., every two weeks), but the reader device can be used for a significantly longer period of time and may be reusable with each new replacement sensor control device.

One embodiment of an analyte monitoring system 100 is shown in FIG. 1A. The system can include one or more of a measuring device, such as a sensor control device 110 with an analyte sensor 104, and a reader device 120, such as a handheld smartphone running a software application, such as a glucose monitoring application 140. One or more instances of the episode investigative software (EIS) can be stored and executed within system 100.

The EIS can be stored and executed on a network server 130 (e.g., in the cloud) that is accessible by any computing device having an internet connection and an internet browser, such as reader device 120, local computing device 150, and/or remotely located computing device 160. Here, a device is local if it is accessible in the same vicinity (e.g., the same office, home, or building) as reader device 120, and a device is remote if it is located in a different vicinity (e.g., the office of the patient's HCP, etc.) than reader device 120. Alternatively, the EIS can be locally stored on and executed on reader device 120, local computing device 150, and/or remote computing device 160. Examples of local and remote computing devices can include a personal computer (PC), laptop computer, tablet computer, personal digital assistant (PDA), workstation, wearable smart device (GOOGLE GLASS, APPLE WATCH), and others.

Each device that can store and/or execute software includes non-transitory memory for storing the software and processing circuitry communicatively coupled with the non-transitory memory for executing the software. These devices also include the appropriate communications interface for communication with other devices (e.g., a network communications port, etc.). For example, server 130 includes processing circuitry 131 communicatively coupled with non-transitory memory 132, local computing device 150 includes processing circuitry 124 communicatively coupled with non-transitory memory 125, and remote computing device 160 includes processing circuitry 126 communicatively coupled with non-transitory memory 127. Because the EIS can be stored and executed on a number of combinations of devices, server 130, local computing device 150, and remote computing device can each be omitted.

As shown in FIG. 1A, the components can be in wireless communication with each other using a wireless communication protocol such as, for example, NFC, RFID, Wi-Fi, Bluetooth, Bluetooth Low Energy, or proprietary protocols. Each of the components can also be in direct communication through a wired link (e.g., USB) or indirectly through a distributed wired network (e.g., TCP/IP).

Data obtained from sensor control device 110 and patient-supplied data (described below) is stored in a location accessible to the EIS, e.g., in reader device 120, network server 130, local computing device 150, and/or remote computing device 160. The data can be uploaded from reader device 120. The stored data can be processed and/or analyzed by the EIS to assist diabetics, patients, interested people (e.g., parents, guardians, caretakers), health care professionals (HCPs) or any users in identifying patterns and reasons that may cause episodes, which in turn can lead to improved analyte control.

The EIS can correlate diabetic actions, lifestyle, and/or behavior with glucose levels, thereby reducing the burden on the user to sort out the effects. The EIS can use clinically-informed algorithms to search glucose data acquired for an individual patient and the patient's recorded behaviors (or a plurality of patients and patients' records) to reveal patterns that affect glucose levels. In some embodiments, the EIS can include instructions that: 1) define episodes of interest, 2) select a kernel episode for the search routine, 3) construct an episode in close proximity to the kernel, 4) associate one or more episodes with a diabetes self-care behavior, and 5) cause the display of the findings of the search algorithms. In other embodiments, the EIS can include instructions that: 1) define episodes of interest, 2) select a kernel episode for the search routine, 3) construct an episode chain, which is a sequence of episodes (including the kernel episode) and logical rules for the inclusion or exclusion of episodes in close proximity to the kernel, 4) associate one or more episode chains with a diabetes self-care behavior, and 5) cause the display of the findings of the search algorithms.

Additional examples of episode investigative systems, software, and algorithms that are usable with, or in place of, the EIS systems, software, and algorithms described herein, are set forth in U.S. Patent Application Publication No. 2014/0350369, U.S. Patent Application Publication No. 2014/0088392, and U.S. Patent Application Publication 2014/0088393, all of which are incorporated herein by reference in their entirety and for all purposes.

Referring back to FIG. 1A, sensor control device 110 is configured to receive glucose level readings from an in vivo positionable sensor 104, e.g., a subcutaneous sensor, dermal sensor, blood vessel sensor, and the like. In other embodiments, the sensor can be positioned ex vivo but can monitor the analyte level in vivo, such as certain optical sensors. Sensor control device 110 causes sensor 104 to repeatedly sense glucose levels, either according to a predetermined schedule or on an ad hoc basis, and reads one or more signals representative of the glucose level from sensor 104. These glucose level readings may be stored in sensor control device 110 and transferred to reader device 120 in batches at predetermined times, on-demand, or immediately after a glucose level reading is obtained.

Non-limiting examples of reader devices can include the meter device of an ex-vivo monitoring system, the reader device of an in-vivo monitoring system, combinations of the two such as an in vivo reader operating with a test strip port and meter functionality, and various other devices such as smartphones, tablets, proprietary readers, other computing devices, etc. Reader device 120 can include one or more software applications that perform various program routines, such as communicating with another device executing the EIS, displaying data in various fashions, receiving input from the user (e.g., HCP, caregiver, and/or diabetic patient) to help the diabetic manage their diabetes, and detecting episodes. Reader device 120 can include buttons, such as a keyboard, for example, used for entering information. In addition, or alternatively, reader device 120 can include virtual buttons, such as a touch screen configured to present a virtual keyboard.

Reader device 120 can also include or be integrated with a drug (e.g., insulin, etc.) delivery device such that they, e.g., share a common housing. The drug delivery hardware can include a reservoir to store the drug and a pump that can be connectable to transfer tubing and an infusion cannula for administering the drug from the reservoir, through the tubing and into the diabetic's body by way of the cannula inserted therein.

Figure 1B:
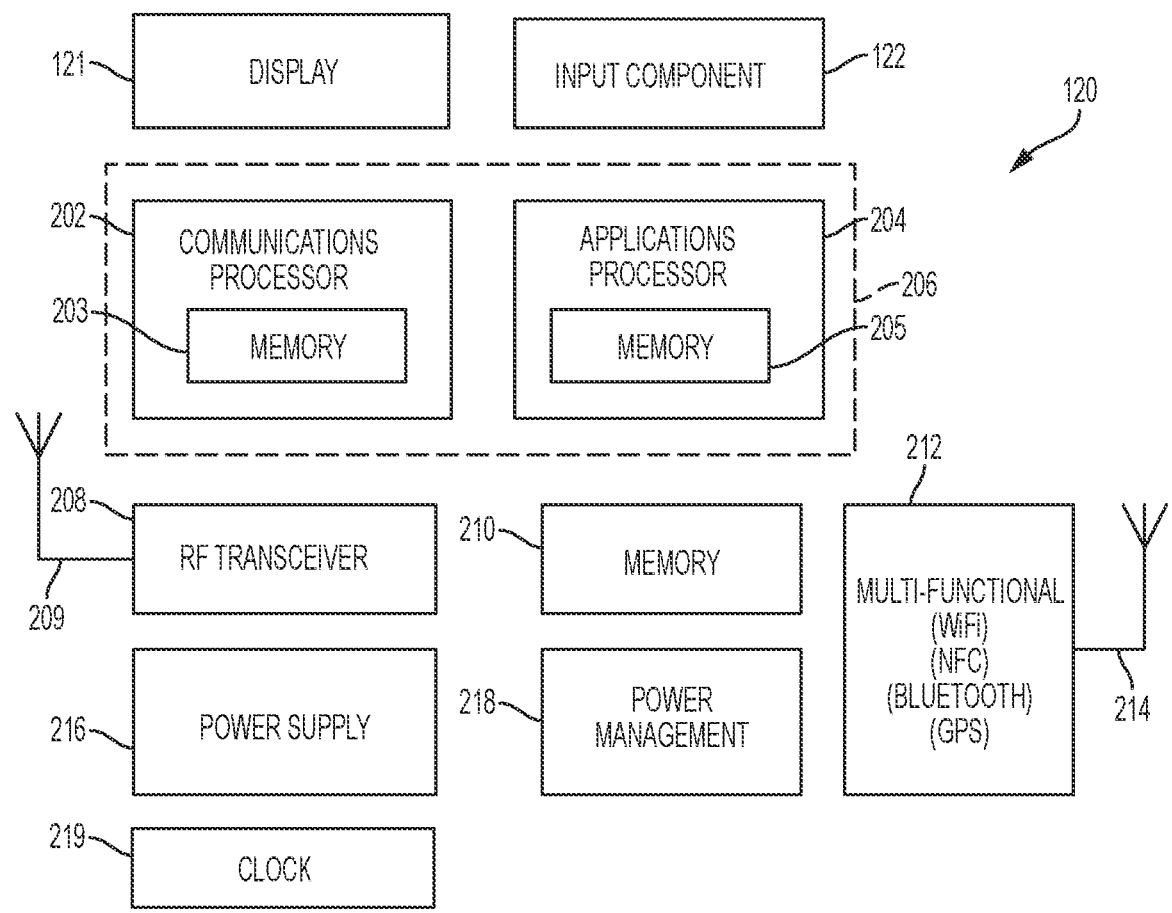
FIG. 1B is a block schematic depicting an example embodiment of a reader device.

FIG. 1B is a block diagram of an example embodiment of a reader device 120 in the form of a smartphone. Here, reader device 120 includes an input component 122, display 121, and processing circuitry (or hardware) 206, which can include one or more processors, microprocessors, controllers, and/or microcontrollers, each of which can be a discrete chip or distributed amongst (and a portion of) a number of different chips. Processing hardware 206 can include a communications processor 202 having on-board memory 203 and an applications processor 204 having on-board memory 205. Additional processors can and will likely be present. Reader device 120 further includes an RF transceiver 208 coupled with an RF antenna 209, a memory 210, multi-functional circuitry 212 with one or more associated antennas 214, a power supply 216, and power management circuitry 218. FIG. 1B is an abbreviated representation of the internal components of a smartphone, and other hardware and functionality (e.g., codecs, drivers, glue logic, etc.) can of course be included.

Communications processor 202 can interface with RF transceiver 208 and perform analog-to-digital conversions, encoding and decoding, digital signal processing and other functions that facilitate the conversion of voice, video, and data signals into a format (e.g., in-phase and quadrature) suitable for provision to RF transceiver 208, which can then transmit the signals wirelessly. Communications processor 202 can also interface with RF transceiver 208 to perform the reverse functions necessary to receive a wireless transmission and convert it into digital data, voice, and video.

Applications processor 204 can be adapted to execute the operating system and any software applications that reside on reader device 120, process video and graphics, and perform those other functions not related to the processing of communications transmitted and received over RF antenna 209. Any number of applications can be running on reader device 120 at any one time, and will typically include one or more applications that are related to a diabetes monitoring regime, in addition to the other commonly used applications that are unrelated to such a regime, e.g., email, calendar, weather, etc.

Memory 210 can be shared by one or more the various functional units present within reader device 120, or can be distributed amongst two or more of them (e.g., as separate memories present within different chips). Memory 210 can also be a separate chip of its own. Memory 210 is non-transitory, and can be volatile (e.g., RAM, etc.) and/or non-volatile memory (e.g., ROM, flash memory, F-RAM, etc.).

Multi-functional circuitry 212 can be implemented as one or more chips and/or components, including communication circuitry, that perform other functions such as local wireless communications (e.g., Wi-Fi, Bluetooth, Bluetooth Low Energy) and determining the geographic position of reader device 120 (e.g., global positioning system (GPS) hardware). One or more other antennas 214 are associated with both the functional circuitry 212 as needed.

Power supply 216 can include one or more batteries, which can be rechargeable or single-use disposable batteries. Power management circuitry 218 can regulate battery charging and power supply monitoring, boost power, perform DC conversions, and the like. As mentioned, reader device 120 may also include one or more data communication ports such as USB port (or connector) or RS-232 port (or any other wired communication ports) for data communication with a remote terminal 170, or sensor control device 110, to name a few. A network syncing clock 219 is also present that can provide the system time and include, for example, an RC or crystal oscillator and associated clock buffers and distribution circuitry.

Figure 1C:
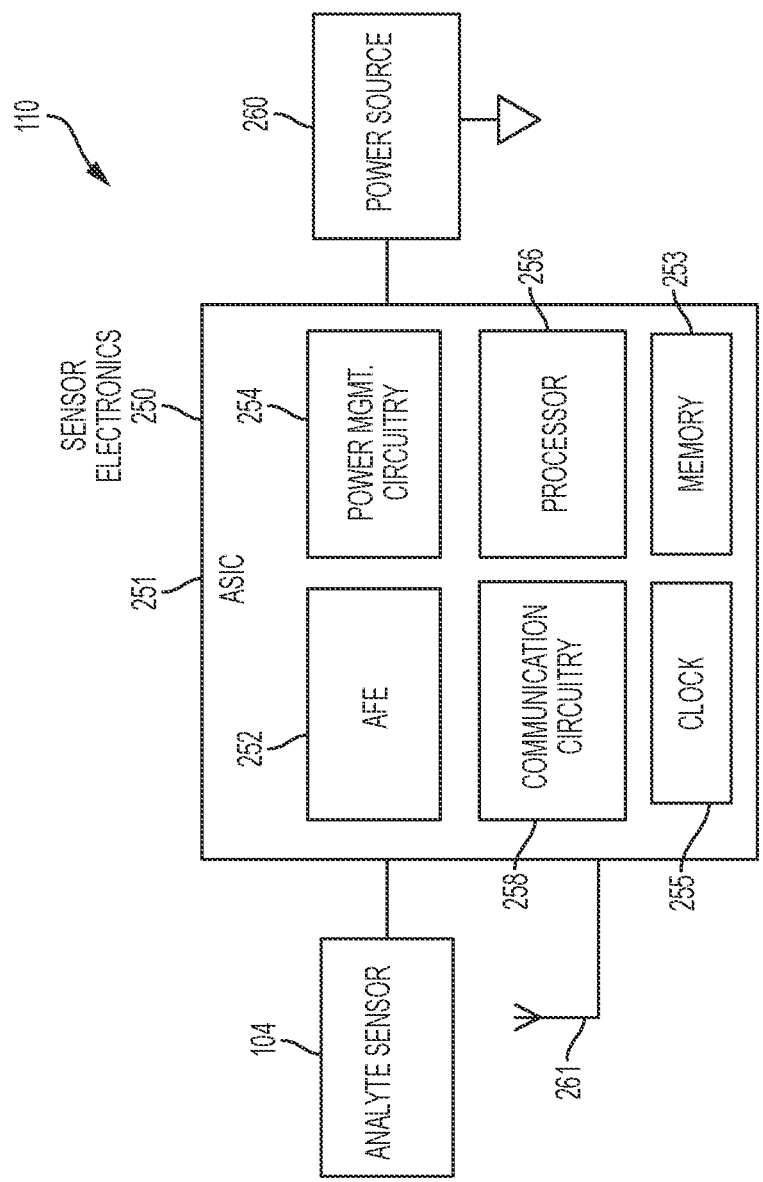
FIG. 1C is a block schematic depicting an example embodiment of a sensor control device.

FIG. 1C is a block schematic diagram depicting an example embodiment of sensor control device 110 having analyte sensor 104 and sensor electronics 250 (including analyte monitoring circuitry). Although any number of chips can be used, here the majority of the sensor electronics 250 are incorporated on a single semiconductor chip 251 that can be, e.g., a custom application specific integrated circuit (ASIC). Shown within ASIC 201 are several high-level functional units, including an analog front end (AFE) 252, power management circuitry 254, processor 256, and communication circuitry 258 (which can be implemented as a transmitter, receiver, transceiver, passive circuit, or otherwise according to the communication protocol). In this embodiment, both AFE 252 and processor 256 are used as analyte monitoring circuitry, but in other embodiments either circuit can perform the analyte monitoring function. Processor 256 can include one or more processors, microprocessors, controllers, and/or microcontrollers.

A non-transitory memory 253 is also included within ASIC 251 and can be shared by the various functional units present within ASIC 251, or can be distributed amongst two or more of them. Memory 253 can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn processes the data to arrive at the end-result analyte discrete and trend values, etc. This data can then be provided to communication circuitry 258 for sending, by way of antenna 261, to reader device 120 (not shown) where further processing can be performed by, e.g., the sensor interface application.

A clock 255 is also present that can be, for example, an RC or crystal oscillator. Clock 255 can be a monotonic clock that moves forward at constant rate (subject to environmental drift) and continues for the entire life of the sensor without interruption. In some embodiments, sensor control device 110 can keep time by generating an interrupt after a predetermined number of seconds (e.g., every second, or every minute etc.), where the interrupt increments a software or hardware counter. The counter value reflects the number of predetermined time spans that have passed since the sensor was activated. For example, if the interrupt is generated every minute, then the counter value reflects the number of minutes that have passed since activation of sensor control device 110. The functional components of ASIC 251 can also be distributed amongst two or more discrete semiconductor chips.

U.S. Patent Application Publ. No. 2011/0213225 (the '225 Publication) describes variants of sensor control device 110 and reader device 120, as well as other components of an in vivo-based analyte monitoring system, all of which are suitable for use with the system, device, and method embodiments set forth herein. As such, the '225 Publication is incorporated by reference herein in its entirety for all purposes.

Example Embodiments with Episode Investigative Software (EIS)

The EIS can be utilized to detect prior, current, and/or future episodes. The term episode, as used herein, does not refer to every variation of an analyte level but rather those variations that significantly contribute to the subject's analyte variability, such as high glucose and low glucose peaks. Episodes can also include glucose excursions or events that are clinically significant, such as a rapid rise or rapid fall in the glucose level. Different conditions can be used to qualify a set of analyte level measurements as an episode, including the analyte measurement's magnitude, the rate of change between sequential analyte measurements or other groups of measurements that are close in time, the number of analyte measurements (or duration of time) in which a threshold magnitude is violated, the violation of a threshold by the area of an integral of a sequence of analyte measurements, any combination thereof, and others. Such episodic detection conditions are described in U.S. Publ. No. 2013/0085358, which is incorporated by reference herein in its entirety and for all purposes.

As previously stated, the EIS can be executed on a number of different devices, including mobile devices with sensor interface capability (e.g., reader device 120) or mobile devices without a sensor interface capability (e.g., a typical tablet or mobile phone).

Alternatively, the EIS can be executed partially on the electronics co-located with sensor 104, communicating data that confirms the occurrence of each episode to a user interface (UI)-capable device such as a mobile device, personal computer (PC), and the like. In such embodiments sensor control device 110 performs a substantial amount of algorithmic processing on the collected measurement data to determine if predetermined conditions for the occurrence of an episode are met by the measurement data. The sensor control device 110 can then transmit the confirmation that an episode has occurred (and any desired information about that episode such as type, time, location, etc.) and optionally the underlying measurement data as well.

The EIS can be stored in the non-transitory memory of the device (e.g., 120, 130, 150, 160) executing the software (e.g., as a plurality of instructions). The EIS can be executed by the processing circuitry of the device. To the extent user input is provided (e.g., the entry of text, a mouse click, a touch selection, etc.), it is done so by way of a user interface, e.g., a touchscreen or user input 121 of reader device 120, and the user input is received and read (or interpreted) by the processing circuitry, which then causes the appropriate action to be taken (e.g., causing a new screen to be displayed, causing a check mark to be displayed, modifying a pick list, etc.).

Reader device 120 in the embodiment of FIG. 1A can be a smartphone running one or more downloadable software applications, commonly referred to as "apps." The EIS can be configured and distributed as such a downloadable app. The EIS can also be resident software installed directly on reader device 120 at time of manufacture (prior to distribution or sale). The EIS can include the software instructions for interfacing with sensor control device 110 and processing data received from sensor control device 110 into a user-readable value representative of the user's glucose level (for example, applying algorithms to and otherwise processing raw sensor data to determine an actual analyte level that can be displayed to and interpreted by the diabetic or other user). Alternatively, the EIS can operate with a separate software application responsible for communicating with sensor control device 110 and receiving and processing the raw data, such as a glucose monitoring application. That glucose monitoring application can similarly be configured and distributed as a downloadable app, or as factory-installed resident software.

Example Embodiments of Mobile Devices with Episode Investigative Software (EIS)

Although not limited to such, for ease of description, with respect to reader device 120, the EIS will be described as a downloadable app having the glucose monitoring instructions incorporated therein.

Reader device 120 can receive glucose level readings automatically or can request glucose level readings from sensor control device 110 and can make them available to the EIS or otherwise transmit the readings to the device executing the EIS. Reader device 120 can process the readings and send alerts and/or prompts to the patient based on episodes identified by the EIS. Reader device 120 can display one or more of rates of analyte change, reports, tables, graphs, and other representations of processed glucose level readings and inputted behaviors (meals, insulin, etc.) generated by the software on reader device 120 or from the EIS for use by the HCP and patient.

Reader device 120 can receive glucose measurements directly or indirectly (in the case of a primary/secondary receiver system) from sensor control device 110. Additionally or alternatively, in some embodiments, in particular, those that include an ex vivo or non-sensor measuring device, the glucose measurement can be derived from a bodily fluid sample on a test strip, or even manually input into reader device 120 by the patient, e.g., a blood glucose reading. Glucose measurements, whether manually input or obtained from sensor control device 110, can be transferred to the EIS.

Sensor control device 110 can be used in a continuous mode, with glucose level readings being repeatedly collected and sent by sensor control device 110 to reader device 120 automatically (i.e., broadcast) every few seconds, every few minutes, for example every 1, 5, 10, 15 minutes, or the like. Alternatively, sensor control device 110 can include sufficient storage memory, for example, sufficient to hold 8 hours of data, to hold multiple automatically gathered glucose level measurements until transferred to reader device 120. The patient can obtain glucose level measurements manually, or "on-demand," with reader device 120 by a patient-initiated request for data (e.g., an NFC scan) from sensor control device 110. This can include all glucose readings that are stored in memory in sensor control device 110, or a subset, such as those that have not already been transferred to reader device 120, or those that have been collected in a recent period of time, or a predetermined number of recent measurements (e.g., two or three, etc.).

In one embodiment, the EIS can be configured as a "masked" version or an "unmasked" version. The masked version can be used for a period of time to establish a baseline, for example, a multi-day period such as 3 days, one week, two weeks, and others. The masked version can allow the patient limited access to glucose readings and other information or features of the application. The patient can obtain glucose data from sensor control device 110 to record glucose levels for later assessment by the HCP, however, access to that glucose information is restricted. For example, in some embodiments, the patient is not shown any glucose level reading during the masked period of time, but is allowed to see the nature or type of various episodes (e.g., high glucose episode, low glucose episode, etc.). In other embodiments, the patient is not shown any glucose reading nor is the patient shown any information about the nature or type of episode during the masked period of time. For example, the patient may be informed only that "an episode has occurred" without any further information about the episode.

The masked version encourages the patient to follow normal eating, exercising, and medicating behaviors free of any influence that knowledge of glucose levels or episode types may cause. Receipt of data from sensor control device 110 at frequent intervals, for example, at least once every eight hours or other length of time, is performed to obtain multiple glucose level readings. The EIS can prompt the patient to scan sensor control device 110 if necessary, or alternatively, a reminder application can be used.

The unmasked version of the EIS allows patient access to more, sometimes to all, features. In certain embodiments, masked and unmasked versions of the application do not exist concurrently on reader device 120. In other embodiments, masked and unmasked versions can exist concurrently on reader device 120. In yet other embodiments, the two versions can exist within one application and a software switch accessible by the HCP can be used to switch between one version and the other.

As discussed, the EIS can be installed on reader device 120 in any manner. The glucose monitoring application can be installed on smartphones running various operating systems, for example, ANDROID, iOS, or others. Installation can be accomplished using standard installation methods. For example, installation on an ANDROID-based smartphone can be done by e-mailing an apk file to reader device 120 and executing the file.

After installation of the EIS (if necessary), the patient and reader device 120 can be registered on server 130 and associated with one another. The patient may be given a temporary username or a permanent username may be assigned. The username should be unique, and if a temporary username is provided, when the patient requests a permanent username, it should be vetted to ensure uniqueness. The username may be an e-mail address or other unique set of alphanumeric symbols. Reader device 120 may be identified by any unique set of identifiers associated with reader device 120, for example, an IMEI number or a MAC address.

Figure 2:
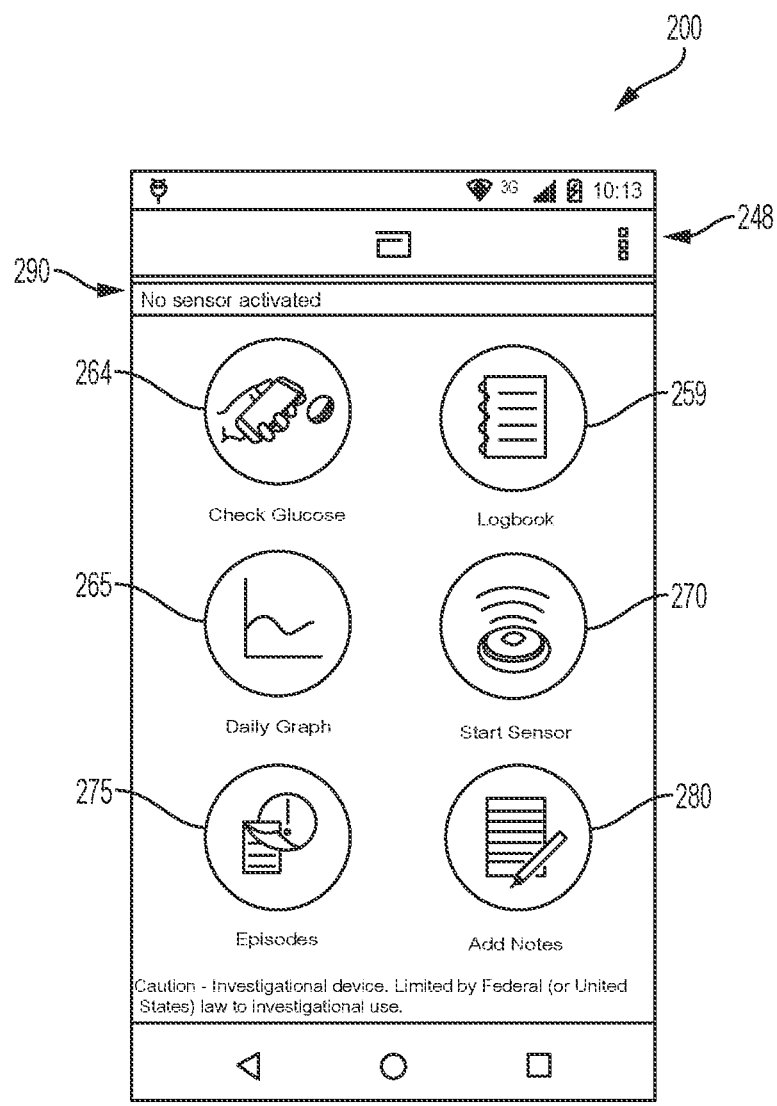
FIGS. 2-9C are diagrams depicting example embodiments of graphical user interface screens that can be displayed on the display of a reader device or other computing device executing or accessing an example embodiment of the episode investigative software.

FIG. 2 depicts an example embodiment of a graphical user interface (GUI) display screen 200 that can be displayed to the user upon activation of the EIS on display 122 of reader device 120, which in this embodiment is a touch screen. Here, display screen 200 is a home page 200 that can include multiple user selectable fields. These fields are selectable upon a touch by the user (or a click with a mouse cursor, etc., in other embodiments). For ease of reference these fields will be referred to herein as buttons.

Home page 200 can include one or more of a menu button 248, a check glucose button 264, a logbook button 259, a daily graph button 265, a start sensor button 270, an episodes button 275, an add notes button 280, and a sensor status area 290. Sensor status area 290 indicates whether sensor 104 has been activated, has expired, or the length of time remaining before expiration. Example functions of each home page button are described below.

Figure 3B:
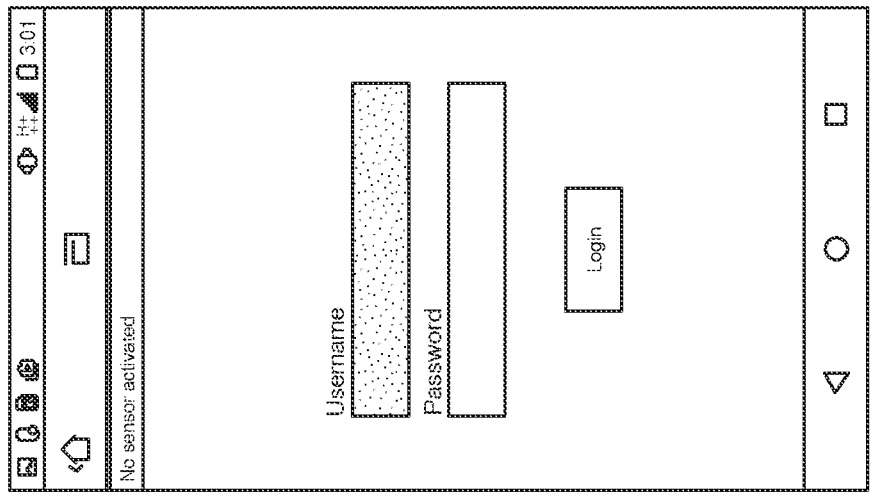
Figure 3A:
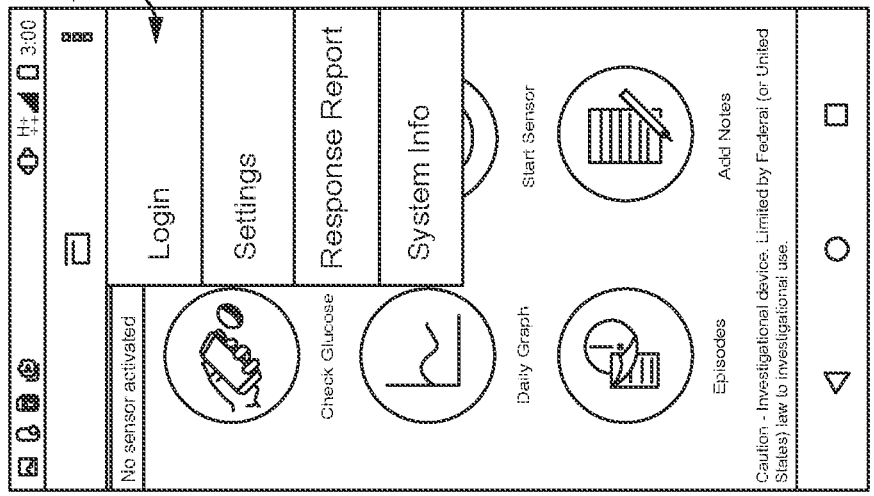

To log into server 130, the menu button 248 is clicked and the Login field 249 is selected, as shown in the example embodiment of FIG. 3A, which causes the display of login screen 262, shown in the example embodiment of FIG. 3B. The user can then enter their username and password to log into server 130. In some embodiments, the user is first logged in before the EIS will automatically upload data to server 130. After logging in, pressing menu button 248 results in different menu choices being presented, as will be described below.

Referring back to FIG. 2, start sensor button 270 can be used to activate sensor 104 after sensor control device 110 is applied to the patient. When sensor 104 is changed, e.g., after about 14 days, the activation step is repeated. In one embodiment, where reader device 120 communicates with sensor control device 110 over an NFC link, reader device 120 can be held within a close proximity communication range, for example, approximately 3 inches or less, of sensor control device 110. Reader device 120 can be repositioned around sensor control device 110, if needed until communication is established, signified by reader device 120 generating a sound and/or vibration or other connection indicator. Once the sound or vibration occurs, reader device 120 can be held in place for an amount of time, for example, about 1-2 seconds, until another sound and/or vibration occurs indicating that sensor 104 (or sensor control device 110) has been activated. In some embodiments, glucose level measurements will not be made or reported to reader device 120 until the expiration of a predetermined amount of time after activation that allows the proper initialization of sensor 104. In some embodiments, this "warm-up period" is 60 minutes, although the length of time can depend on the sensor itself and may be longer or shorter, or may not be required at all.

Still referring to FIG. 2, after sensor 104 is activated, glucose levels can be checked using the EIS. When check glucose button 264 is selected, reader device 120 obtains one or more glucose measurements from sensor control device 110 using one of the communication methods described herein, such as an on-demand method. Additionally, the readings can be sent automatically from reader device 120 to server 130.

Figure 4A:
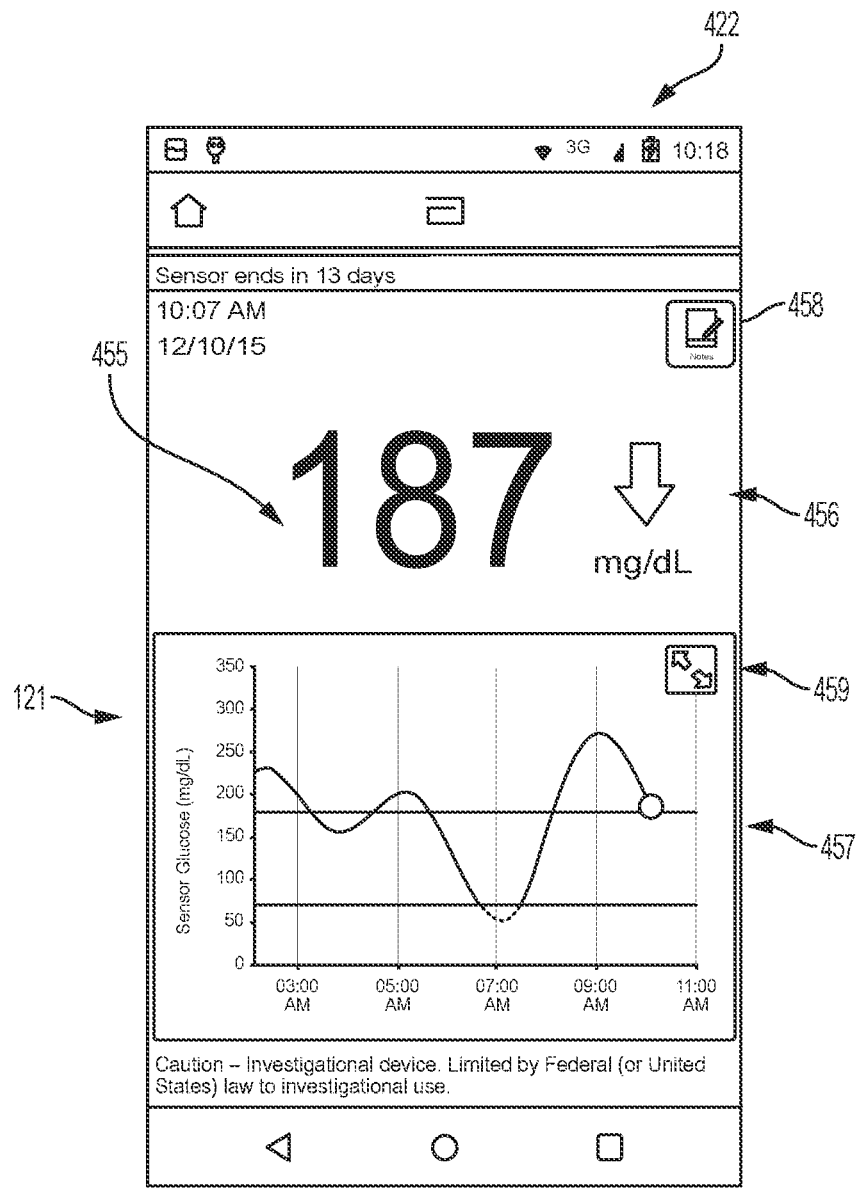

After the glucose level readings are transferred, screen 121 of reader device 120 can automatically display a result screen 422 as shown in the example embodiment of FIG. 4A. Result screen 422 can include one or more of a display of the current glucose level reading 455, a trending arrow 456 showing the direction and/or rate in which glucose level readings are changing, and a glucose graph 457. A notes button 458 also can be presented on the result screen 422. If the result is more than a predetermined amount of time, e.g., 3 minutes old in some instances, a warning message can appear indicating that the results are not current.

Glucose reading 455 can be the current glucose level reading up to a predetermined level, e.g., 350 mg/dl. Readings greater than the predetermined level may be sticky, in that they may be displayed as the predetermined level. Trending arrow 456 can be one of a plurality of indicators, e.g., five different, relative arrows. In certain embodiments, an arrow pointing up can indicate glucose level readings are quickly rising at a rate greater than a predetermined high rate, e.g., 2 mg/dl per minute. An arrow pointing up and to the right can indicate glucose level readings are rising at a predetermined moderate rate, e.g., between 1 and 2 mg/dl per minute. If glucose level readings are changing upwardly or downwardly at a predetermined low rate, e.g., less than 1 mg/dl per minute, the arrow can point to the right. An arrow pointing down and to the right can indicate glucose level readings are falling at a predetermined moderate rate, e.g., between 1 and 2 mg/dl per minute, and an arrow pointing down can indicate glucose level readings are quickly falling at a predetermined rate, e.g., more than 2 mg/dl per minute.

Glucose graph 457 can display measured glucose level readings over a predetermined time range, for example, over the past 8 hours, and the time range can be increased or decreased using the zoom button 459 or by using standard 2-finger zoom techniques of reader device 120. The time range can be shifted by dragging the plot left or right with a finger. A symbol, for example, a clock symbol, can appear in the graph to indicate that the reader device's time was changed. A change in time can result in gaps in the graph, overlapping readings, or hidden data that the HCP, patient, and/or caregiver should be made aware of.

Figure 4B:
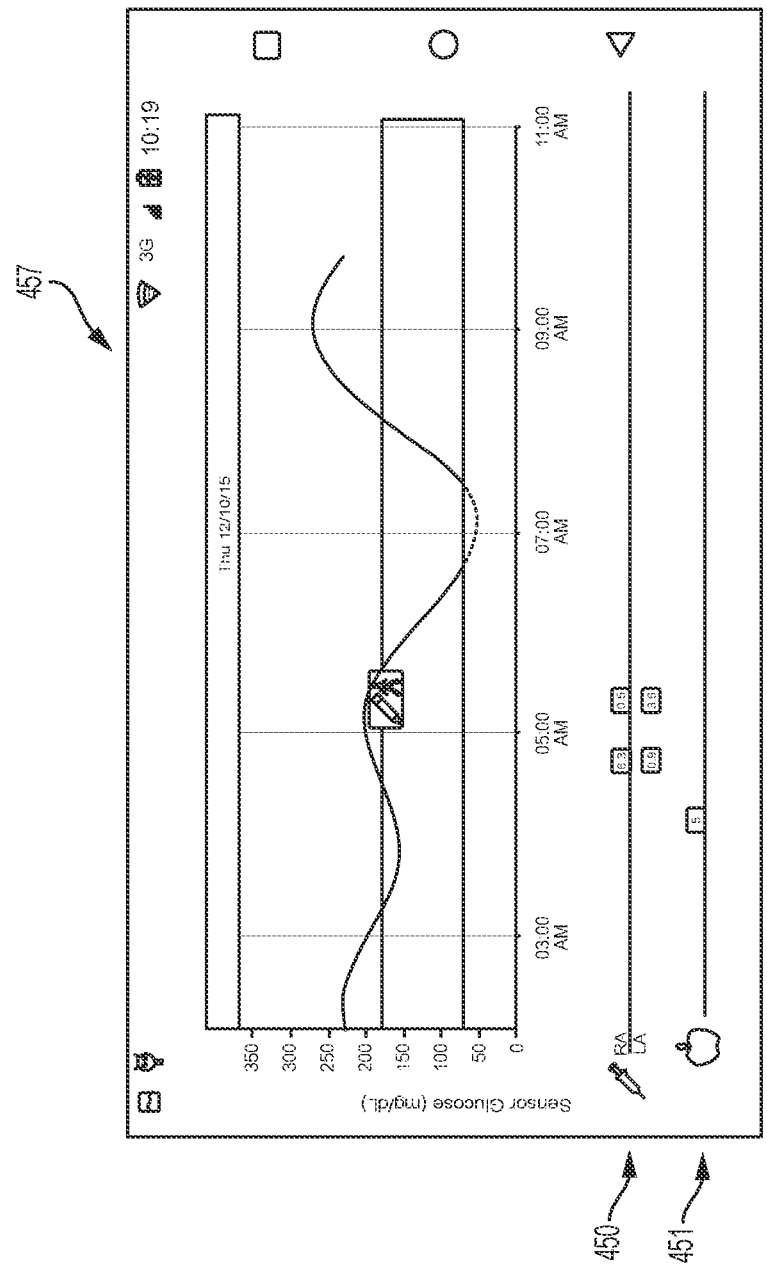
Figure 5:
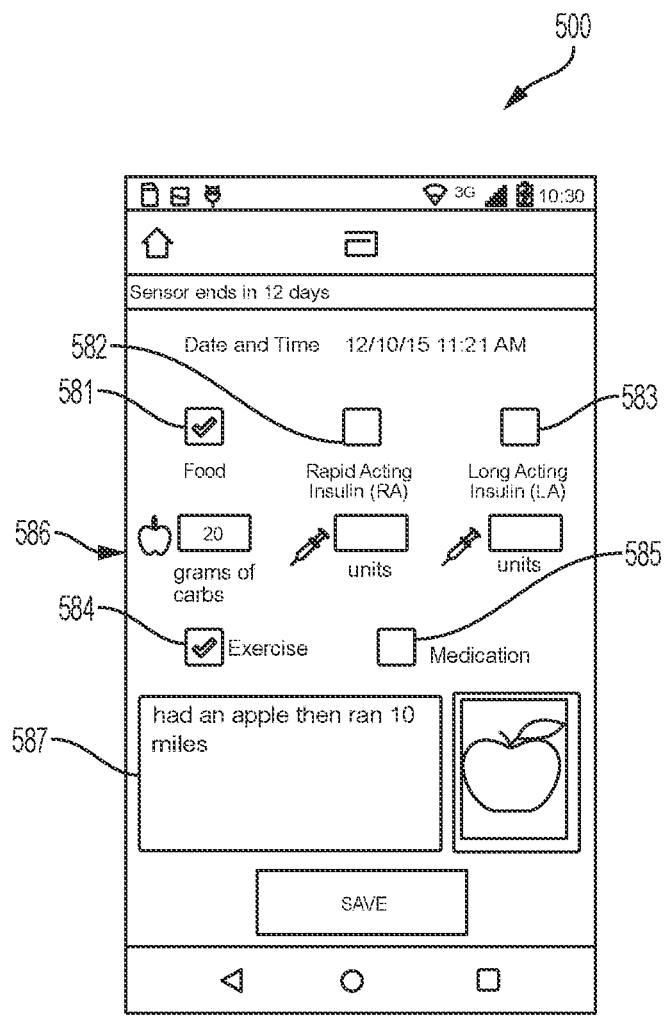

FIG. 4B depicts an example embodiment of glucose graph 457 after depressing zoom button 459. Beneath graph 457 is an medication timeline 450 indicating times and amounts of rapid acting insulin (top) and long acting insulin (bottom) that were administered over the displayed time period, with numerical indicators conveying the respective dose amount and aligned appropriately to convey the associated time of dose administration. Beneath timeline 450 is a meal timeline 451 indicating times and amounts of meals or food that was consumed over the displayed time period, with a numerical indicator conveying the consumed carbohydrate amount and aligned appropriately to convey the associated time of consumption Notes can be used to track behavior such as one or more of food intake, insulin, medication, exercise, sleep, and the like. FIG. 5 depicts an example embodiment of notes entry page 500. Notes can be entered by pressing notes button 458 on result screen 422, the add notes button 280 on home page 200, and from data collections on the logbook page accessed by pressing logbook button 259 on home page 200. Notes can be added by scanning a bar code or chip, or the like, such as of a food item. Notes entry page 500 can include one or more tick fields to characterize the note as conveying information about food intake (field 581), one or more types of medication such as rapid acting insulin (field 582), long acting insulin (field 583), exercise (field 584), and medication (field 585), and the like. The tick fields shown here include an empty box where a user's touch will change the field's value back-and-forth between a yes value where a check mark is present and a no value where the check mark is absent (empty box). Other alternative fields can be used as well, including tick fields with more than two values, and drop down menus.

More specific information about quantities of food and insulin can be entered into entry boxes 586 located below corresponding tick fields. At least one freeform text box 587 can be present for entry of a textual note about any action taken by the user (e.g., quantity of time exercised, dosage of a particular medication, type of food consumed) or other condition that the user wishes to record. Text can be entered through a keyboard (or virtual keyboard on a touch screen) or verbally, e.g., by using a speech recognition function. Once notes are entered, they can be saved and one or more identifiers, such as icons representing the added notes, are placed at the appropriate times on various glucose level graphs. For example, a graphical meal icon representing food intake or a graphical medication icon indicating insulin injections can be added to the daily graph 766 (see FIG. 7) or the glucose graph 457 along with amounts or doses taken.

Figures 6A, 6B:
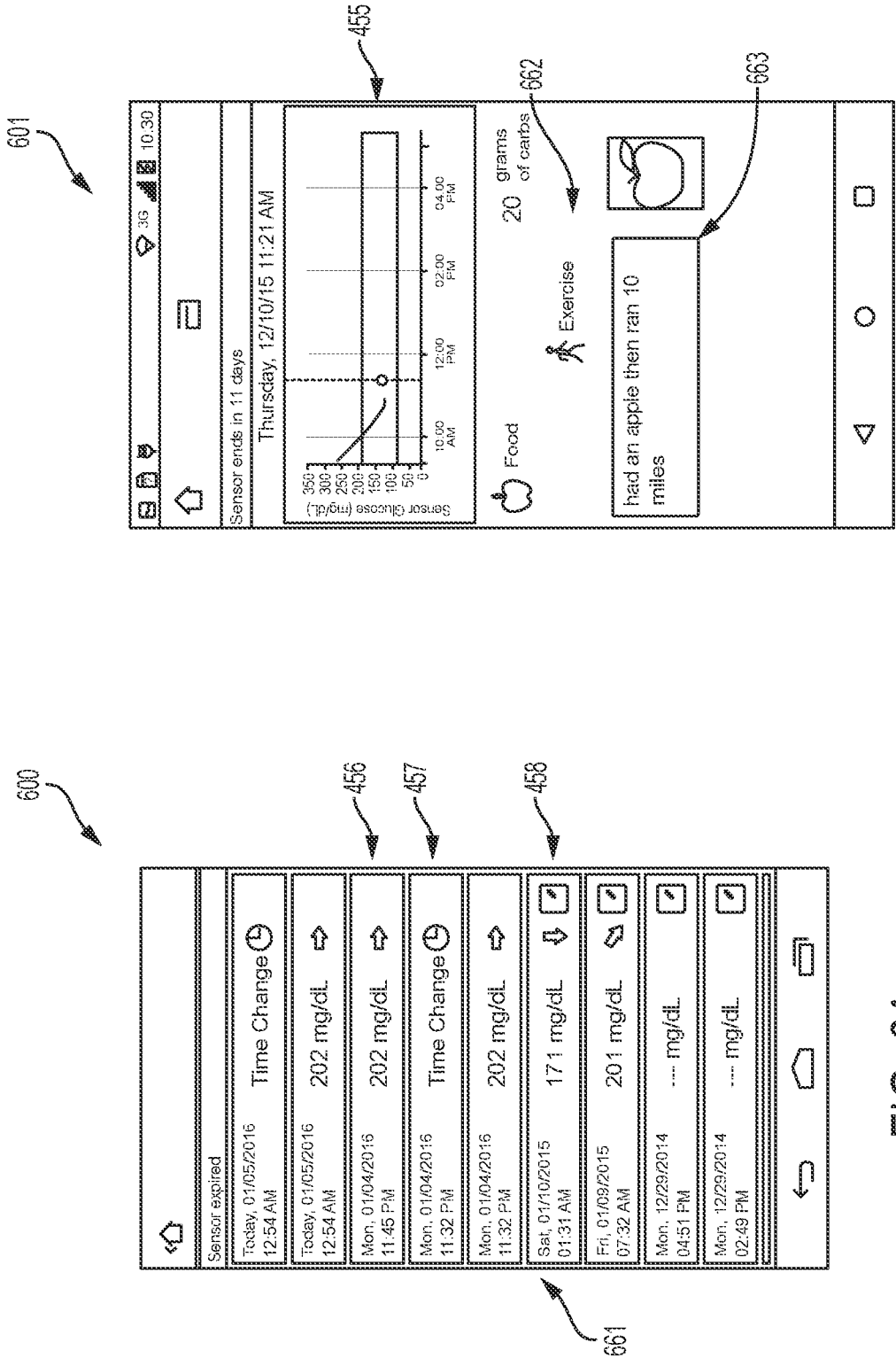

Referring again to FIG. 2, pressing logbook button 259 can open the logbook screen 600, an example embodiment of which is depicted in FIG. 6A. The logbook screen can include entries 661 for each data collection from sensor control device 110 and added notes. Date and time of each entry can be included, along with one or more of a display of a current glucose level, directional rate of change arrows 456, and symbols for time changes 457 and notes 458. Selecting an entry can open a summary screen 601, an example embodiment of which is depicted in FIG. 6B, with detailed information associated with the selected entry including one or more of a graph 455 of historical glucose levels around the time of the log book entry, directional rate of change arrows 456, and any notes 662, free form text 663, and/or images added by the user.

Figure 7:
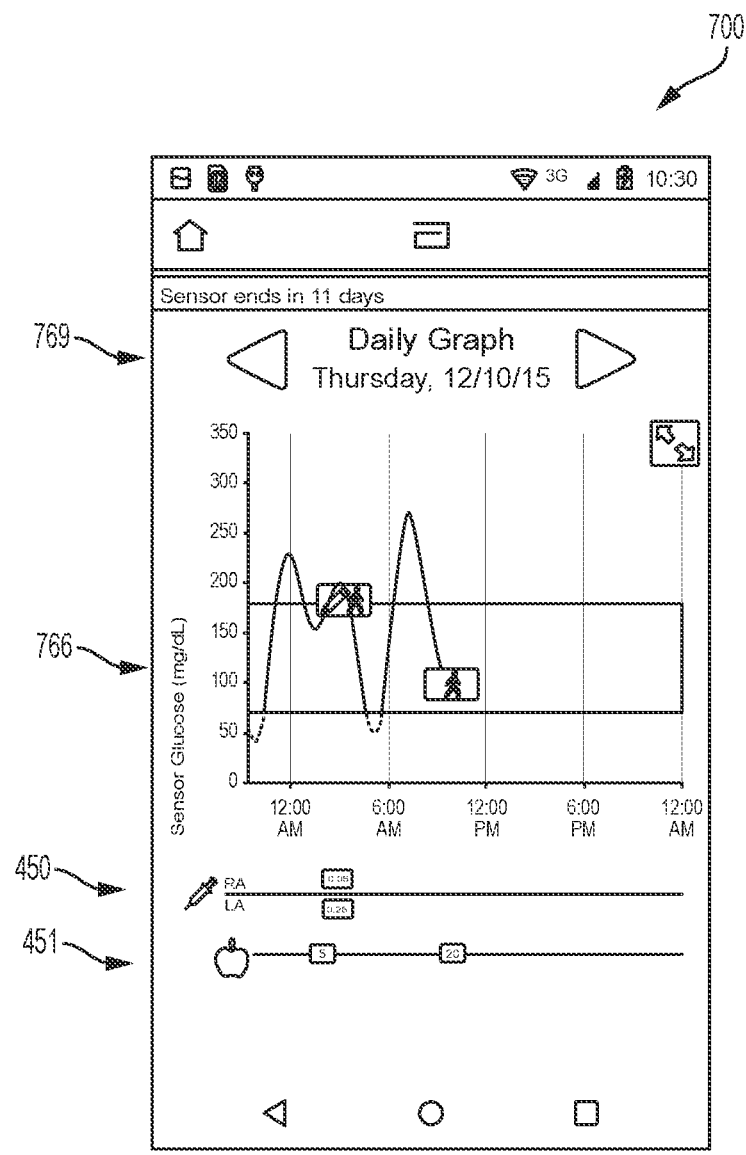

Pressing daily graph button 265, shown in FIG. 2, can open daily graph page 700 shown in FIG. 7. Daily graph page 700 can include a graph of glucose level readings 766 for the day 769 shown at the top of the page and/or timeline graphs 450 and 451 associated with user-entered notes, for example, food intake and insulin usage, identified with symbols. Icons 768 representing, for example, times of exercise, medication dosing, etc., also can be shown on the glucose trace itself within graph 766. The graphs can share the same horizontal time scale axis which can provide a graphical representation of how insulin levels may be affected by exercise or taking food, insulin, or medications. The time scale of the graphs can be changed by using two fingers to pinch or expand the graphs and can be shifted by dragging the graph left or right. Time increments on the graphs can be adjusted, for example, from 30 minutes to 9 hours, allowing either a detailed view, e.g., over a few hours, or an overview, e.g., of about a day and a half. Selecting any of the displayed symbols, for example, medication dosage, exercise, food intake, or insulin usage, can open a pop-up screen displaying notes for that time of day entry.

Daily graph 766 of glucose level readings is similar to the glucose graph 457 of FIG. 4B. Daily graph 766 can display glucose level readings up to a predetermined level, for example, 350 mg/dl. Readings greater than the predetermined level can be sticky, in that they can be displayed as the predetermined level. Gaps can appear in graph 766 if data from sensor control device 110 has not been collected frequently enough, for example, at least once every 8 hours. If the time on reader device 120 changes, a clock symbol can appear and gaps, overlaps, or hidden data can result.

As described earlier, adding notes can be useful in determining patterns in glucose levels. However, it can be problematic for a patient to remember to add notes, especially after an extended period of time has elapsed since the event. Additionally, examining the logbooks in an attempt to correlate specific activities in the notes with glucose levels can be daunting for both the patient and HCP.

In some embodiments, episodes can be detected by the EIS when glucose level readings are received by reader device 120. Adding notes and other information when specific episodes occur can greatly improve the ability to correlate specific behaviors with corresponding changes in glucose levels. The EIS can prompt the patient to input information when an episode is detected and the patient's responses to the prompt, and other patient-entered notes, can be used to assess the behaviors that may be causing the changes in glucose level.

Figure 8:
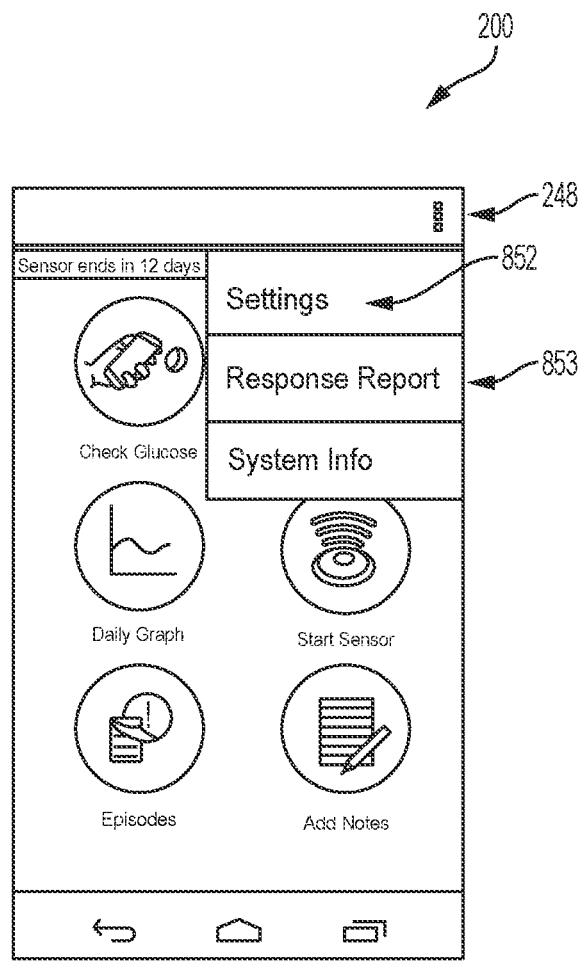
Figure 9C:
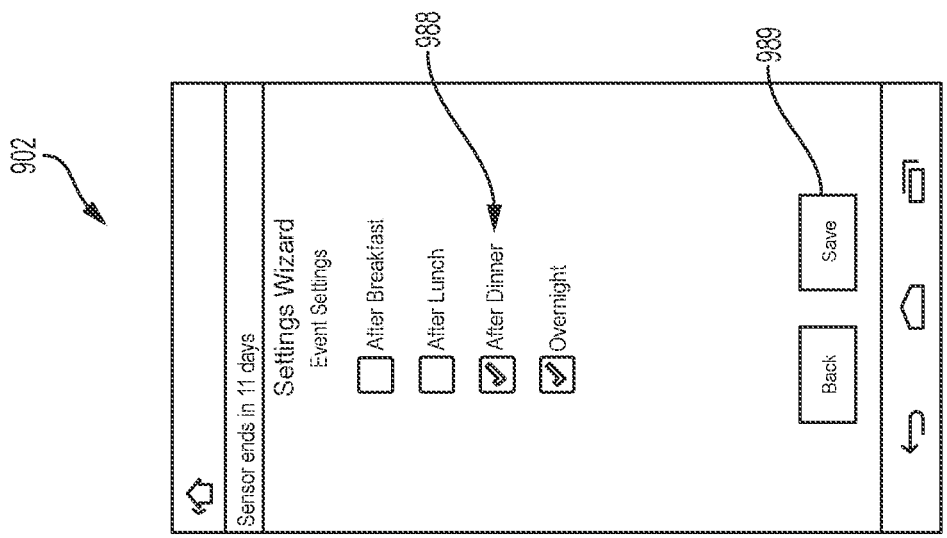

Episode detection can be configured through server 130 or the user interface of the EIS. The process can be similar for both. On reader device 120, menu button 248 can be selected from home page 200 (see FIG. 2) of the EIS. From the dropdown menu shown in FIG. 8, selecting the settings button 852 can start a settings wizard and open the daily events settings screen 900 in FIG. 9A. The daily events can include one or more of breakfast, lunch, dinner, bedtime, and other events, and can be displayed along with default times of day for each of these events on corresponding time of day buttons 985. Selecting the time of day buttons 985 can allow the user (e.g., the HCP, patient, and/or caregiver) to adjust the times to those typical for the diabetic and can set time of day periods for use in certain displays described below.

Figure 9B:
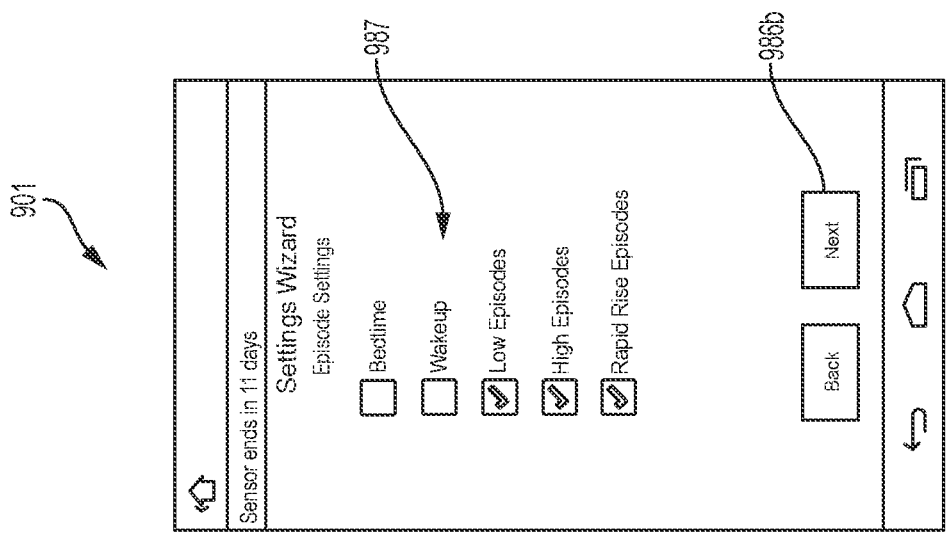
Figure 9A:
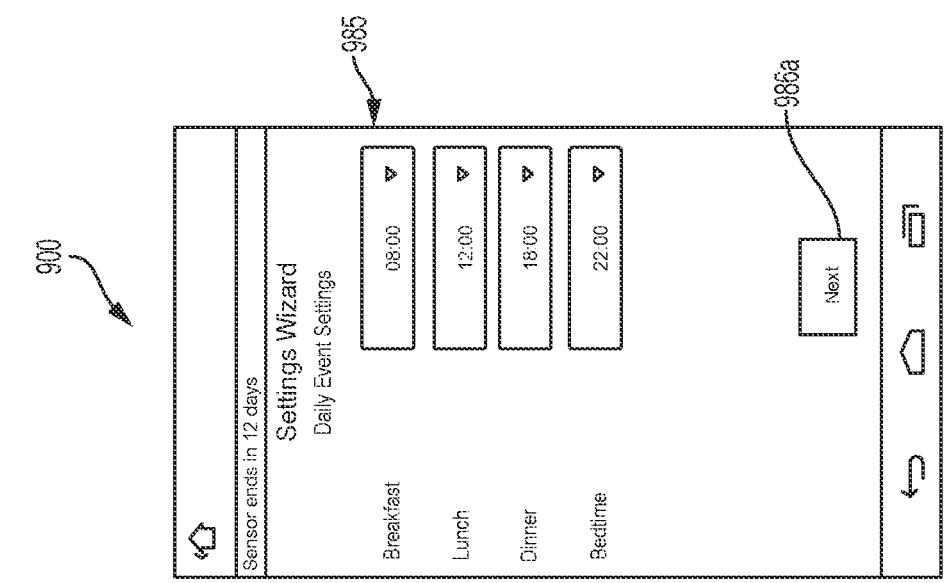

Once the times of day are set, selecting the next button 986a can open the episode settings screen 901, an example embodiment of which is depicted in FIG. 9B. On screen 901 the type of episodes to be detected can be chosen by selecting check boxes 987 corresponding to the type of episode desired. Episodes can include one or more of bedtime, wakeup, and actual or impending low episodes (low glucose levels, e.g., less than a predetermined value), actual or impending high episodes (high glucose levels, e.g., greater than a predetermined value), and actual or impending rapid rise episodes (e.g., glucose levels are rising at a rate greater than a predetermined rate, e.g., 1 mg/dl or 2 mg/dl per minute), and actual or impending rapid fall episodes (e.g., glucose levels are decreasing at a rate greater than a predetermined rate, e.g., 1 mg/dl or 2 mg/dl per minute). The episode triggers, e.g., the levels and rates of change, can be selectable from predetermined options or can be customized. Additional episodes can be defined by the user in the EIS.

Once the episode types are chosen, selecting the next button 986b displays the event settings screen 902, an example embodiment of which is depicted in FIG. 9C. On screen 902, the user can choose the times of day that episode detection can occur by selecting fields 988 (e.g., check boxes) corresponding to the times of day. Times of day can include one or more of after breakfast, after lunch, after dinner, overnight, and times of day associated with customized events. Selecting the save button 989 can save the configuration and activate episode detection.

Episode detection can be highly configurable and include many options. Episode detection can be enabled for one or more of selected time of day periods, certain days of the week, specific days, weeks, or months, or elapsed time. When episode detection is enabled, data from the selected time of day periods are used for episode detection, however, prior data outside the selected time of day period can be used to determine if and/or when an episode occurred. Episode detection also can include an option to prompt the patient with one or more predetermined questions if an episode is detected. Predetermined questions can be based on the type of episode detected. Additionally, new questions can be added, e.g., by the HCP, caregiver, patient, or the like.

In some embodiments, the EIS can include an optional automatic configuration wizard to facilitate configuration of episode detection that best suits a patient's needs. Automatic configuration can be implemented from either reader device 120 or server 130 and episode detection can be enabled immediately after automatic configuration completes or after review and manual implementation by the HCP, caregiver, and/or patient.

Figure 10:
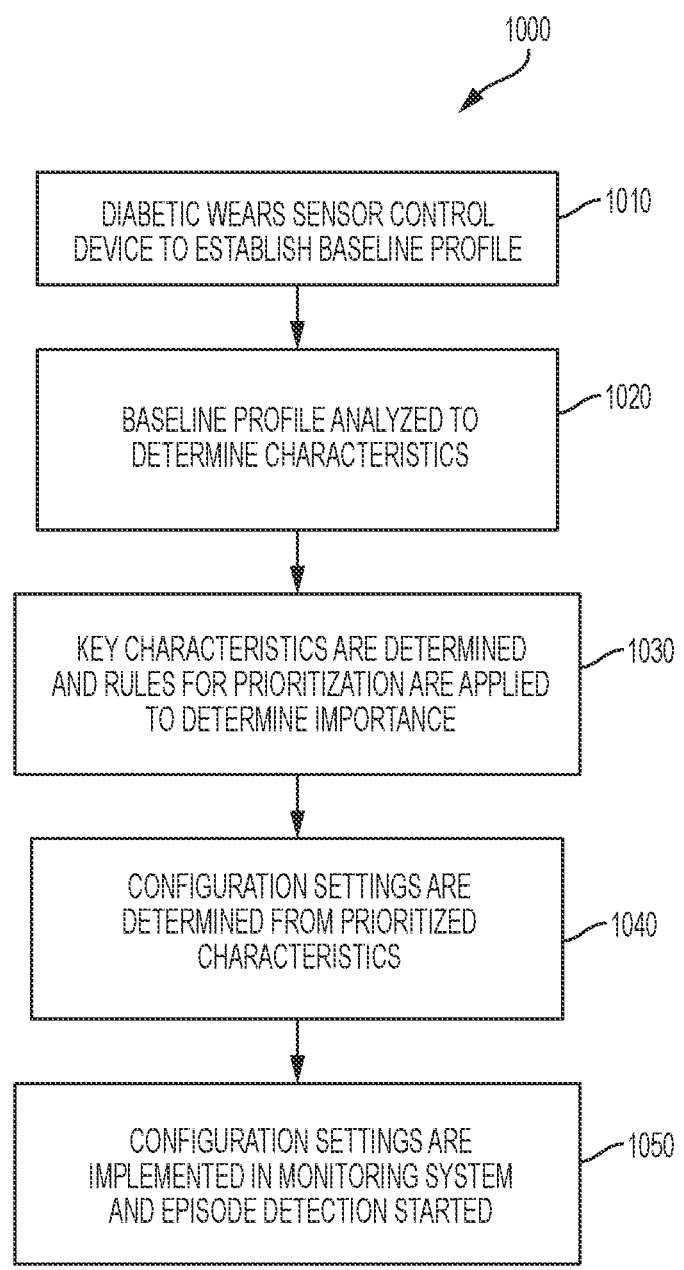
FIG. 10 is a flow diagram depicting an example embodiment of automatic configuration of the episode investigative software.

An example embodiment of an optional automatic configuration 1000 is depicted in the flow chart of FIG. 10, which can begin with the patient wearing a sensor control device 110 for a predetermined period of time, for example, 1-2 weeks, to establish a baseline glucose profile at step 1010. In the first instance that the patient wears sensor control device 110 the resulting profile will typically be the first or "baseline" profile for the patient. Of course the profile can be revised any number of times, such as at follow-up visits with the health care professional, and thus any glucose profile can be used in this method. The EIS can be executed during this time in the masked mode where glucose level readings are not made known to the patient; alternately, this process may be executed with glucose profile data that was collected when reader 120 was unmasked. In some embodiments, the patient can input notes during the automatic configuration period, while in other embodiments, the notes feature is disabled. At the end of the automatic configuration period, the data can be analyzed by the EIS or the glucose monitoring application on reader device 120 using any of the techniques disclosed in the incorporated U.S. Patent Application Publications 2014/0088393A1 and 2014/0350369A1 to determine characteristics of the baseline glucose profile at step 1020.

In step 1030, key characteristics can be determined and rules for prioritizing them can be applied to determine which are most important for the patient. For example, the EIS can have an automatic time-of-day period enablement function that determines, e.g., based on the user's analyte level profile and/or historical times when episode occurrences are relatively high, whether to enable the EIS to detect one or more types of episodes. In some embodiments, the function can enable the EIS to operate at a first period of time of the day to detect one type of episode (e.g., hypoglycemia, etc.) and operate at a second, different period of time of the day to detect an episode of a second different type (e.g., rapid rise, hyperglycemia, etc.). In other embodiments the function can enable the EIS to operate at certain periods of time to detect episodes of all types. Any combination of the two can also be implemented. If the EIS is enable for a particular time of day period (e.g., 8 am-noon, 6 pm-8 pm, etc.), then the EIS can operate to detect the desired episode types every day of the week during that time period, while the EIS is then disabled at all other times. Further granularity can be implemented such that different time periods are enabled based on the day of the week (e.g., 8 am-noon only every Monday, Wednesday, and Friday, or 6 pm-8 pm only on weekend days). In these and every embodiment herein, the EIS can operate continually or repeatedly in real-time to detect episodes, or can operate only at certain times to detect episodes, as described herein.

In one example embodiment, a prioritization rule or condition set for enabling a particular time-of-day period for low glucose episode detection is:

Enable EIS for a first time-of-day period if:
    Likelihood of Low Glucose is HIGH during that first time-of-day period;
    and Variability below Median is HIGH or MEDIUM during that first time-of-day period.

Otherwise enable EIS for that first time of day period if (e.g., "Else if"):
    Likelihood of Low Glucose is not HIGH for any other time-of-day periods;
    and Likelihood of Low Glucose is MEDIUM during that first time-of-day period;
    and Variability below Median is HIGH or MEDIUM during that first time-of-day period.

In another example embodiment, a prioritization rule or condition set for enabling a particular time-of-day period for high glucose and rapid rise episode detection is:

Enable EIS for a first time-of-day period if:
Likelihood of Low Glucose is LOW for all other time-of-day periods;
and Median Glucose is HIGH during that first time-of-day period;
and Variability below Median is HIGH or MEDIUM during that first time-of-day period.

Otherwise enable EIS for that first time-of-day period if (e.g., "Else if"):
Likelihood of Low Glucose is LOW for all other time-of-day periods;
and Median Glucose is LOW for all other time-of-day periods;
and Median Glucose is MEDIUM during that first time-of-day period;
and Variability below Median is HIGH or MEDIUM during that first time-of-day period.

Likewise, other combinations of logic can be implemented in a fashion similar to these examples. The determinations of the severity of a risk or characteristic (e.g., low, medium, or high, or others) can be made by reference to the diabetic's most recent or other selected glucose profile, to a plurality of selected glucose profiles, and/or other historical glucose data. Descriptions of various approaches for defining a particular risk or characteristic (e.g., likelihood of low glucose, median glucose, variability below median) as well as various approaches for quantifying the associated severity of the risk or condition (e.g., low, medium, or high, or others), any of which can be used with the embodiments described herein, are set forth in the following references that are incorporated by reference herein in their entireties for all purposes: U.S. Publ. No. 2014/0187887; U.S. Publ. No. 2014/0188400; and U.S. Publ. No. 2014/0350369.

At step 1040, prioritized characteristics can be used to determine the appropriate settings for configuring episode detection. Configuration settings can be set in the EIS and episode detection can begin at step 1050. Automatic configuration 1000 of episode detection can be instead of, or in addition to, manual configuration. The full range of configuration settings can be accessed by the HCP, caregiver, and/or patient to further customize the configuration after automatic configuration 1000 is complete.

Episode detection, as previously mentioned, can be used with one or more in vivo analyte monitoring systems (both masked and unmasked modes), ex vivo systems, including, for example, ex vivo systems coupled to, including integrated with, an in vivo system. In unmasked analyte monitoring systems, episode detection can occur a) every time glucose level readings are transferred from sensor control device 110 to reader device 120, b) periodically, for instance, every 5 minutes or every 15 minutes, or c) whenever the user activates the EIS or reader device UI. The transfer can be patient-initiated or can be automatically prompted by the EIS. Automatic prompts to transfer glucose level readings can be configured to occur at predetermined times or intervals, for example, daily at bedtime or at least once every 8 hours.

Glucose level readings measured since the last transfer can be transferred and the episode detector of the EIS on reader device 120 can process the data automatically to detect episodes. If an episode is detected, the EIS can notify the patient that an episode has been detected and prompt the patient to respond to questions about the episode. Patient responses can be time stamped and entered via one or more of a keyboard, a touch screen, a virtual keyboard, for example, a keyboard displayed on a touch screen, an audio recorder, and other input device. Glucose level readings and patient responses can be uploaded to the server 130.

Masked in vivo analyte monitoring systems and ex vivo systems work similarly to unmasked analyte monitoring systems, but can have some differences. For example, in masked systems, to avoid influencing patient behavior, glucose level data may not displayed. As with unmasked systems, episode detection can occur when glucose level readings are transferred to reader device 120, however, in masked and ex vivo systems, the patient may not be prompted that an episode occurred, but can be prompted to respond to questions, including, for example, questions with respect to activities and conditions at the time of episode occurrence. To further reduce influencing the patient's behavior, episode detection can occur using glucose level readings from a pre-determined period of time, for example, the time period starting 24 hours prior and up to the current time, the time period starting 24 hours prior to and ending 2 hours prior to the current time, etc.

In ex vivo systems, glucose level measurements can be added to the EIS manually, or if the ex vivo system provides communication support, can be wirelessly transmitted to the EIS. Episode detection is performed on the data input into the EIS, and if an episode is detected, the patient is prompted to respond to questions about the episode. Patient responses are time stamped and can be entered via the touch screen and/or via the audio recorder. Glucose level readings and patient responses are uploaded to the server 130. In certain embodiments, an ex-vivo measurement system can be coupled to, including integrated with, an in vivo system. For example, an in vivo housing can include an ex vivo test strip port, and circuitry for both in vivo and ex vivo measurements. In these cases, the episode detection and patient response input features can be added to the integrated system.

Episode detection can also occur in the glucose monitoring application. The episode detector can use an array of glucose level readings and configuration parameters as input. Iterative examination of the glucose level readings can be searched for patterns using the chosen configuration parameters to define criteria for an episode. Episodes can be detected based on the defined criteria and displayed on the result screen. When the episode detector algorithm is active, glucose data preceding the period of interest can be included as input, ensuring accurate episode detection and start time, particularly for an episode that may span the start time of the time period of interest. Additionally, patient responses to questions about the detected episode can be stored on both reader device 120 and the device executing the EIS.

Both the glucose monitoring application and the EIS can operate on the same set of glucose level readings. Running independent episode detection algorithms on both systems can allow configuration of the glucose monitoring application to detect a subset of episodes that the EIS detects, or stated alternatively, the EIS can be configured to detect a superset of episodes that the glucose monitoring application detects. The most clinically meaningful subset of episodes for patient responses can be identified without overwhelming the patient to respond to every episode that can be detected. The EIS can detect all episodes, and as the patient becomes better able to control glucose levels based on behaviors, new episodes can be added to, or replace, the episodes in the subset detected by the glucose monitoring application to further improve patient control of glucose levels.

The glucose monitoring application and the EIS can have different configuration settings, so detected episodes are not transferred from the glucose monitoring application to the EIS. In some embodiments, one or more of the glucose data and patient responses, along with the time stamp, are transferred. The EIS can execute the episode detection algorithm and match patient responses to detected episodes based on the time stamp. Additionally, the EIS can execute routines for identification and characterization of new episodes.

Figure 11:
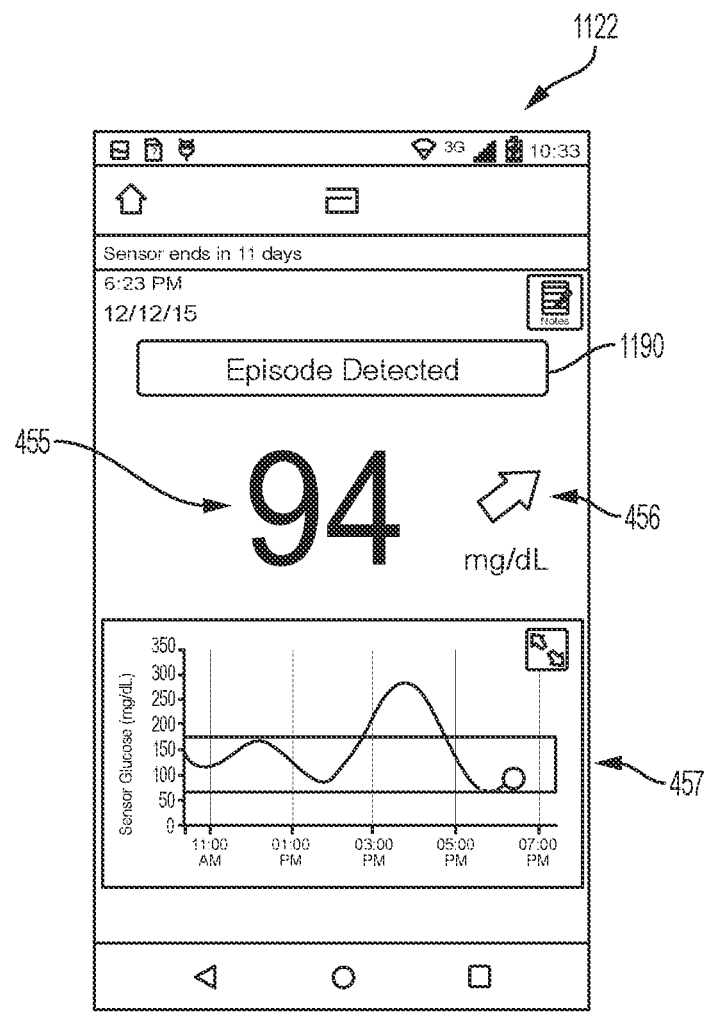

As described previously, when an episode is detected, or multiple episodes, within the previous predetermined time period, for example, the previous 8 hours, the patient can be notified by the EIS and result screen 1122, an example embodiment of which is depicted in FIG. 11, can be displayed. Result screen 1122 is similar to result screen 422 in many respects. In addition to the current glucose reading 455, the screen may include one or more of a trending arrow 456, and glucose graph 457, and an episode detected button 1190. Selecting the episode detected button 1190 can open one or a series of episode response screens displaying questions related to the detected episode. For every episode detected, a separate episode response screen can be displayed, for example, if three episodes are detected then a series of three response screens can be shown and the user can sequentially work through each one.

In an alternative embodiment, a "notification" feature, such as those commonly incorporated into smartphone operating systems, can be used to notify the user of an episode and provide that user with a mechanism to activate the episode response screens. Furthermore, both the episode detection button and the notification feature may be used concurrently.

Figures 12A, 12B, 12C:
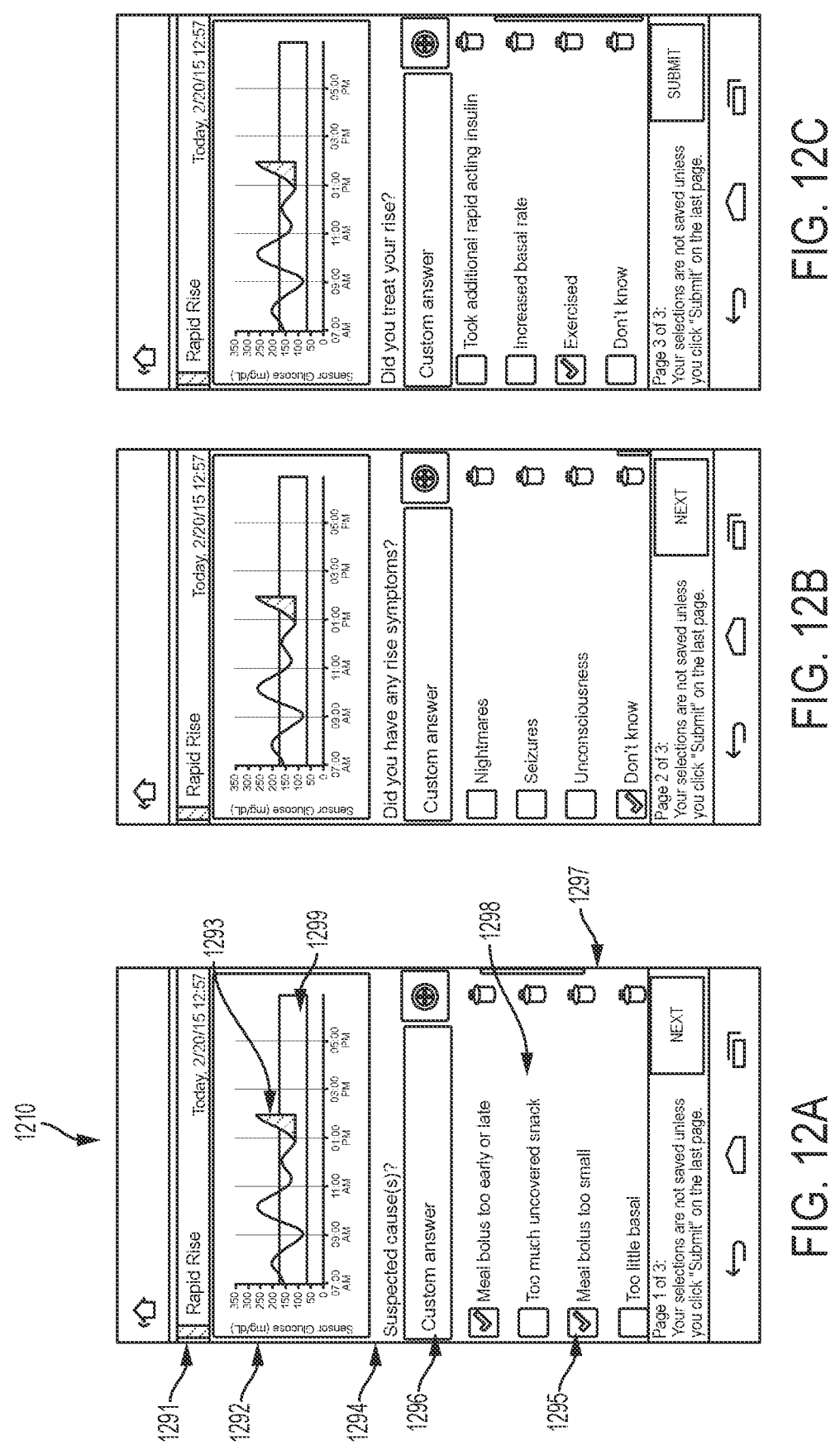

FIG. 12A depicts an example embodiment of an episode response screen 1210. Here, screen 1210 includes an area 1291 where the type of episode detected is displayed. A graph 1292 of recent glucose data, that includes highlights 1293 of the episode, can be displayed. Here the highlight is the shading of the space beneath the graphed curve, and can be in an alternative color from the curve itself. In some embodiments, graph 1292 can be similar to graph 766 described earlier and can also include medication timeline 450 and meal timeline 451 displayed above or beneath graph 1292. The region 1299 of glucose values within the graph that are considered to be normal or within a tolerable range can be denoted, such as with lines or the shading 1299 depicted here.

A question related to the episode can be displayed in area 1294 and a picklist 1298 of possible answers (e.g., reasons or responses), each with a corresponding tick field (e.g., a check box) 1295 for selecting that answer can be included on the response screen 1210. If multiple questions related to the episode are presented, then a picklist 1298 for each question can be included, with each picklist 1298 configured as a drop down menu. In addition to the predetermined responses, a free-form text entry field 1296 can be provided for custom responses (i.e., a response using terms chosen entirely at the user's discretion). If the patient adds a custom response to the text entry field 1296, the custom response can be automatically indicated as an answer, along with any other predetermined response that was selected.

In an alternative embodiment, the user is not provided with the option or ability to create a custom response in the mobile application (and in some embodiments can be prevented in the web-based software as well). If desired, an additional field can be provided where detailed information about the episode can be added, such as a free text note. However, in many embodiments the user is still required to select a preset choice or answer from each of the one or more pick lists presented (e.g., at least one answer for each question presented, where that answer must be selected from the pick list, and where the user does not have the option to add new picklist answers or otherwise customize the pick list except, in some embodiments, through deletion of a pick list answer that is not applicable to the user as described herein).

An improvement in the techniques of managing diabetes (or other medical conditions) can arise from those embodiments that do not provide the option or ability for the user to enter a custom response but rather force the user to select from the preset pick list choices. These embodiments can raise the likelihood that the user thinks critically about which answer is most appropriate, for example, which cause most likely led to the episode occurrence. This can be important because consideration of the potential causes of an episode (or other relevant question about the episode) is often most accurate when that consideration occurs at the same time as the episode occurrence itself (or shortly thereafter). Use of the preset pick list answers provides generalization (avoids excessive specificity) and uniformity to responses and that can assist and simplify the categorization of responses and data analysis at a later stage. Prevention of custom answers can also help prevent a user from providing responses that may not actually respond to the question. For example, a user might, in response to a question about what caused an episode, provide a custom answer that is only a description of what the user was doing at the time the episode occurred, perhaps to save the context for later consideration. While the user can still take such a route by way of the note entry field, forcing the user to respond to a pick list of potential causes can also force consideration of that issue at the present moment, which can be optimal.

In certain embodiments, the user can choose to add the customized answer to the picklist 1298 of predetermined responses, in which case the customized answer will be displayed the next time the same type of episode occurs. In other embodiments, the customized answer is automatically added to the picklist 1298.

Additionally, any responses that are not applicable to the patient can be removed from the picklist 1298 by choosing to delete that response, in this embodiment, by clicking an associated delete button 1297. The deleted response will not be displayed during subsequent instances where that picklist 1298 is shown.

If more responses exist than can fit on the episode response screen 1210, the unseen responses can be seen by scrolling the screen or the unseen responses can be provided on additional screens. After all the questions for an episode are responded to, the next episode detected in the time period that has not been responded to can appear on the result screen 1100. This process of entering responses about the episode can repeated for each episode detected and not previously responded to in the time period. In some embodiments, only the most recent episode can generate a prompt for responses. If responses have already been provided for the most recent episode, the system may not prompt for responses again.

By allowing customizations of the picklists 1298, the process of requesting and receiving input from a particular user is customized towards that user. The burden, or amount of effort, that the user subjectively considers to be required to record information about the episode is relatively lessened. This, in turn, lowers the user's subjective resistance to inputting information, thus resulting in greater usage by the user, which in turn improves the evaluative mechanisms of the system and can lead to the provision of more robust data and more accurate feedback to the user or HCP. If acted upon, the user's glucose variability can be reduced and quality of life improved.

Several questions can be associated with a particular episode. Each question can be displayed on its own episode response screen. FIGS. 12A-12C are non-limiting examples of episode response screens for a detected episode "Rapid Rise." FIG. 12A illustrates a first screen with the question 1294 "Suspected cause(s)?" and 2 predetermined responses selected. FIG. 12B illustrates a second screen with the question "Did you have any rise symptoms?" and one predetermined response selected. FIG. 12C illustrates a third screen with the question "Did you treat your rise?" and one predetermined response selected.

Depending on the episode detected, there can be fewer screens and questions or more screens and questions. Questions and predetermined responses can vary depending on the detected episode, but in many embodiments the first or second screen displayed will query the user with regard to causes of the episode, while the other of the first or second screens displayed will query the user with regard to the symptoms associated with the episode, and the third screen will query the user with regards to what treatment, if any, was applied.

After all episodes are responded to and no new episodes are detected, if the time period is associated with bedtime or wake up, time of day questions can be asked. Time of day questions for a time period can be asked once per day.

Figure 13:
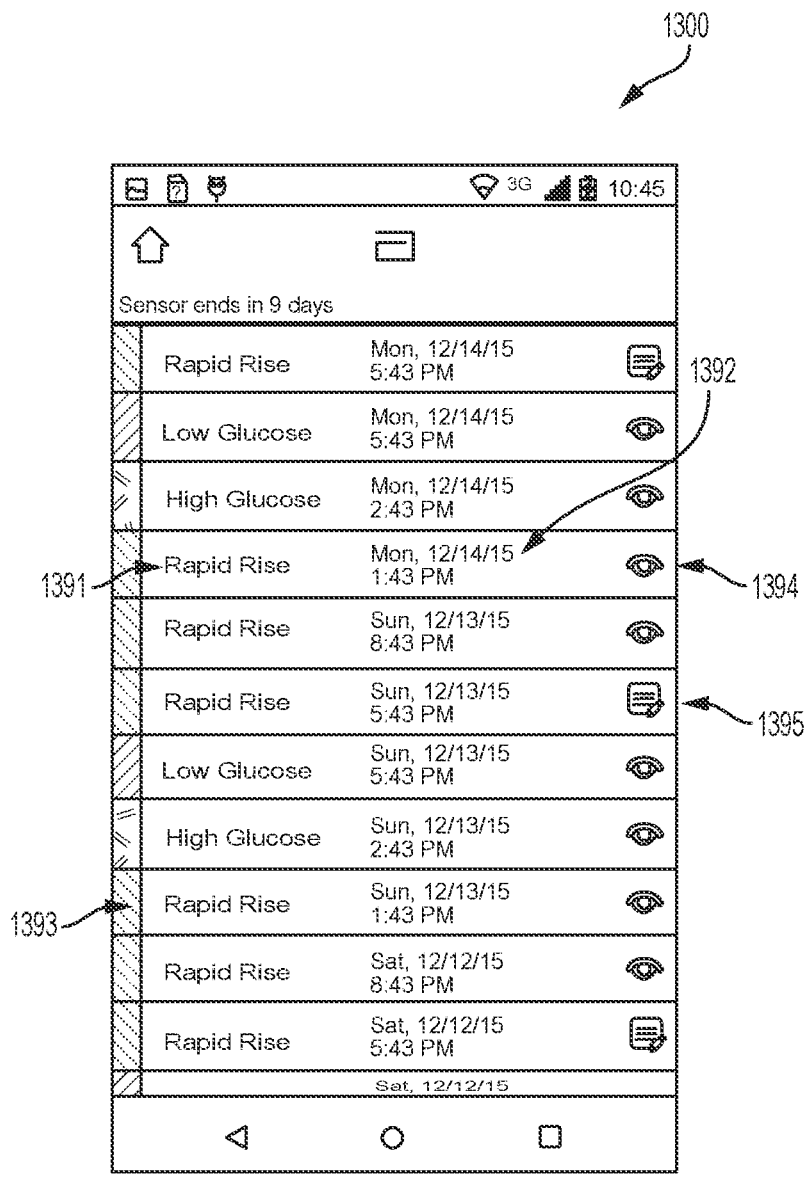

Referring back to FIG. 2, a list of all episodes that have been detected can be displayed by selecting the episodes button 275. FIG. 13 depicts an example embodiment of a list of episodes 1300. One or more of the type of episode 1391, dates and time of episodes 1392, color coded fields 1393 to the type of episode, and icons 1394, 1395 representing whether responses were recorded, can each be displayed. In FIG. 13, a response indicator 1394, for example, an eye-shaped icon, can indicate the patient has recorded responses to questions about the episode, and a non-response indicator 1395, for example a checklist icon, can indicate the patient has not recorded responses. Clicking an episode entry can allow the patient to view previously selected responses to the episode (FIGS. 12A-C) or to allow entry of responses if the patient has not yet responded.

Several reports can be generated to assist the patient, caregiver, and HCP in understanding how the patient's behaviors affect episodes and mitigate the effects of the behaviors. The reports can be generated by reader device 120 using locally stored data or the reports can be generated by server 130 for download to reader device 120 or to a printer.

Figures 14A, 14B:
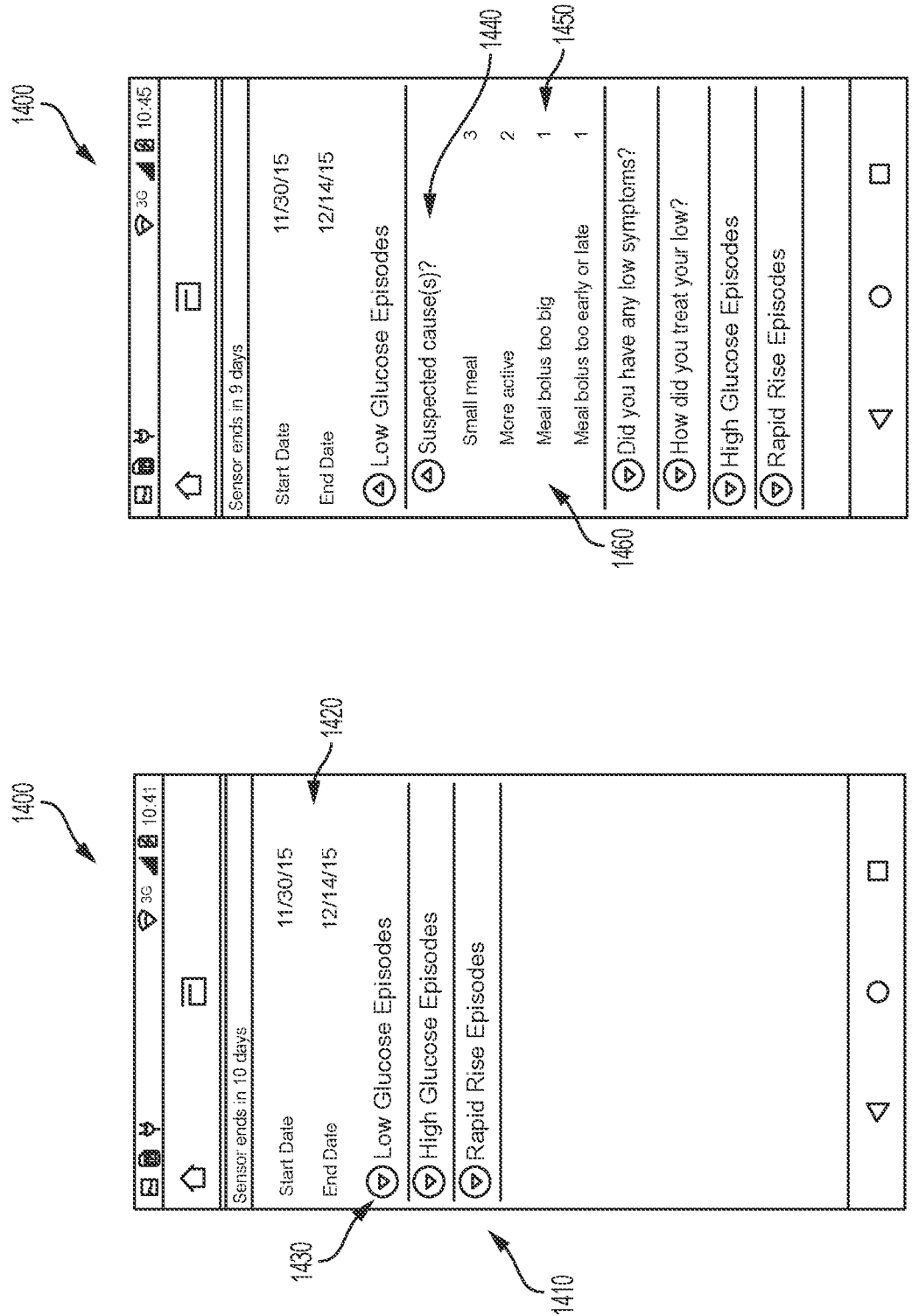

Referring back to FIG. 8, selecting the response report button 853 can open the example response report screen 1400, an example embodiment of which is depicted in FIG. 14A. Types of episodes 1410 having recorded responses can be displayed. The date range for the report can be adjusted using buttons 1420. Clicking a dropdown button 1430 can expand the response report screen, an example embodiment of which is depicted in FIG. 14B, to display one or more of questions 1440 associated with the episode type, the responses 1460 entered by the patient, and a count 1450 of the number of times the response was selected.

Figure 15:
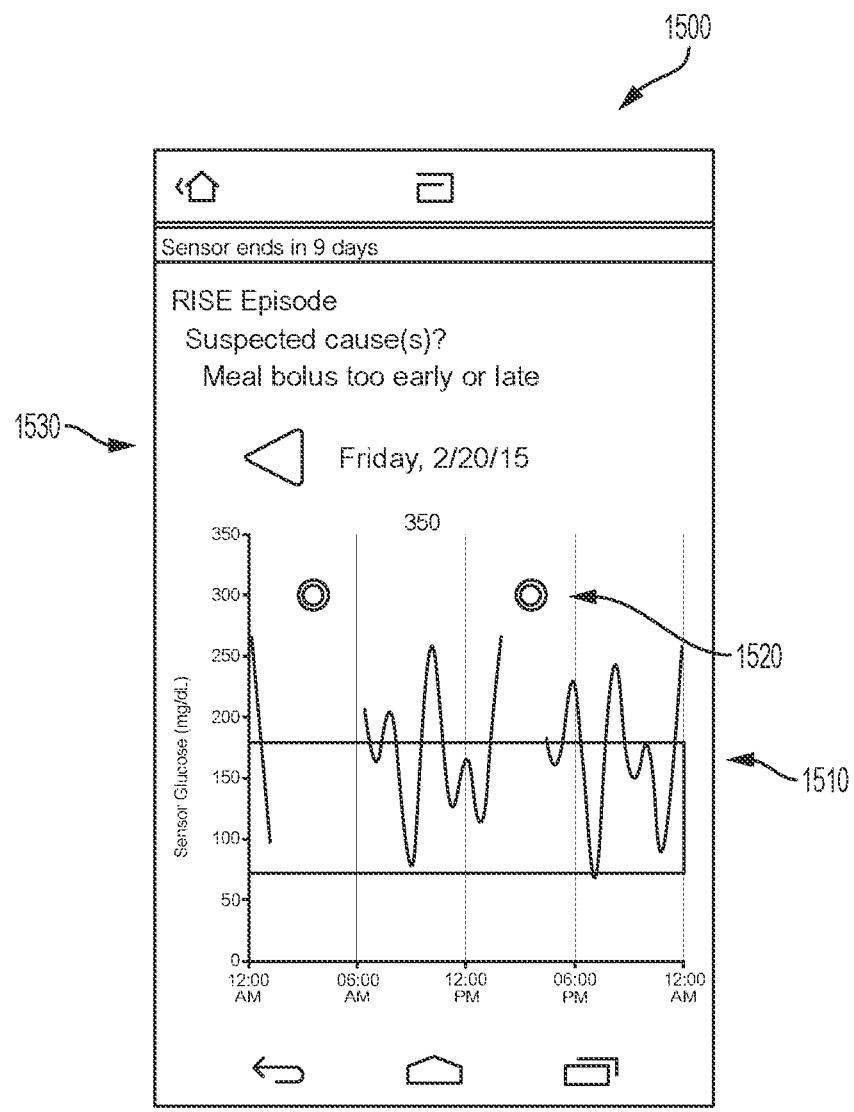

By clicking on a response of interest 1460, for example, "Meal bolus too early or late," a new screen 1500, an example embodiment of which is depicted in FIG. 15, that can include a glucose level graph 1510 and episode indicators 1520, for example, a colored dot (shown) or vertical line (not shown), can be displayed. The graph 1510 can display the most recent day in which the selected response occurred. If the selected response occurred on additional days, a directional indicator 1530 can appear and the additional days can be viewed by clicking on the indicator 1530.

Example Embodiments of Web Accessible Episode Investigative Software (EIS)

With respect to computing devices such as local computer 150 or remote computer 160, the EIS will be described as a software package served from a server 130 and accessible by a web browser on the computing device 150 or 160. Mobile devices (e.g., tablets and smartphones) often have web browsers and are considered a subset of such computing devices, although there may be no need to access the EIS via a web browser if the EIS is already installed on the mobile device as an app.

When a sensor control device 110 conveys data indicative of the diabetic's analyte level to reader device 120, that reader device 120 can be programmed to upload the data (either as raw data in the same general form as received from the sensor control device 110, or as algorithmically processed data (e.g., with proprietary data processing algorithms that may apply temperature compensation or other calibration to the data, etc.)) to a database or server 130 over a wireless and/or wired communication path.

After uploading (and any required data processing performed by server system 130 that did not occur already on reader device 120), the data can be stored and associated with that diabetic such that the diabetic, the HCP, and/or a caregiver (or others) can use a web browser presenting the EIS to access the data. In many embodiments the EIS is capable of presenting the data in different report formats that are designed to convey the underlying information in an improved and nuanced fashion that enables the user to readily understand the information and use the EIS as a tool to identify underlying causes of glucose variability.

An administrator, who is a technical person responsible for managing server 130 and/or accounts associated therewith, can provide the URL to use in the web browser to access server 130. The administrator can be responsible for locking and unlocking accounts. There can be multiple types of user accounts, including those associated with the administrator, those associated with an HCP, and those associated with the diabetic or caregiver. Each account type can have a different feature set that is available to the person who is assigned that type of account. An account can be set up by defining a user ID and password, as already discussed to an extent herein. To access the EIS, a user will enter their user ID and password to gain access to their account and the associated features. Users may have multiple different account types.

The administrator is typically a person that has clinical management responsibilities. The administrator's function is to add HCP accounts. In many embodiments, administrators do not have access to personal data or reports of the diabetic or patient. An HCP user can add patient accounts to the system. In many embodiments HCP users have full access to patient data and reports. The HCP users can supply the patients with an initial user ID and password to be used by a patient to access EIS data and reports via a web browser, and to configure the EIS on their reader device 120 to automatically upload data to server 130.

Upon logging in the HCP user can choose a particular patient from a list of patients associated with the HCP's practice. After selection of the patient, the HCP can generate a review session for that patient by selecting an option to generate a new session, typically from the home screen. An example of when this action would be taken is upon the occurrence of a conference or visit between the HCP (or a representative thereof) and the patient.

Figure 16:
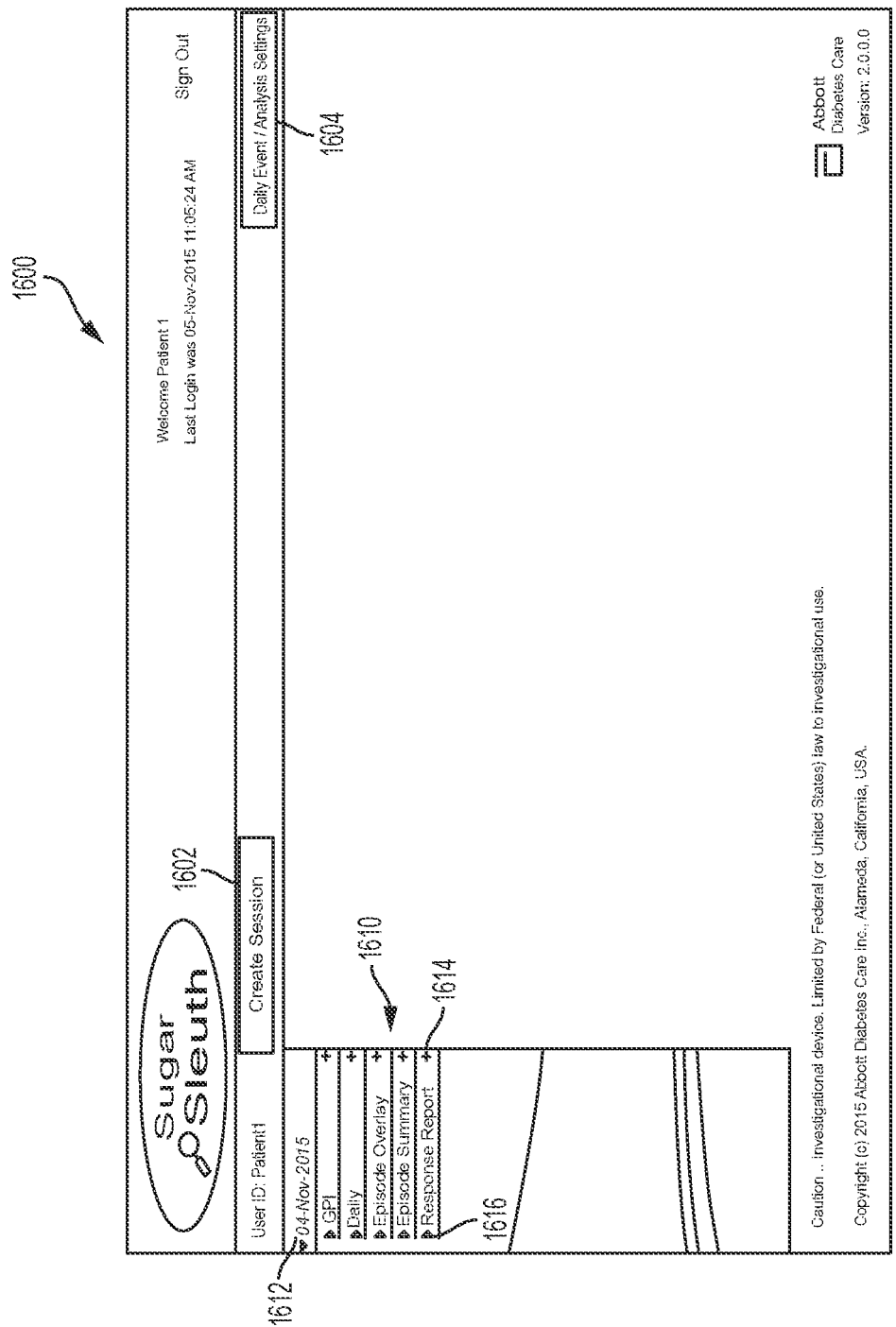
FIGS. 16-22B are diagrams depicting example embodiments of graphical user interface screens that can be displayed on the display of a computing device executing or accessing an example embodiment of the episode investigative software.

An example embodiment of a home screen or page 1600 that is displayable of the display of the computing device (e.g., 120, 150, 160) via a web browser is depicted in FIG. 16. This home screen 1600 can be displayed to the HCP user upon selection of a particular patient, and can also be displayed to the patient user upon logging in. In this embodiment, the EIS is referred to as SUGAR SLEUTH although the subject matter described herein is not limited to that branding.

On the left side of this home screen 1600 is a navigation bar 1610. A session can be generated by selection of a Create Session button 1602, which in some embodiments can be presented only when new data has been uploaded to server 130 that has not yet been viewed through the EIS or since the date or time when the last session was created. When a new session 1612 is created, its date and/or time can be added to navigation bar 1610 (e.g., 4 Nov. 2015), and reports can be generated for this session using all past data up to that date and/or time.

The user (patient, caregiver, or HCP) can create reports based on data collected and uploaded to server 103. Navigation bar 1610 can provide links to separate report types that can be generated within each session 1612. Whenever a new session 1612 is created, a new set of report links can appear along with the session identifier 1612 at the top of the navigation bar 1610. In the embodiment depicted here, the reports available for creation include one or more of a GLUCOSE PATTERN INSIGHTS (GPI) report, a Daily report, an Episode Overlay report, an Episode Summary report, and a Response report. These various report types will be described in greater detail herein.

Prior sessions 1612 (not shown here) can also be displayed below the current session 1612. Reports generated in those previous sessions 1612 can be viewed and edited, but in many embodiments are based only on the glucose data that was available up to the day and/or time when that prior session was created.

A new report can be generated by selecting the appropriate field 1614, which in this embodiment is a plus sign (+) next to the respective report title. Once the new report is generated, a link to that report is located in a position associated with that particular session 1612 (e.g., beneath) in navigation bar 1610. To the extent multiple reports of a particular type are generated, a list of those reports can be expanded or collapsed by selecting that field 1616.

Also on home screen 1600 is a selectable field 1604 to modify report settings, which is labeled here as Daily Event/Analysis Settings. For HCP users, a selectable field 1606 to return to a patient list screen can also be provided. Navigation bar 1610, field 1602, field 1604, and field 1606 can be available on all report screens, such as those described below.

Each of the reports generated with the EIS can be based on one or more days of glucose data from the diabetic. A graphical, interactive data selection tool can be presented by the EIS and can assist the user in readily (and rapidly) identifying those days that contain the most relevant data for analysis. Those days can then be individually selected and used for running the report.

Figure 17A:
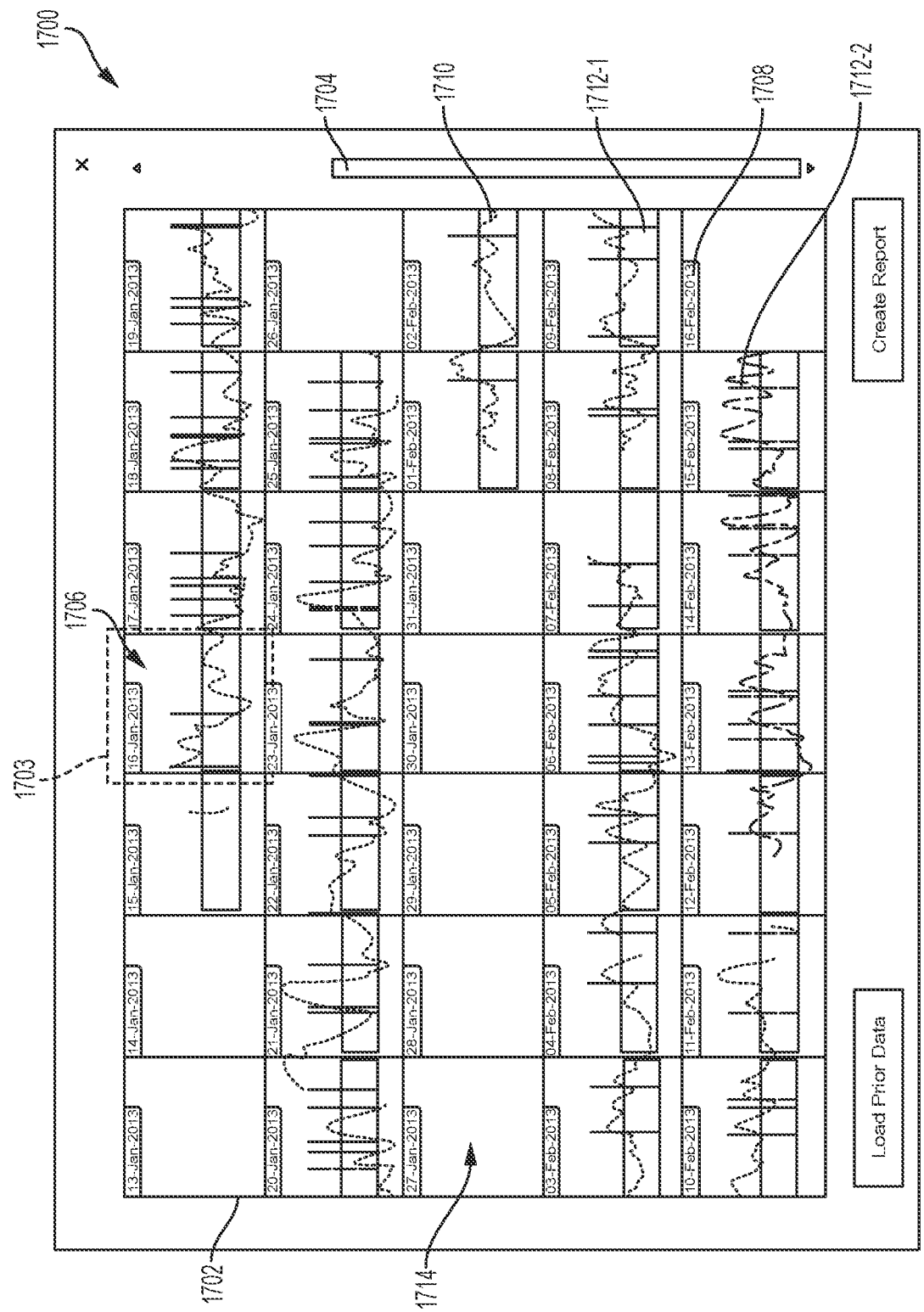
Figure 17B:
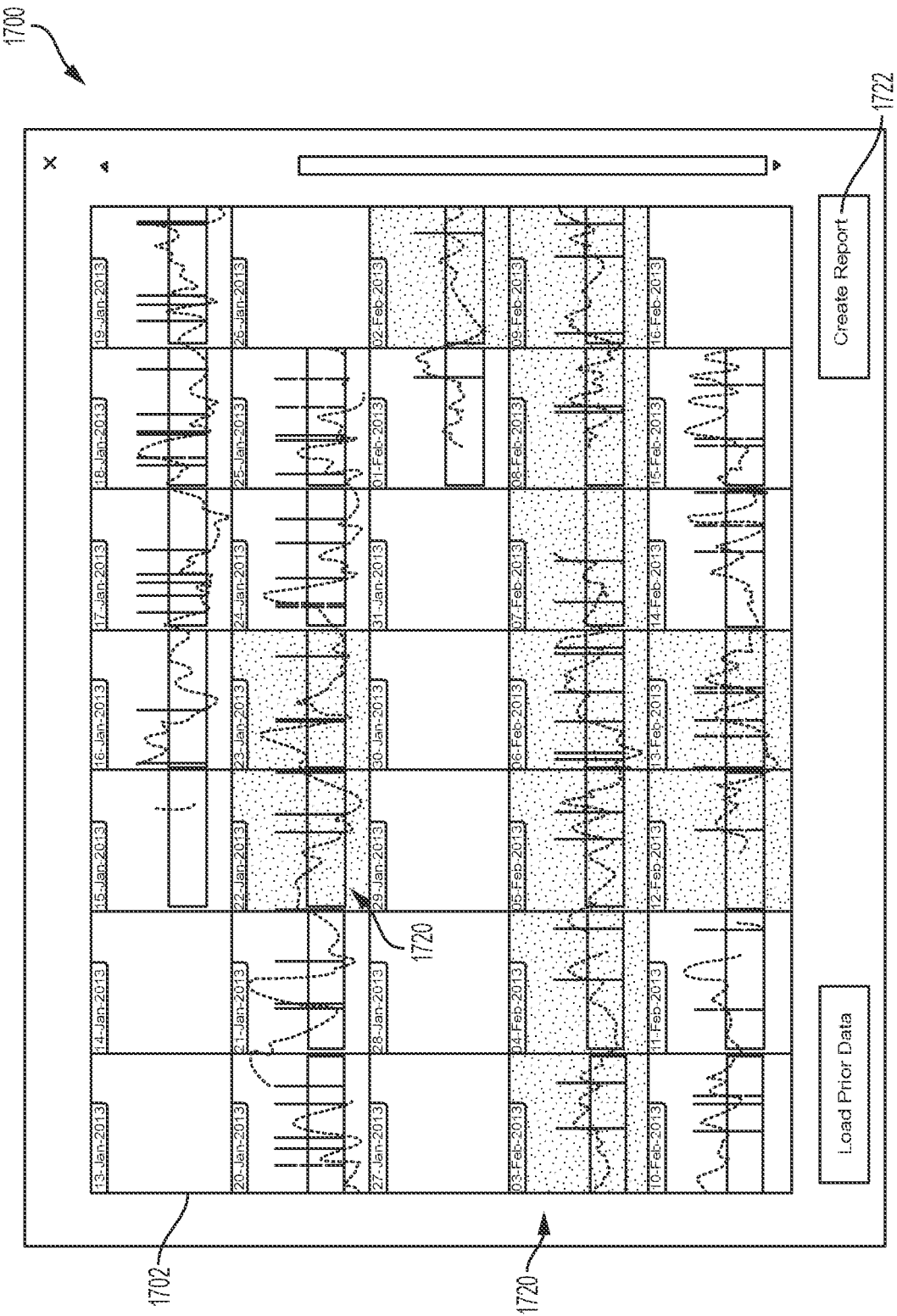

An example embodiment of the data selection tool 1700 is depicted in FIGS. 17A-B. Data selection tool 1700 can be displayed to the user upon selecting the option to generate a report (such as by selecting field 1614 of FIG. 16), or at another point in the report generation process where the selection of the appropriate data set is desired.

In this embodiment, data selection tool 1700 displays data arranged in a grid 1702, where each subdivided region 1703 (e.g., each unit or box), which can be bounded or unbounded, within grid 1702 corresponds to a day, and the days are presented with one week per row (e.g., with Sunday at far left and Saturday at far right). One example of a region 1703 is denoted in FIG. 17A with a surrounding dashed line. The number of days displayed per row is not limited to seven, and any number of one or more days can be displayed per row. Any number of one or more rows can be displayed at any one time (e.g., one, two, three, four, five, six, and so forth.). A vertical scroll bar 1704 can assist the user in scrolling through as many rows as are displayable, the upper limit of which may be set by the amount of weeks in which data is available. For example, there may be five rows of data displayed on the screen at any one time, although ten weeks of data are displayable, with the user being able to scroll through those ten weeks with the vertical scroll bar.

The uppermost row can be the most recent week or current week and the lowermost row can be the week that occurred longest in the past, both as measured from the date and/or time of session 1612, with those rows in between descending back in time in sequential fashion. Alternatively, the weeks can be displayed in reverse fashion, like a typical monthly calendar, where the week that occurred earliest in time is at top and each subsequent lower row is one week later in time.

In alternative embodiments, the grid can be configured such that the days can be displayed vertically in one single column, such that, for example, the most recent day is displayed at top and the day that occurred longest in the past is at the bottom, and vice versa. However, this arrangement does not allow as many of the days to be displayed at any one time.

Within each unit 1703 of the grid is a graphical representation 1706 of the glucose (or other analyte) data for that particular day. A label 1708 that indicates the day of the week and/or the date can also be displayed in or adjacent to unit 1703. The graphical representation, or graph 1706, can have an appearance like that of graph 1292 described with respect to FIGS. 12A-C, or like that of any other glucose graph described herein, including those in the incorporated references. Days for which no data is present, such as day 1714, can be blank, grayed out, or otherwise shaded or indicated to be missing data.

Graph 1706 can include a trace 1710 of the glucose values for that corresponding day, either as a sequence of the measured data points as depicted here or as a broken or continuous line. If each unit 1703 is directly adjacent each other, then trace 1710 can be continuous from one day to the next within each row, as shown here. Each graph 1706 can include an indication or marker 1712 for each episode detected within that corresponding day. The marker 1712 can have any desired shape (e.g., circle, oval, line, curve, square, polygon, triangle, etc.), color, or appearance. For example, marker 1712 can be a vertical line as depicted here, or can be the shaded region 1293 under the trace as depicted in FIG. 12A.

Any combination of shapes, colors, and appearances can be used for marker 1712. For example, episodes of a first type (e.g., high glucose) can be indicated by a first marker 1712-1 of a first shape and/or color, and episodes of a second, different type (e.g., low glucose) can be indicated by a second marker 1712-2 of the same shape but with a different color. In an alternative, one color can be used to indicate episodes of all types, where different episode types are indicated by shape. In still other examples, one shape can be used to indicate episodes of all types, or different shapes can be used to indicate different episode types, but in both cases the severity of the episode is indicated by different colors (e.g., yellow for mild, orange for moderate, and red for severe) or the darkness or opacity of a single color. Severity can also be indicated by the size of marker 1712 (e.g., the more severe the episode, the thicker the vertical line, or the larger the shape, etc.) or by other different shapes or appearances of marker 1712.

The user can then select each day within grid 1702 having data that the user wants to be used to generate the report. As can be seen from FIG. 17A, tool 1700 provides an efficient digest of a large amount of the user's glucose data over what can be a lengthy span of time. This constitutes an improvement that enables the user to more readily and efficiently select data for report generation. For example, because the data for each day is displayed in graphical form, the user may more efficiently identify days with repeating patterns or trends in the glucose traces 1710, and can readily and easily select them. Clusters of days where episodes of a particular type or occurring at a particular time are occurring can be readily identified and selected. Similarly, days where glucose variability and/or episode occurrence was lowest can also be readily identified and selected to search for trends in the diabetic's behavior for those days.

Also, the embodiments of tool 1700 described herein can constitute an improvement in the field of treating diabetes, as tool 1700 allows the identification and selection of the most relevant data sets in a manner that reduces the burden on the user as compared to prior approaches, and which thereby increases the likelihood that the user will use the EIS to investigate and identify the causes of glucose variability and/or episode occurrences, allowing those causes to be ameliorated or treated and thus improving the health and lifestyle of the diabetic or other patient.

Selection of the days can be done directly on the displayed grid 1702, such as by touching each day (in the case of a touchscreen display) or by selecting each day or group of days with a mouse cursor. In either situation, the selection of a particular day can result in only that day being selected (where a previously selected day or days is then unselected).

Selection of multiple days can occur, for example, by holding a first key (e.g., the control key) and selecting each desired day, in which case all selected days will remain selected. A group of days can be selected by holding down a second key (e.g., the shift key) and clicking on a first day of a range of days and a last day of the range, in which case the EIS will automatically select each intervening day in that range. The EIS can be configured so that days 1714 that have no data are not selectable. For reports that rely on only one day of data, such as the Daily report, or on a limited number of days of data, the EIS can be configured to only allow the selection of a number of days equal to or less than the limit.

An example embodiment of a selected group 1720 of days is depicted in FIG. 17B. Here, each day in the selection is indicated by the application of a partially transparent coloring or shading. Other manners of indication can also be used, such as by placing a notable border around the selected days, and the like. As shown here, the user can select non-contiguous ranges of days for use in generating the report. In some embodiments, a default range of days can be selected, such as, e.g., the most recent seven days, the most recent 10 days, the most recent 14 days, etc. When the desired one or more days are selected, the user can generate the report by selecting the Create Report button 1722.

A number of example reports have been and will be described herein. Although these example reports are shown and described in a format that can achieve beneficial results, these reports are not limited to the exact manners in which information is displayed and user interactivity is allowed. Thus, each and every feature (e.g., graph, icon, note, table, list, trace, indicator, selectable field or button, drop down list, response, array of information, ordering of information, etc.) can be modified from the manner in which it is shown and described here while still being within the scope of this disclosure. Further, each and every feature can be added to each and every different report type (or omitted from each and every different report type) unless noted otherwise or logically implausible or impossible, while still being within the scope of this disclosure.

Figure 18A:
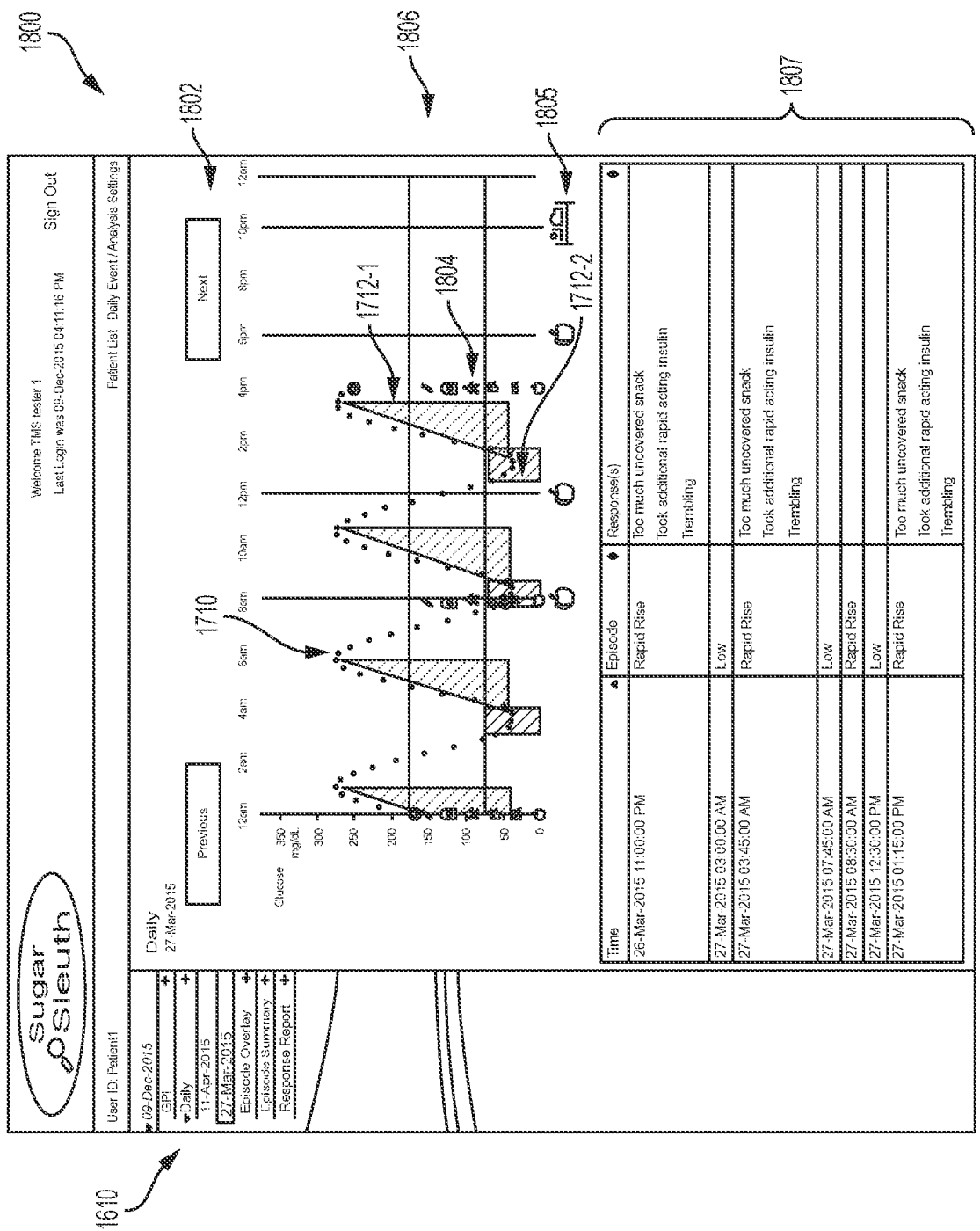

FIG. 18A depicts an example embodiment of a daily report 1800, which, like all reports described herein, can be displayed on the display of a computing device by use of, e.g., a web browser. Daily report 1800 can include a graph 1806 including one or more of a glucose trace 1710 and color-coded markers 1712 for episodes occurring during the time period plotted, typically 24 hours or less. Here, marker 1712-1 is a shaded region beneath trace 1710 that indicates a rapid glucose rise episode (e.g., a rise at a rate that exceeds a threshold for a minimum duration). Marker 1712-2 is a shaded box that indicates a low glucose, or hypoglycemic, episode (e.g., the time in which the user's analyte levels were below a threshold).

Various icons 1804 representing notes entered during that day (such as those described with respect to FIG. 6B, are shown along glucose trace 1710. As described already, each note icon 1806 can indicate one or more of exercise, the consumption of food and/or fluids, the administration of medication (e.g., rapid acting (RA) insulin or long acting (LA) insulin), the presence of a freeform text entry, or the occurrence of sleep, to name a few. Hovering, the cursor over a particular note icon (or touching the note icon as in the case of a touchscreen) can display an overlying pop-up window with additional information about that note (e.g., length of the event, time of the event, calories burned, type of food or drink consumed, amount of carbohydrates or calories consumed, quantity of fluids consumed, dose amount and type, the actual freeform text entry, etc.).

Additional icons 1805 can also be displayed that indicate typical times of event occurrences, which can be set and adjusted by the user. Here, three meal icons (e.g., in the shape of an apple) indicate breakfast, lunch, and dinner. Also shown is a sleep icon (e.g., in the shape of a person in bed) that indicates the typical time the user goes to sleep for the night.

A table 1807 listing and describing each episode can be presented in daily report 1800, for example, beneath the graphical display 1806. Table 1807 can include the time the episode occurred, the type of episode, and any information entered by the user about that episode, such as suspected cause, symptoms, and treatment (see, e.g., the description with respect to FIGS. 12A-C). The table or list can also display note information, for any notes that are entered during the day; it can also display any other recorded information, such as blood glucose readings, etc. Each entry in table 1807 can correspond to a marker 1712 indicating an episode in the graph. Within table 1807, the user can sort episodes and responses by day, episode time-stamp, episode type, or response.

Navigation buttons 1802 (labeled here as Previous and Next) allow the user to scroll one day forward or one day back in time, where the EIS can automatically skip those days without data (if any). Selection of one of the buttons 1802 will cause a daily report 1800 to be generated for either the next or the previous day. Each time a new daily report is displayed, it can be added in the appropriate location in navigation bar 1610.

Figure 18B:
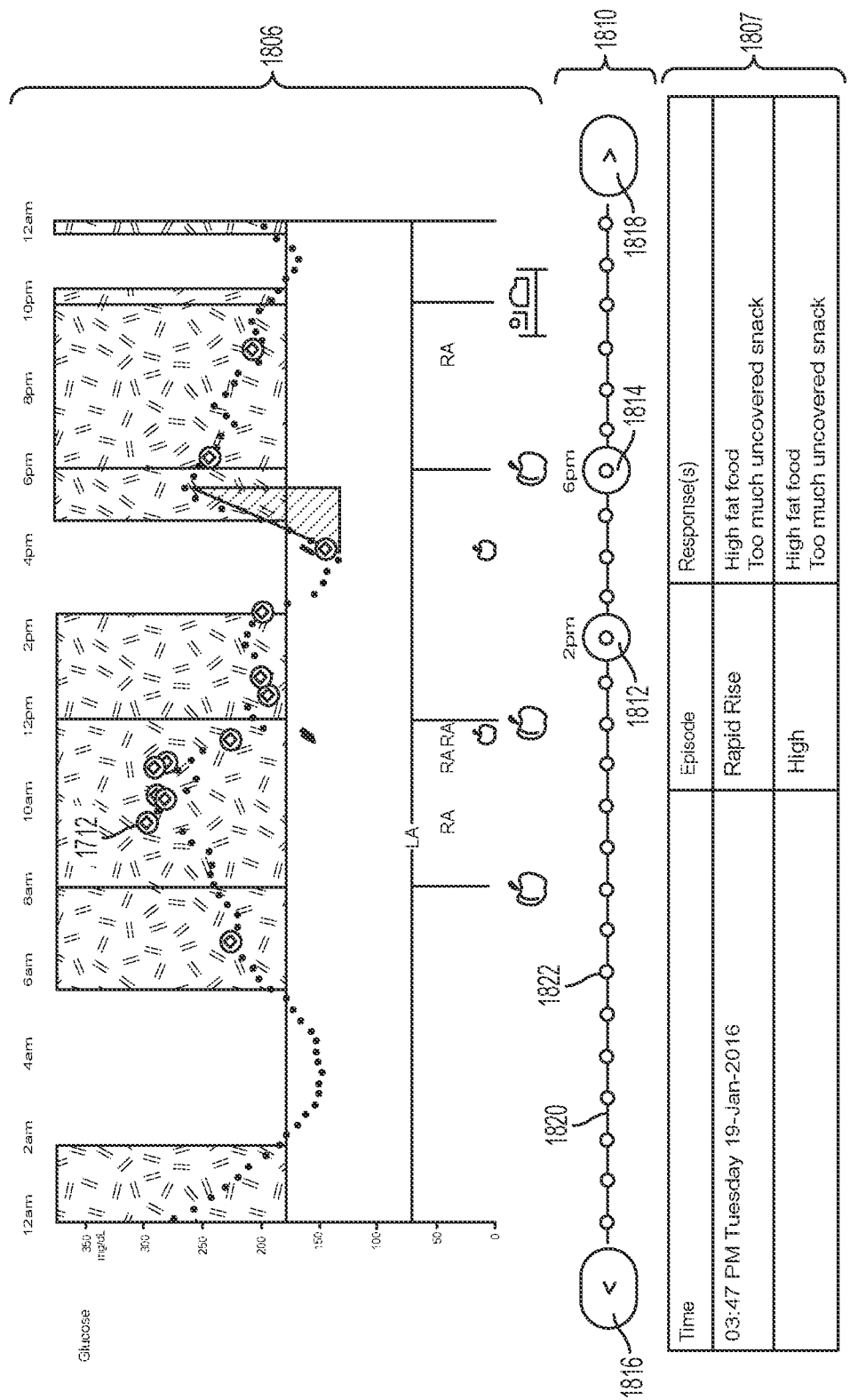

FIG. 18B depicts another embodiment of daily graph 1806 and episode table 1807. In this embodiment, an interactive filter 1810 is located between graph 1806 and table 1807. Filter 1810 allows the user to select which information is displayed in table 1807 based on the position of an indicia for the information in time within graph 1806. Here, the indicia are the episode indicators 1712, and the information displayed in table 1807 is the date and time of each episode, the type of each episode, and the responses recorded with respect to questions posed about the episode. Other information such as notes, photos, etc. can also be displayed. Filter 1810 includes an axis 1820 with two markers 1812 and 1814 that can be slid along the axis by the user in a number of ways. For example, markers 1812 and 1814 can be slid directly, e.g., such as by touching a dragging on a touchscreen or by clicking and dragging with a mouse cursor. The position of marker 1812 along axis 1820 sets the earliest time for the filtering function, while the position of marker 1814 along axis 1820 sets the latest time for the filtering function.

Here, marker 1812 is placed at 2 pm (a label indicating the time at which each marker is placed can be optionally displayed as shown here) while marker 1814 is placed at 6 pm. This placement serves to filter from inclusion in table 1807 all episodes, notes and other information that occurred before 2 μm and after 6 μm in the daily graph 1806. Thus, only those episodes and notes occurring between 2 μm and 6 pm (inclusive or exclusive of those end times) are displayed in table 1807, which in this embodiment is two episodes. Filter 1810 can therefore serve to reduce the amount of information displayed in table 1807, and also to allow the user to focus on only those episodes occurring during a particular time of day. This can be significant for days in which a relatively large number of episodes were detected, such as in the case depicted in FIG. 18B, where approximately fourteen episodes 1712 are indicated in graph 1806. Markers 1812 and 1814 can also be moved indirectly by selecting fields 1816 and/or 1818. These fields slide markers 1812 and 1814 together to the left (field 1816) or to the right (field 1818) such that both markers 1812 and 1814 maintain a constant spacing (for example, four hours as shown here). Axis 1820 can have multiple discrete landing positions 1822 spaced at even intervals, where the position and movement of markers 1812 and 1814 is limited to only those landing positions 1822. For example, clicking and dragging marker 1812 to the left would cause marker 1812 to jump from one landing position 1822 to the next. Likewise, selecting field 1816 would cause both markers 1812 and 1814 to move one position 1822 to the left, thereby changing their respective times from 2 μm and 6 μm to 1 μm and 5 pm.

In this embodiment, each landing position 1822 is separated by an hour, although a greater or lesser interval can be used. In various different embodiments, the interval between all positions 1822 can be 10 minutes, 15 minutes, 30 minutes, 60 minutes, 90 minutes, and 120 minutes, to name a few. In alternative embodiments, no discrete landing positions 1822 are present and markers 1812 and 1814 can take any position on axis 1820, to simulate a continuous or analog-type movement from the user's perspective. Those embodiments where landing positions 1822 are present can be referred to as having non-analog-type movement.

Filter 1810 can be included with any graph or other representation of data described herein having an associated table, such as table 1807 listing episodes. Filter 1810 is not limited to use with analyte level graphs and episode indicators, but rather can be used to filter based on any type of information presented in the reports, such as exercise indicators, meal indicators, sleep indicators, medication dose indicators (e.g., LA insulin and/or RA insulin), textual notes or comments, or even segments of data display in graph 1806 without any overlying indicator (e.g., the analyte data itself). Furthermore, filter 1810 can be used in any instance, including non-medical applications, where it is desired to focus the display of information in one data structure or visual representation (e.g., table 1807) on one portion or part of another data structure or visual representation (e.g., graph 1806).

In the embodiment of FIG. 18B, filter 1810 is oriented horizontally (e.g., in the direction of the X axis), but other embodiments can utilize a filter 1810 that is oriented vertically (e.g., in the direction of the Y axis), a filter 1810 that is oriented in a third direction normal to the horizontal and vertical directions (e.g., in the direction of a Z axis), and any combination thereof. Furthermore, multiple filters 1810 can be used with the same directional orientation, such as with dual-scaled graphs having, e.g., a left side Y scale representing magnitudes of one type of data and a right side Y scale representing magnitudes of a different type of data. Each filter 1810 can be independently adjusted relative to each other filter 1810, where each adjustment of a filter 1810 can cause a real-time adjustment to the information displayed in the dependent visual representation (e.g., table 1807). Thus, any number of one or more filters 1810 in broad range of different manners.

Figure 19A:
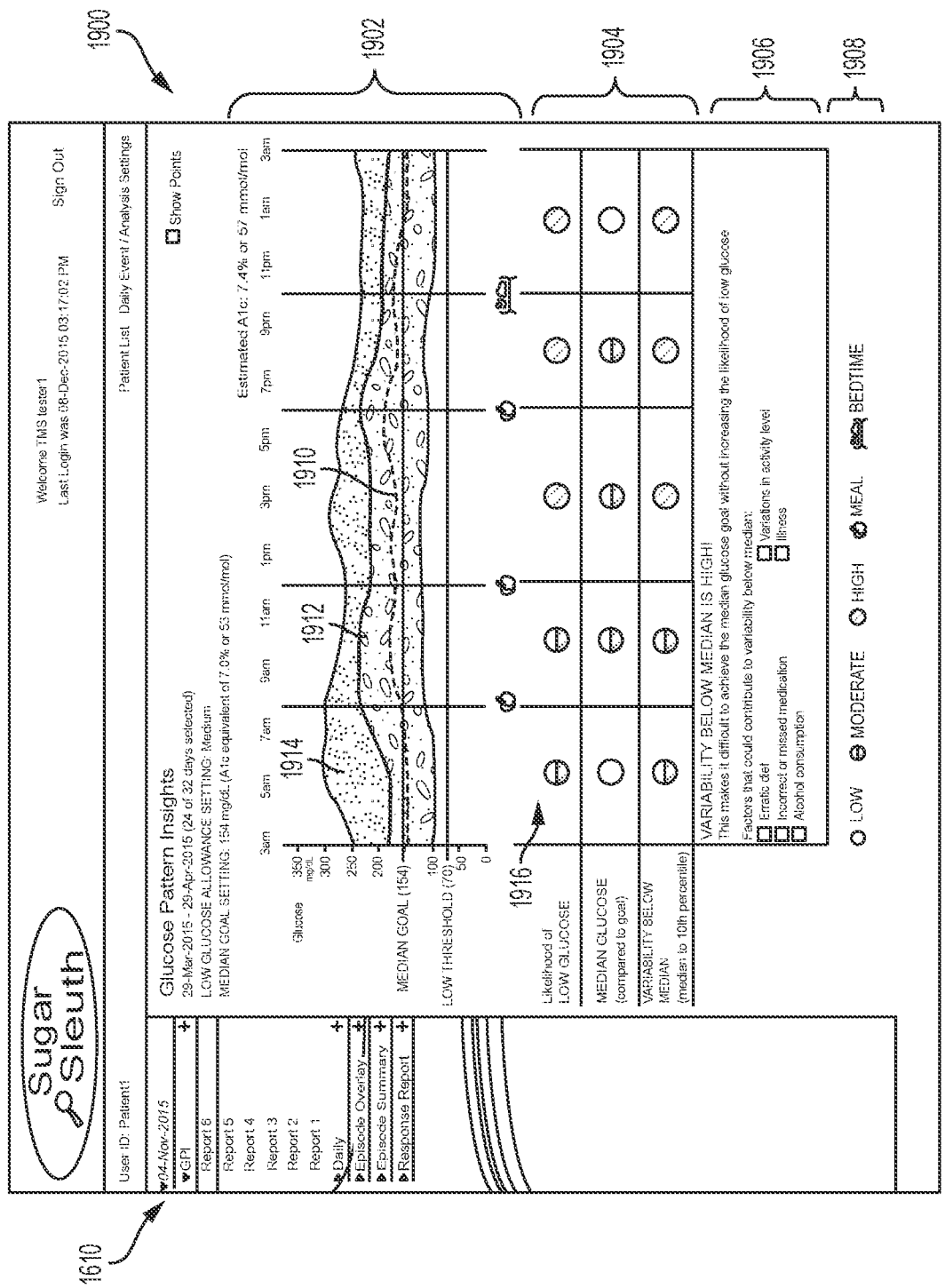
Figure 19B:
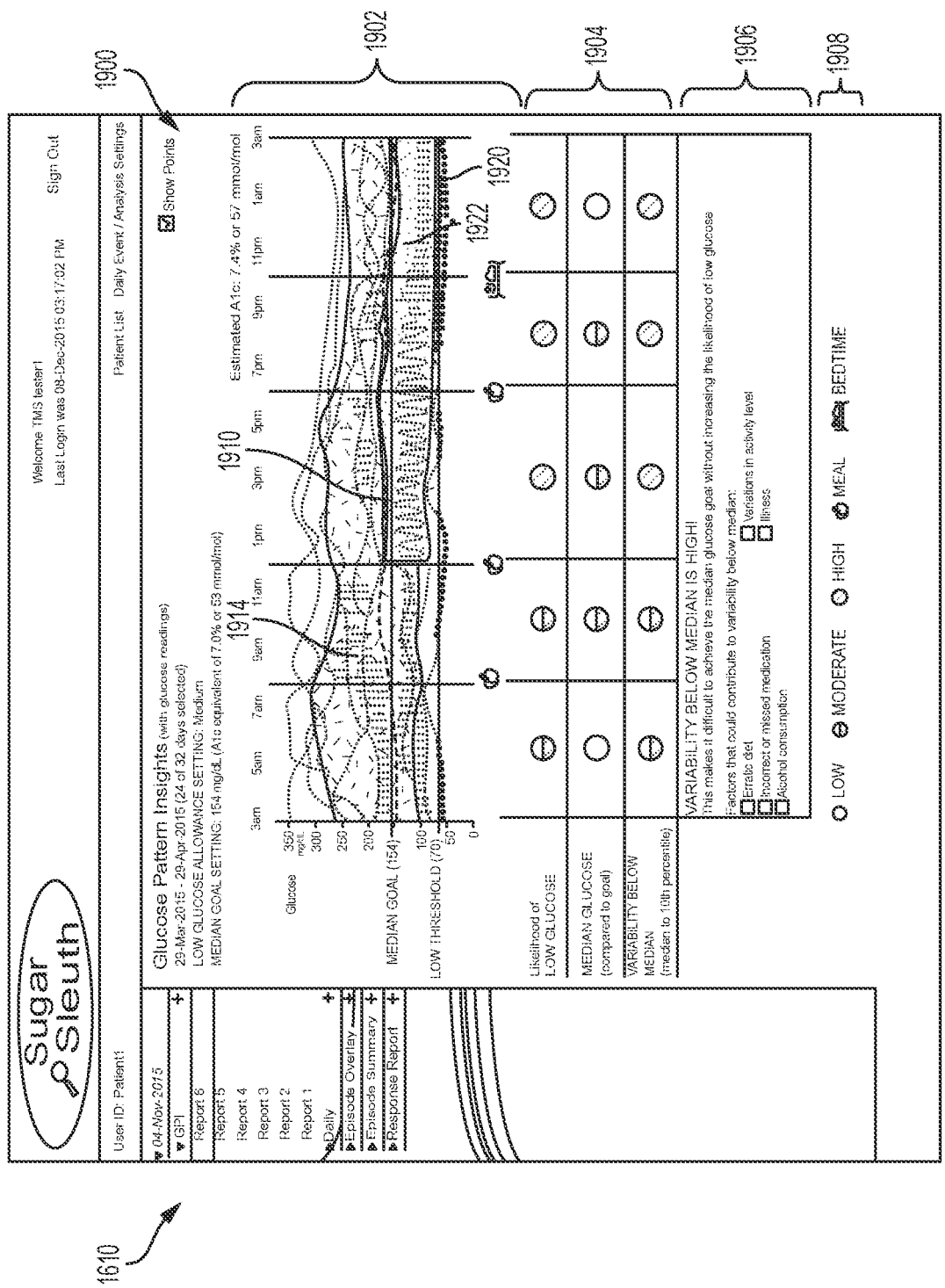

FIGS. 19A-B depict example embodiments of a GPI report 1900. Here, GPI report 1900 includes a first region 1902 that displays an ambulatory glucose profile (AGP) of the user and a second region 1904 that displays assessments of the severity of certain conditions related to the user's diabetes. Examples of GPI reports (referred to as an "Advanced Daily Patterns (ADP)" report) including the AGP are described in detail in US. Publ. No. 2014/0188400, which is incorporated by reference herein in its entirety for all purposes. In light of this incorporated description, the GPI report 1900 is described here in brief.

The AGP region 1902 can include a plot of glucose values for the selected days across a time scale of a typical day. A central tendency (e.g., a median or mean) 1910 is depicted with a trace. Surrounding this trace 1910 is a region 1912 that corresponds to the values of the data that are within a percentile range of the central tendency (e.g., the 25th percentile of data points to the 75th percentile of date points). Next to region 1912 is a second region 1914 that corresponds to the values of data that are within a wider percentile range of the central tendency (e.g., the 10th percentile of data points to the 90th percentile of date points). Regions 1912 and 1914 can be denoted in any desired fashion, such as with different lines, colors, or shadings, to name a few. These regions 1912 and 1914 can be solid or can show each data point as with the embodiment of FIG. 19B. Also shown in the AGP region 1902 is an indication of the user's central tendency goal (here a "median goal") and the user's low glucose threshold, which can be set and adjusted by the user (e.g., diabetic or HCP).

Region 1904 is a table with icons 1916 identifying the level of severity of the corresponding conditions for subsets of time throughout the typical day. Any number of one or more conditions can be listed and cross-referenced with any number of one or more icons corresponding to one or more periods of time during the day. In this example, there are three conditions listed vertically (e.g., along a Y-axis) that are the: (1) likelihood of low glucose (or hypoglycemia); (2) the median glucose value compared to the median glucose goal; and (3) the variability below the median (e.g., the difference in glucose value between the median and the bottom 10th percentile). For these conditions, a different central tendency, such as mean, can be used instead of the median.

In this example, the day is subdivided into five periods of time, which are not required to have equal lengths, but can be set by the user to correspond to the user's lifestyle (e.g., aligning with meals and bedtime). These periods of time can be aligned (e.g., can use the same time axis) as the AGP 1902 for ease of reference. The icons 1916 in the table can graphically represent the level of severity of the condition during that period of time as indicated by the key in region 1908.

In this example, the diabetic has experienced a variability below the median that is high according to the diabetic's goals set in the EIS, during the period of time from noon to 3 am. There is also a likelihood of low glucose that is high during this time.

Region 1906 can display a notification raising awareness of any one or more conditions that are high and can list potential causes for that high condition. Here, region 1906 displays a notification pertaining to the high variability below the median along with factors that could contribute to that condition.

FIG. 19B depicts another embodiment of GPI report 1900 where the same data of FIG. 19A is used, but depicted in a different fashion. Here, each data point in AGP region 1902 is depicted. Data points 1920 falling below the low threshold can be highlighted (e.g., colored as red). One or more of regions 1912 and 1914 can be omitted (here region 1914 is displayed but region 1912 is omitted). Additional highlighting or indication can be used to denote regions 1922 where one of the tracked conditions of region 1904 was determined to be high. Here, those points associated with a high variability below the median are denoted in the corresponding time range by shaded region 1922.

Figure 20:
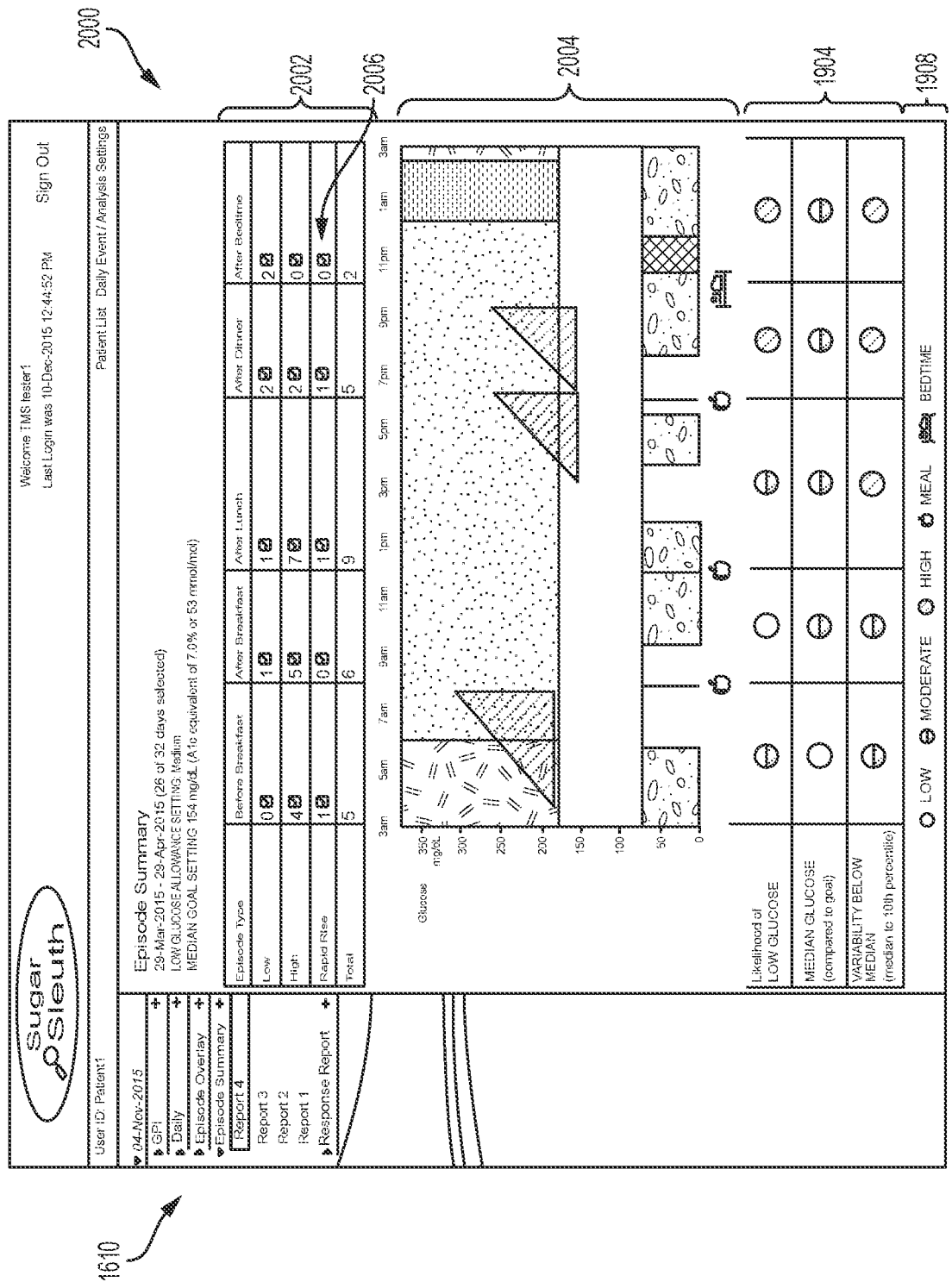

FIG. 20 depicts an example embodiment of an episode summary report 2000, which can assist in identifying episode patterns that may be repeating during a particular time of day. Here, episode summary report 2000 includes a modal day graph 2004 of glucose levels for each selected day over a predetermined period of time, for example, over the entire 24 hours. Also displayed within graph 2004 are markers for the placement and duration of episodes at their time of occurrence with the selected data set.

Episode summary report 2000 can also include a table 2002 that sets forth each episode type (e.g., low glucose, high glucose, rapid rise) along with the number of instances when that episode type occurred during a particular time of day (e.g., which can be the same time periods as depicted in the condition assessment region 1904, both of which can be aligned with the time axis of graph 2004). Total episode occurrences within each time period are also shown. This tabular display 2002 allows the user to readily understand patterns in episode type occurring against particular times of day. A selectable field 2006 (e.g., a checkbox) is present adjacent to each episode count. Selection of this field causes the markers for each episode of that type during that time period to be displayed (with checkbox checked) or hidden (with checkbox unchecked) within graph 2004, which can further assist the user in identifying patterns or times of day where certain episode types are most likely to occur.

In some embodiments of the EIS, an overnight summary report (not shown) can also be provided in a fashion similar to episode summary report 2000. The overnight summary report can differ in that the focus can be for a particular period of time, for example, the overnight period of time, whereas episode summary report 2000 can extend in most embodiments over a greater period of time, for example, over 24 hours. The overnight summary report can include one or more of a table that indicates the number of occurrences of each episode type or risk factor overnight, a plot of glucose level readings, and indicators for episodes and risk factors. Non-limiting examples of overnight low glucose risk factors can include a) bolus within 3 hours of bedtime, b) afternoon or evening physical activity, c) alcohol consumption. Non-limiting examples of overnight high glucose risk factors include a) high carb evening meal or snack, b) high fat evening meal or snack, c) ate out at restaurant.

Figure 21:
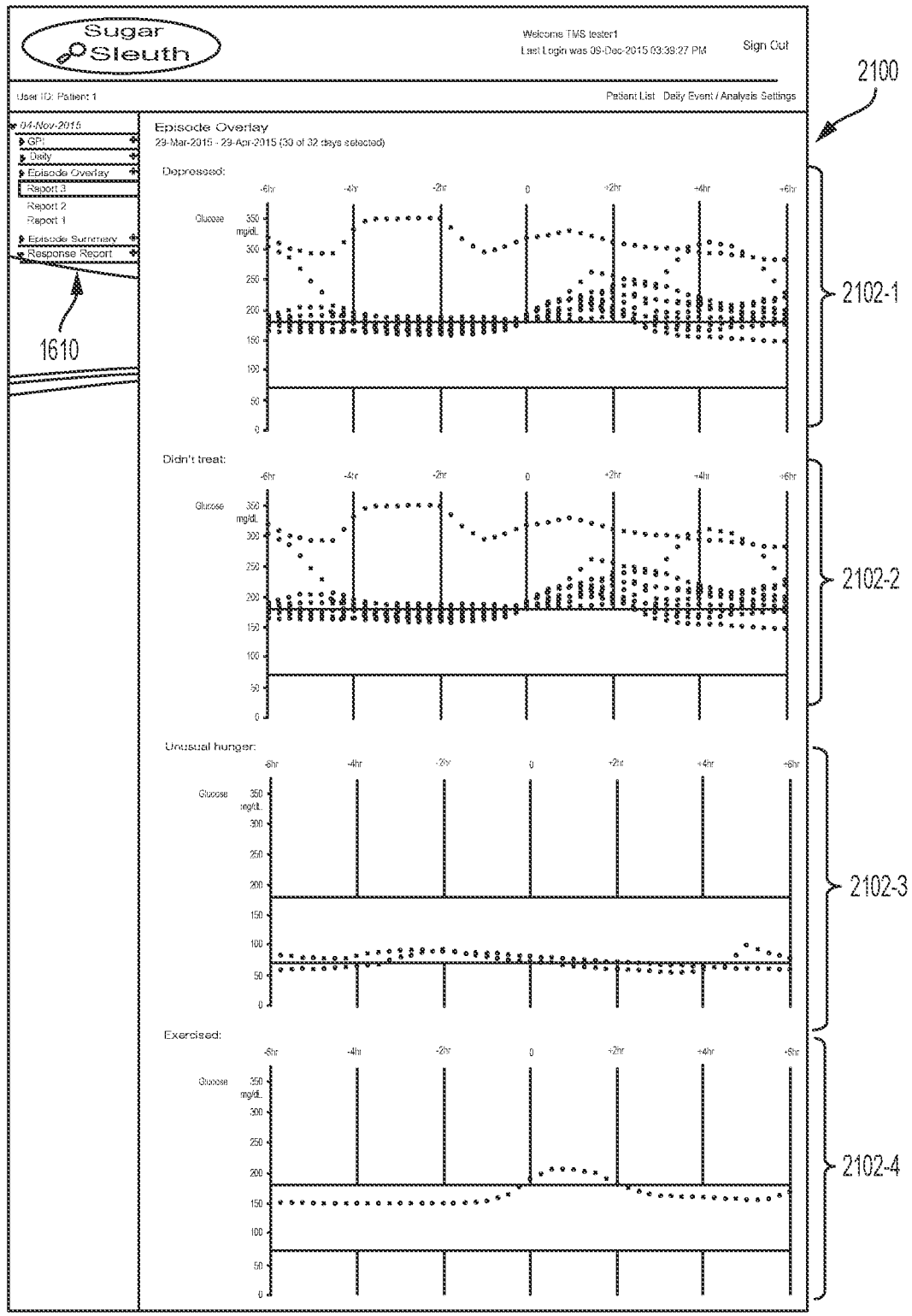

FIG. 21 depicts an example embodiment of an episode overlay report 2100. For each response that the patient identified in response to the questions asked when a particular episode was detected (see the discussion with respect to FIGS. 12A-C), an episode-aligned modal graph or plot 2102 of glucose level readings for every episode having that response identified can be displayed. Time of occurrence of each episode can be aligned at a central axis (e.g., 0 hours) and glucose level readings for a predetermined time period, for example, 1-12 hours, before and after that episode can be graphed or plotted. Episode overlay report 2100 assists in illustrating the effect on the user's glucose levels whenever a particular suspected cause results in an episode.

For example, for each episode detected within the selected date range, the user may have entered a suspected cause. A separate graph 2102 can be generated for each suspected cause, where the graph contains the glucose data associated with each episode where that suspected cause was identified. Although not shown here, graphs 2102 can be similarly generated for each symptom identified and for each treatment identified, or for any other response associated with a question posed about the episode.

In this embodiment, four graphs are shown: graph 2102-1 that includes glucose data for each episode to which the suspected cause "Depressed" was identified by the user; graph 2102-2 that includes glucose data for each episode to which the suspected cause "Didn't treat" was identified by the user; graph 2102-3 that includes glucose data for each episode to which the suspected cause "Unusual hunger" was identified by the user; and graph 2102-4 that includes glucose data for each episode to which the suspected cause "Exercised" was identified by the user (showing only one set of glucose data as only one such episode qualifies). The graphs 2102 can be arranged in sequential fashion where the response with the most qualifying episodes is listed at top and the response with the least number of qualifying episodes is listed at bottom.

Figure 22A:
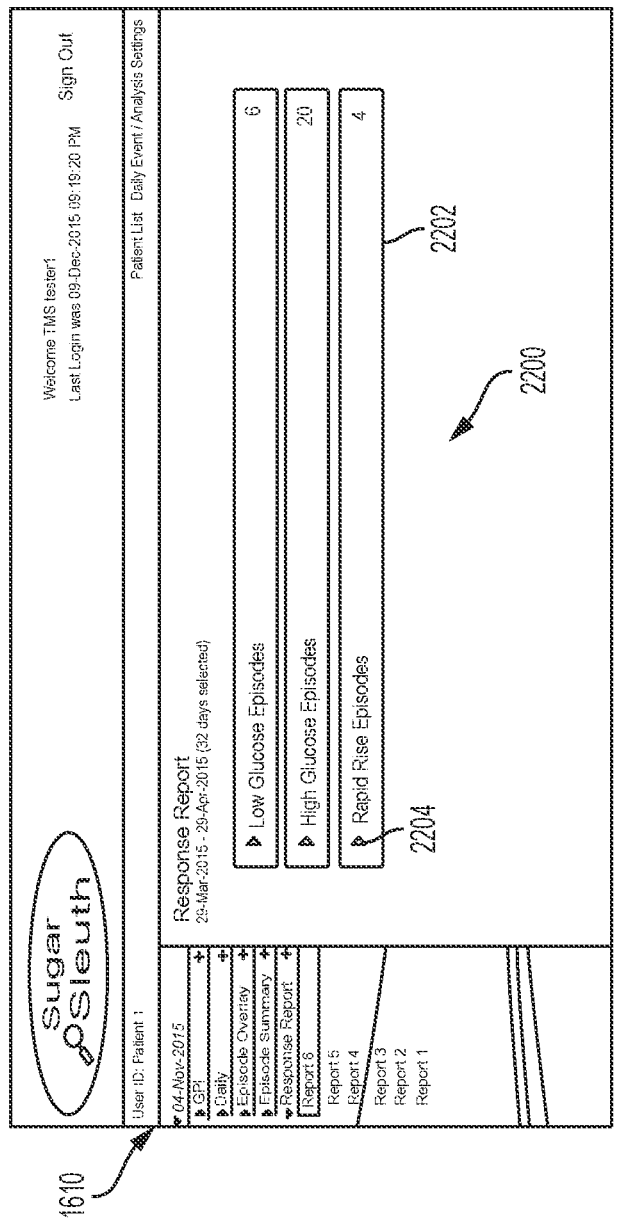
FIGS. 22C-D are flow diagrams depicting example methods performed by instructions implementing the episode investigative software.

FIG. 22A depicts an example embodiment of a response report 2200, which can assist the user in quickly identifying days of interest—that is, days where episodes have most frequently occurred. This report can assist (e.g., alleviate a perceived need by HCP's) in replacing the practice of searching through day-by-day to find problems; rather this report aggregates the episode responses recorded by the patient and highlights the responses-responses that represent self-care behavior problems that need to be addressed to reduce glucose variability—that occur the most frequently. In the example in the figure, "High Glucose Episodes" are shown to occur the most frequently. After selection of the date range, generation of response report 2200 can cause the display of an expandable summary 2202 of the number of responses recorded for each type of response associated with each type of episode. Selection of the expander field 2204 can cause the list to expand for the associated episode type.

Figure 22B:
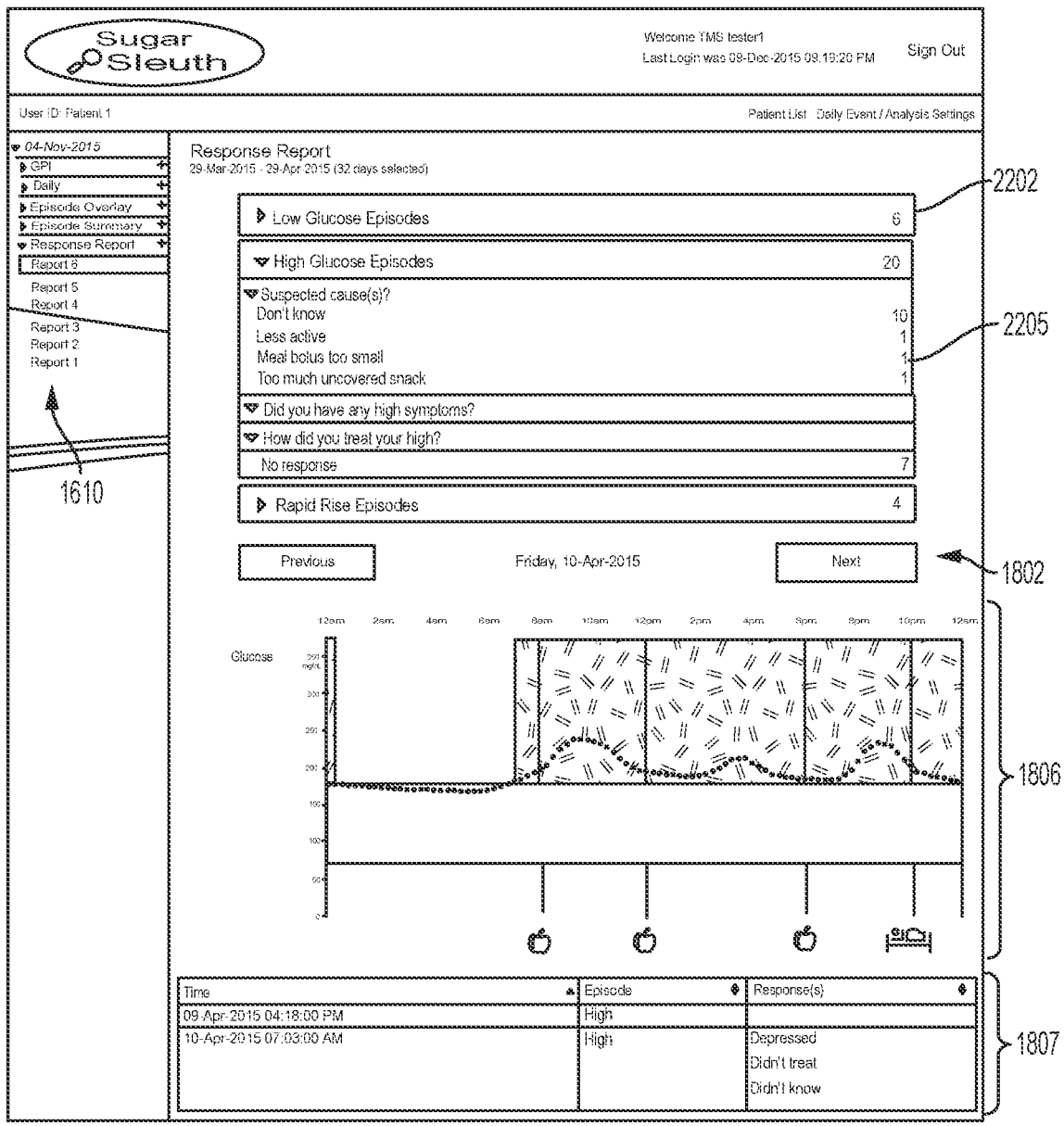

FIG. 22B depicts an example embodiment of response report 2200 after the high glucose episode type has been expanded. As seen here, a list of each question propounded to the diabetic in response to the detection of an episode type is displayed (e.g., those questions described with respect to FIGS. 12A-C). These lists can also be expandable such that expansion causes every response type given to the particular question to be displayed along with the number of instances that particular response was indicated. The responses can be ordered by descending number of instances to facilitate quick identification of the response or problem that occurs the most frequently, which is typically the problem that should be addressed first by the HCP and patient in order to maximize reduction in glucose variability. Selection of a particular response row 2205 can cause the display of one or both of a daily graph 1806 along with an episode table 1807. Other graph types can also be displayed. The displayed daily graph 1806 can be associated with, for example, the most recent day in the selected date range where that response type was actually indicated by the user. Selection of the next or previous buttons 1802 can advance to the next day or backtrack to the previous day where this response was actually indicated or provided by the user.

Report 2200 thus provides a mechanism where users can quickly identify the most frequent response or problem occurrence that needs to be addressed and drill down to (or identify) the particular days where the response or problem occurred. Users can then examine the more detailed information and glucose traces that are presented on an individual day-by-day and episode-by-episode basis and that are associated with this problem in order to understand what needs to be addressed.

Figure 22C:
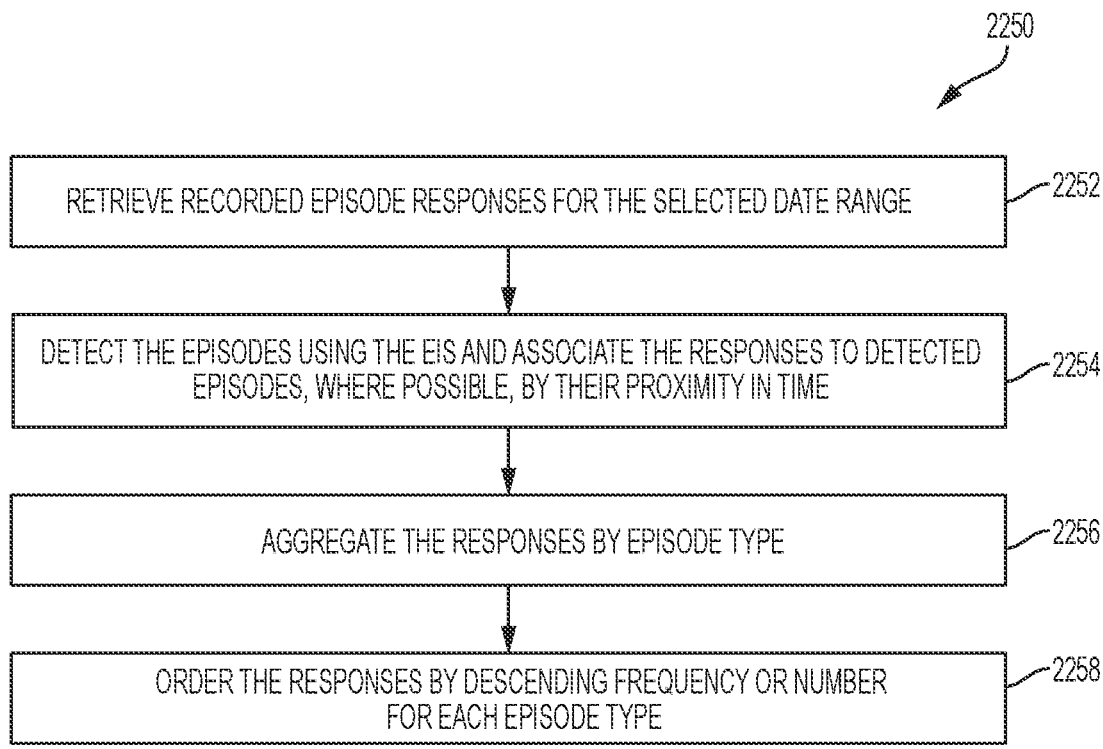

FIG. 22C is a flow diagram depicting an example method 2250 of the sequence of instructions, in a server-based version of the EIS, that can be used to develop report 2200. Note that the episode responses and corresponding date and/or time stamps can be uploaded automatically from reader 120 to server 130. In this embodiment, the episodes are detected using the EIS on server 130 instead of with the version of the EIS being executed on reader 120, and the detected episodes are associated to the episode responses by temporal proximity. This can have the advantage of simplifying the design of the EIS stored and executed by reader 120 in that the stored responses do not need to be associated with episodes and the association does not need to be communicated to server 130. (In an alternative embodiment, reader 120 can store and communicate the association between episodes and responses to server 130.)

Referring now to FIG. 22C, at 2252 the server's processing circuitry 131 (see FIG. 1A) retrieves recorded episode responses for the selected date range from the non-transitory memory 132 communicatively coupled with processing circuitry 131. At 2254, processing circuitry 131 can detect the episodes using the EIS and associate the responses to detected episodes, where possible, by their proximity in time (for example, if the first responses recorded after a detected episode are within a minimum threshold time then those responses are associated with that detected episode). At 2256, processing circuitry 131 can aggregate the responses by episode type. Then at 2258, for each episode type, processing circuitry 131 can order the responses by descending frequency or number.

Figure 22D:
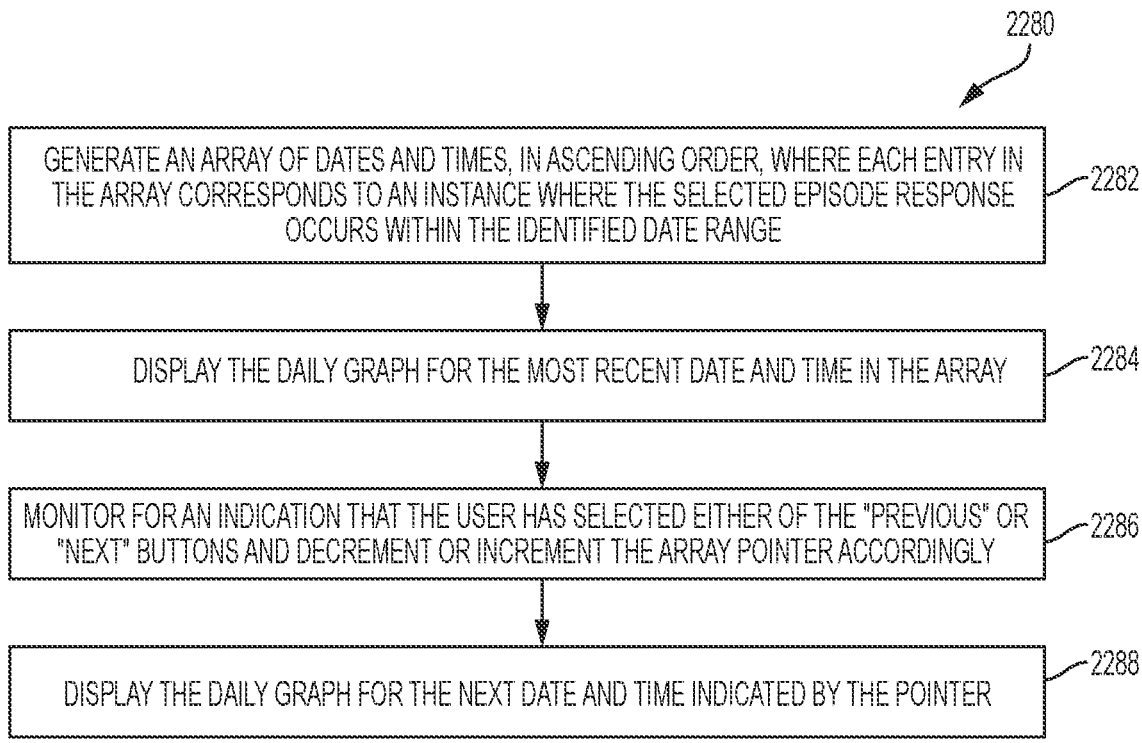

FIG. 22D is a flow diagram depicting an example method 2280 of the sequence of instructions, in the server-based version of the EIS, that can be used to generate the daily graph or report 1806 for a selected episode response. At 2282, processing circuitry 131 can generate an array of dates and times, in ascending order, where each entry in the array corresponds to an instance where the selected episode response occurs within the identified date range. At 2284, processing circuitry 131 can cause the display of daily graph 1806 (e.g., by supplying information for use in rendering the display with daily graph 1806) for the most recent date and time in the array.

At 2286, processing circuitry 131 can monitor for an indication that the user has selected either of the "previous" or "next" buttons 1802 and then decrement or increment the array pointer accordingly. The "previous" button or the "next" button may not be available for selection on the display if the pointer is at the beginning or end of the array, e.g., if there is no date earlier than the date of the information in the presently displayed graph 1806, then the "previous" button will not be available for selection, and if there is no date later than that of the present graph 1806 then the "next" button will not be available. At 2288, processing circuitry 131 can cause the display of the daily graph 1806 for the date and time indicated by the pointer.

If interactive episode filter 1810 is displayed with daily graph 1806, then processing circuitry 131 determines and the positions markers 1812 and 1814 to be on opposite sides of the time of occurrence of the episode, in order to highlight that episode. For instance, left marker 1812 can be located a predetermined time (e.g., one hour) before the time of occurrence of the episode and right marker 1814 can be located the same or a different predetermined time (e.g., three hours) after the start of the episode, adjusted to the nearest clock hour increment.

Figure 23:
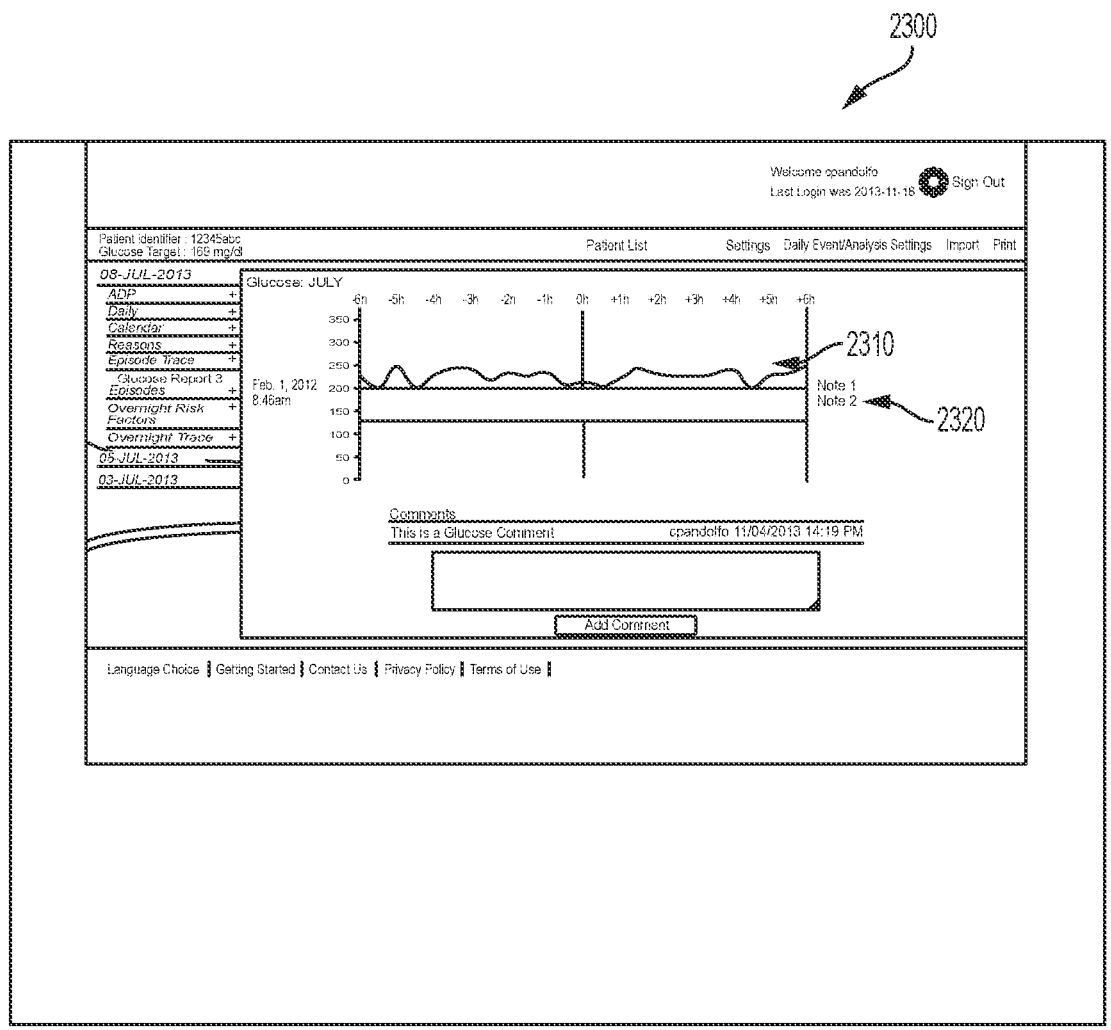
FIGS. 23-24 are diagrams depicting example embodiments of graphical user interface screens that can be displayed on the display of a computing device executing or accessing an example embodiment of the episode investigative software.

FIG. 23 depicts an example embodiment of an episode trace report 2300. For each episode, a plot 2310 of glucose level readings can be displayed with the episode centered at 0 hours. The plot of glucose levels can span a predetermined time period, for example 6 hours before the episode and 6 hours after the episode. Report 2300 also can display one or more of patient reported episode reasons, symptoms, treatments, and notes 2320 associated with the episode. Report 2300 can allow detailed review of a particular episode.

Figure 24:
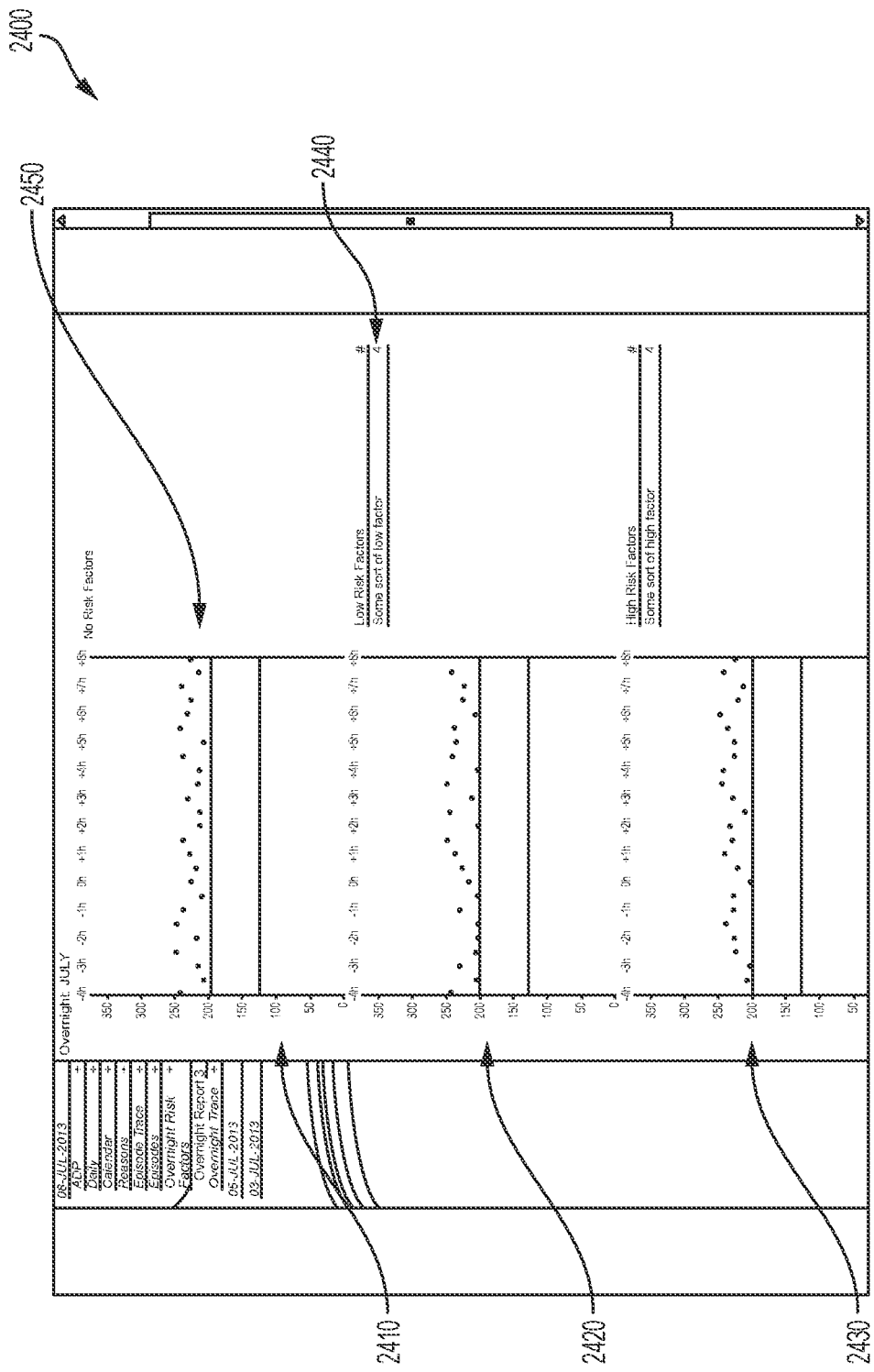

FIG. 24 depicts an example embodiment of an overnight risk factors report 2400, which can include one or more of plots of modal glucose levels 2450 associated with no risk factors 2410, high glucose risk factors 2420, and low glucose risk factors 2430. Each plot of modal glucose levels 2450 can include a tabulation of the number of each type of risk factor 2440.

The reports described herein are merely examples. Embodiments of the EIS can include any combination of some or all of the reports described herein. Embodiments of the EIS can include different reports in addition to, or instead of, those reports described herein. Furthermore, it is stressed that the various fields, data arrangements, icons, notes, markers, and indicators of each graph, table, and/or report described herein can be freely substituted in each and every other embodiment of a graph, table, and/or report described herein, unless stated otherwise or logically implausible.

The local and remote computers 150 and 160 can perform some or all of the functions of reader device 120 and/or network server 130. For example, the local computer 150 can perform episode detection on glucose level readings and prompt the patient for responses to detected episodes. The episode detection algorithm on the local computer 150 can include a configuration to search for all episodes, similar to that of server 130, or a subset of episodes, similar to the glucose monitoring application on reader device 120.

Figure 25:
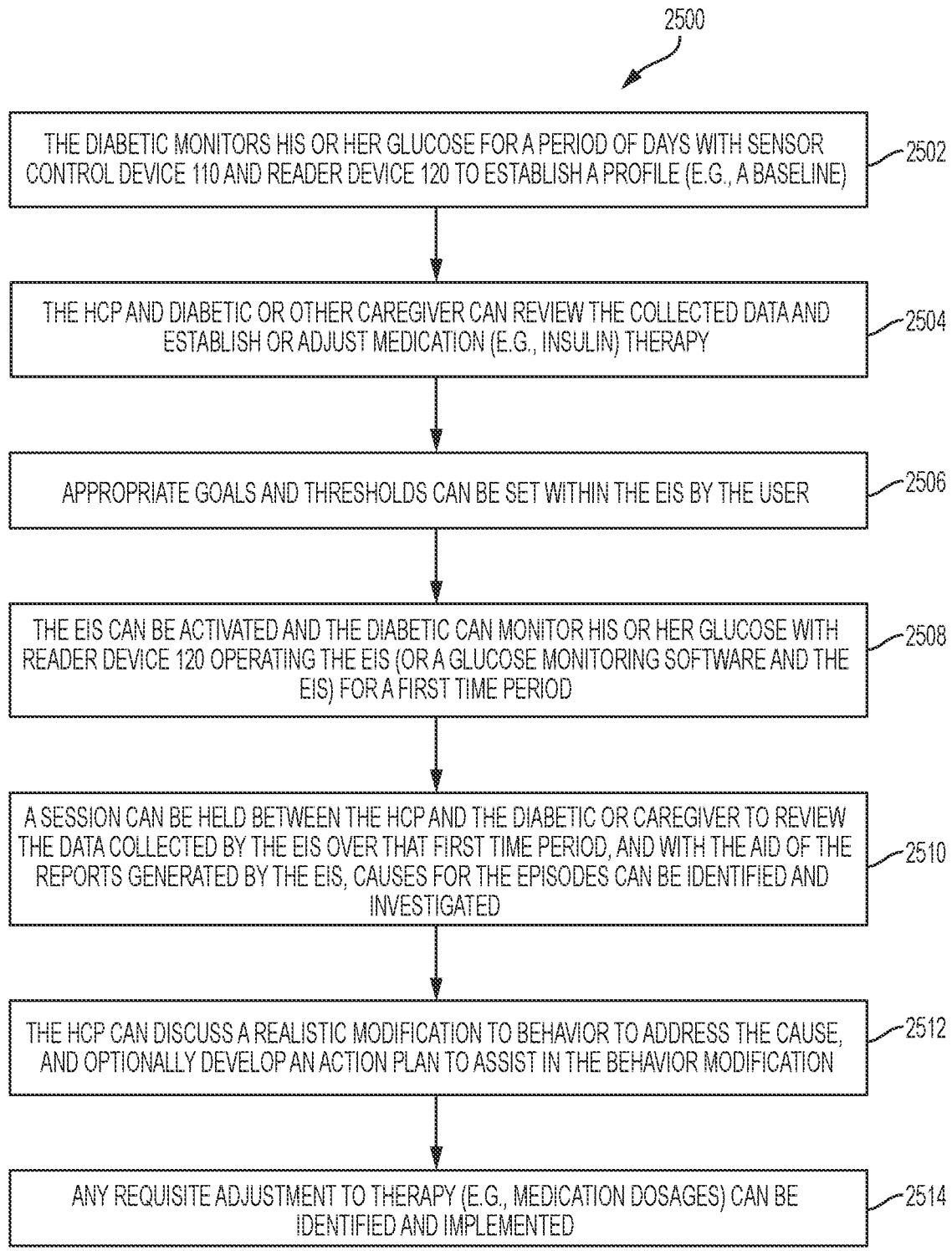
FIG. 25 is a flow diagram depicting an example embodiment of a method of treatment of a patient with the assistance of the episode investigative software.

FIG. 25 is a flow chart depicting an example embodiment 2500 of using the EIS. At 2502, the diabetic monitors his or her glucose for a period of days (e.g., 7 days or 14 days) with sensor control device 110 and reader device 120, which can be operating with a masked glucose monitoring software or a masked embodiment of the EIS. This collected data can be used to establish a baseline glucose behavior profile for the diabetic.

At 2504, the HCP and diabetic or other caregiver can review the collected data and establish or adjust medication (e.g., insulin) therapy, such as with the aid of a GPI report 1900. At 2506, appropriate goals and thresholds can be set within the EIS by the user (the HCP, caregiver, or diabetic) to enable the production of the various reports (e.g., a median threshold goal in the GPI report) and to detect episodes and excursions (e.g., low glucose threshold, high glucose threshold, rapid rise threshold, to name a few). At 2508, the EIS can be activated and the diabetic can monitor his or her glucose with reader device 120 operating the EIS (or a glucose monitoring software and the EIS) for a first time period (e.g., a number of days or weeks). The EIS can be set to operate at only certain times of the day, such as those that have shown to be problematic in the baseline data.

At 2510, a session can be held between the HCP and the diabetic or caregiver to review the data collected by the EIS over that first time period. This can include review of one or more reports capable of generation by the EIS. For example, the episode response report 2200 can be generated and the most frequent episode cause or causes can be identified. The daily graphs 1806 within the episode response report 2200 can be then be used to identify the specific underlying behavior causing the episodes. Other reports can be utilized based on the specific situation.

At 2512, the HCP can discuss a realistic modification to behavior to address the cause, and optionally develop an action plan to assist in the behavior modification. At 2514, any requisite adjustment to medication therapy can be identified and implemented, for example, with the assistance of the GPI report 1900. This process can be repeated as necessary until the diabetic's variability levels and/or excursions are reduced to the desired levels.

The episode investigate software has been described herein in the context of an analyte monitoring system, with particular applicability to the monitoring of glucose to assist diabetics in managing their condition. However, functionality, attributes, reports, and other features of the episode investigative software have broader applicability to the as well, including to the management of other types of medical conditions and even to applications outside of the medical field.

For example, the subject matter disclosed herein is not limited to investigating the causes of episodes, but can be used to monitor and characterize other attributes, conditions, or characteristics of a person that may or may not qualify as an episode as that term is used in its broadest scope herein. The data collected and analyzed can be of virtually any type, such as activity related data (e.g., steps taken, calories burned, etc. as tracked and reported by devices such as an activity monitor), meal information, location information (e.g., with a GPS-enabled device), other forms of biometric data such as characteristics of the heart and/or vascular system (e.g., heart rate, blood pressure, heart sounds, etc.), characteristics of other organs such as the eye (e.g., intraocular pressure), skin (e.g., perspiration), brain (e.g., neuro-electrical activity), and others. This collected data can be compared to one or more rules, conditions, requirements, thresholds, etc., that are indicative of the occurrence of an episode, event, characteristic, symptom, precursor, activity, etc. that is relevant to the particular application.

Example Embodiments of Software Using Decorator Patterns and/or Dependency Injection for Robust Library Construction or Modification The following embodiments can be implemented as a part of a software application operating on reader device 120 within system 100 as described herein. Reader devices and analyte monitoring systems are also described in U.S. Publication Nos. 2015/0205947 and 2015/0341438, both of which are incorporated by reference herein in their entirety and for all purposes. The embodiments described in this section, like all embodiments herein, can be used with any and all analyte monitoring systems described in these incorporated references, including any system with in vivo capability, in vitro capability, or combination of the two.

Also like the aforementioned embodiments, the embodiments of this section are not limited to use only on a reader device 120 within system 100, and can be used on a broad range of other electronic computing devices that have processing circuitry and non-transitory memory (such as that processing circuitry and memory described herein). Furthermore, the following example embodiments are not limited to use within a medical analyte monitoring environment. Instead, these embodiments have broad applicability and can be used within any environment, device, and/or system, regardless of whether that environment, device, and/or system is medical-related, not medical-related, or otherwise.

These and all software embodiments described herein can be implemented through one or more instructions stored in a memory. Those instructions, when executed by processing circuitry, can cause that processing circuitry to perform or cause to be performed the functions and/or actions described herein.

For ease of description, the example embodiments will be conveyed herein by reference to a downloadable software application being executed on a reader device 120 in the form of a mobile communication device (e.g., a smartphone). Example embodiments of smartphone reader devices 120 and analyte monitoring systems 100 are described herein.

In certain example embodiments, the software application is an analyte monitoring application that can have a sensor interface module (or application) for enabling and controlling communication with a sensor control device 110. This sensor interface module can generate, encode, and/or encrypt a communication request to be transmitted to the sensor control device 110 requesting that the analyte information collected from the wearer of sensor control device 110 be transmitted to reader device 120. This module can also decrypt, decode, and/or read the received information from sensor control device 110. In some embodiments, the received data from sensor control device 110 will be raw data in digital form representing the converted analog measurements from sensor 104, or will be in a partially processed digital form where a degree of filtering, temperature calibration, sensor calibration, error checking, or other processing has been applied to the raw data. This sensor interface module can be responsible for further processing the received data to apply these and more extensive forms of filtering, calibration, and/or algorithmic processing for converting the received data into a reliable representation of the user's analyte level that can be output to the user interface in a format for display to the user.

The analyte monitoring application can also include a user interface module (or application) that is responsible for interface with the user of reader device 120. This user interface module can select and control the information displayed on display 121 of reader 120, such as causing a home screen to be displayed and causing the display to change from a first screen to a second screen depending on, e.g., the inputs received by the user.

This user interface can cause the display of graphs, numerical values, trend arrows, and other indicia to be displayed on display 121 that convey analyte information about the user, that analyte information being current information (e.g., within the last hour) and/or historical information (e.g., within a plurality of days, weeks, or months). This user interface module can also cause menus, options, settings, and other user selectable fields to the user to be displayed on reader device 120, and can process user selections received through user input component 122.

Generally, when a user inputs a command that is received by the user interface module, that module forwards an instruction, or call, or otherwise passes the information to the sensor interface module to implement that instruction. In some embodiments, the call or information pass may be done by calling a specialized function or by way of an Application Programming Interface (API), either of which can be called from the software library. These functions and/or APIs can interface with the operating system (OS), the device drives, the hardware, and other aspects of the phone.

Similarly, when the sensor interface module, in carrying out its programming, seeks to have an instruction executed or a function carried out, then that sensor interface module will forward the instruction, or call, or otherwise pass the information to another module or application that will assist in carrying out the desired instruction. This process can continue from the highest relative programming layer (e.g., the application layer) involved in carrying out the instruction down to relatively lower layers of programming (e.g., the application model, the user interface (UI) model, cloud integration, the kernel, the device drivers (software that enables operation with a particular hardware component or card), the hardware board support package (BSP), and others.

In these example embodiments, the various interfaces between modules, functions, objects, and the like are exposed to the application layer such that the information (e.g., data, values, null fields, instructions, or otherwise) passed by the interfaces between modules, functions, objects, and the like can be altered or modified. In some embodiments, the modification entails the injection of new information into the software at the interface, while in other embodiments, the modification entails the removal or deletion of information passed by the interfaces, and in still other embodiments, the modification can include the altering of certain information, the addition of certain information, and the deletion of certain information, and any combination thereof. By exposing these interfaces, the application layer (e.g., the analyte monitoring application) can control what information is exchanged through or by the interfaces without altering the core instructions of the various modules, functions, or objects responsible for processing, determining, or retrieving that data to be passed.

The example embodiments described herein can be implemented such that the library accepts a wrapper for an interface that is provided by the downloadable software application. These wrappers can be direct forwarding calls to a pre-existing module or function in which no modification is desired. Thus, in the source code of the downloadable software application, any interface code that the software designer wants control over can be provided with a wrapper. If no control is desired or necessary at a particular time, then the wrapper can consist of only a forwarding call to the particular module or function. The library accepts the wrapper as a constructor parameter passed by the overall application.

However, if the information passed by the interface code requires modification, then a decorator or decorator pattern can be added to the wrapper to perform the modification. This can be useful in a number of instances. For example, if a combination of hardware, device drivers, and/or operating system has an issue that causes the OS functions to function incorrectly or in an unintended manner, the software library can receive erroneous inputs and produce erroneous outputs. This might be discovered, for example, during testing of the overall application on multiple hardware combinations. If a software module or function is outputting erroneous information, then a decorator can be created for the wrapper to the interface that passes the erroneous result from that software module or function, for example, an OS error propagated into the library. This decorator can detect the presence of the erroneous error and modify it as appropriate, either by deleting it, altering it, replacing it with one or more null or ignore values, or otherwise.

Thus, in this example, the application can be modified to identify and correct software problems without modifying the pre-existing module or function in the library. In some cases, those pre-existing modules or functions can be complex software entities that are not easily revised. For example, the pre-existing module or function may be written by another design team or vendor, or the pre-existing module of function may be subject to a design freeze or other administrative classification inhibiting modification, or in some examples the pre-existing module or function may be a standard software unit that is functioning as it is designed to, but produces an output (e.g., containing null fields) that inhibit the operation of other software modules calling it.

The following embodiment is an example of a JAVA source code excerpt implementing a wrapper for a function that returns the current date in a year-month-day format.

```
interface OsFunctionWrapper {
    int getCurrentYear( );
    int getCurrentMonth( );
    int getCurrentDay( );
}
class DefaultOsFunctionWrapper implements OsFunctionWrapper {
    int getCurrent Year( ) {
        return OS.getCurrentYear( );
    }
    int getCurrentMonth( ) {
        return OS.getCurrentMonth( );
    }
    int getCurrentDay( ) {
        return OS.getCurrentDay( );
    }
}
class DateLibrary {
    OsFunctionWrapper wrapper
```

```
  DateLibrary(OsFunctionWrapper wrapper) {
    this.wrapper = wrapper;
  }
  String getCurrentDate( ) {
    return String.format(
      "%d-%d-%d",
      wrapper.getCurrentYear( ),
      wrapper.getCurrentMonth( ),
      wrapper.getCurrentDay( ))
  }
}
int main( ) {
  DateLibrary lib = new DateLibrary(new DefaultOsFunctionWrapper());
  puts(lib.getCurrentDate( ));
}
```

If it is discovered during testing that some OS versions generate an incomplete output in that OS.getCurrentYear( ) returns only a two-digit year (e.g., 15 instead of 2015). This incomplete output could be completed without modifying the library by inserting a decorator that detects the issue and corrects it, as shown in the following code excerpt.

```
class YearFixOsFunctionWrapper implements OsFunctionWrapper {
  OsFunctionWrapper inner;
  YearFixOsFunctionWrapper(OsFunctionWrapper inner) {
    this.inner = inner;
  }
  int getCurrent Year( ) {
    int retVal = inner.getCurrentYear( );
    if (retVal < 100) {
      retVal += 2000;
    }
    return retVal;
  }
  int getCurrentMonth( ) {
    return inner.getCurrentMonth( );
  }
  int getCurrentDay( ) {
    return inner.getCurrentDay( );
  }
}
int main( ) {
  DateLibrary lib = new DateLibrary(new YearFixOsFunctionWrapper
(new
DefaultOsFunction Wrapper( ));
  puts(lib.getCurrentDate( ));
}
```

Thus, the wrapper (YearFixOsFunctionWrapper) in the example above for the interface code is capable of detecting the presence of the incomplete output (e.g., the returned year value being less than 100) and then apply the appropriate modification to complete it (e.g., adding 2000 to the year value).

Figure 26:
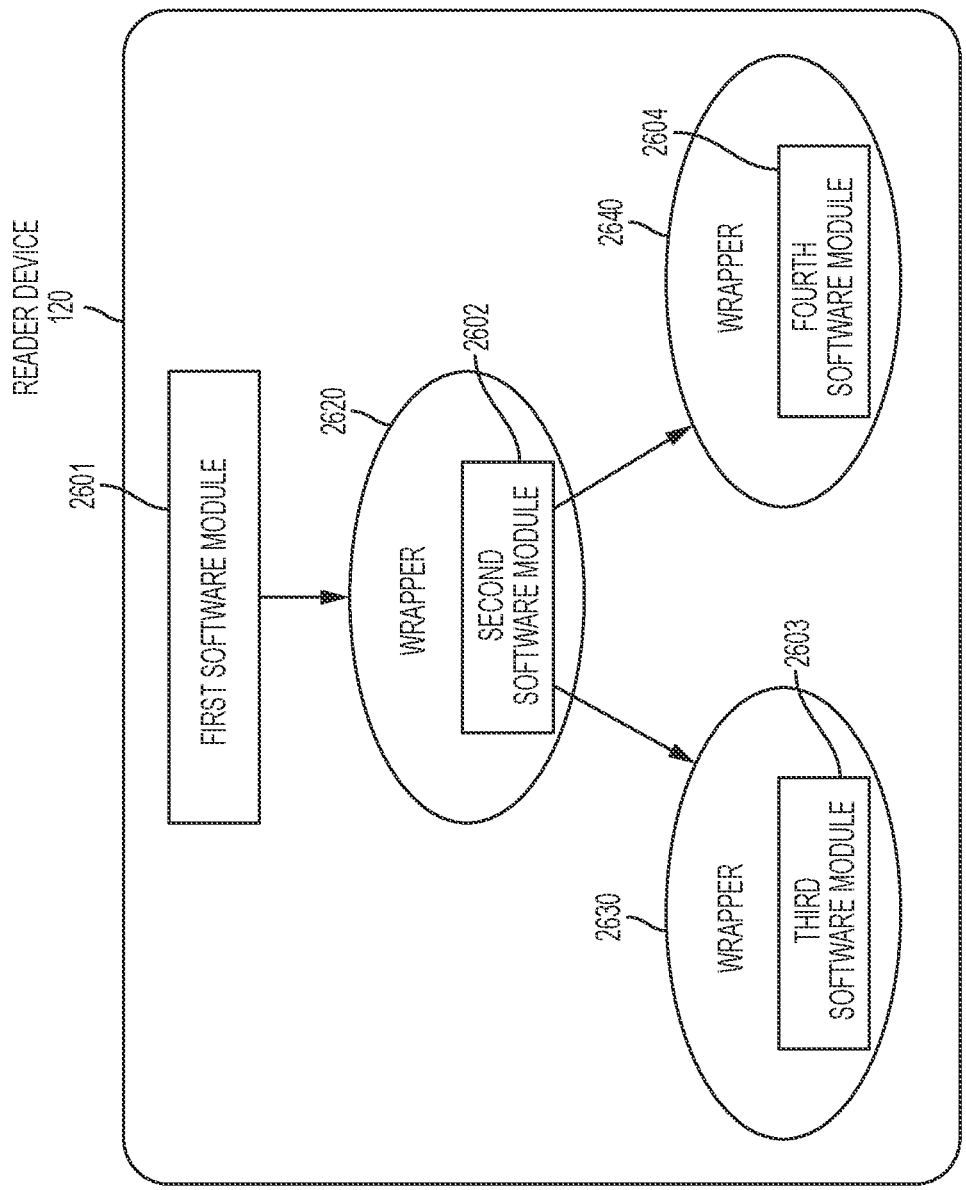
FIG. 26 is a block diagram depicting an example embodiment of software stored on a non-transitory memory of a reader device.

FIG. 26 is a block diagram figuratively depicting software operating on reader device 120. Here, a first software module (or function) 2601 indirectly calls a second, pre-existing software module 2602 by directly calling a wrapper 2620 for that second software module 2602. In some embodiments, the second software module 2602 can accomplish its task without calling other modules or functions. In this embodiment, to accomplish its task, second software module 2602 indirectly calls a third software module 2603 by directly calling wrapper 2630, and second software module 2602 indirectly calls a fourth software module 2604 by directly calling wrapper 2640.

In this embodiment, the information passed (e.g., a result returned) from third software module 2603 back to second software module 2602 is done so via wrapper 2630, which can be configured to determine if the result satisfies one or more conditions (e.g., designed to identify an erroneous, incomplete, or otherwise undesirable result) and modify that result (e.g., change, delete, append, etc.) to rectify the detected condition and then pass the modified result back to second software module 2602. If the condition is not satisfied, then the result can remain unchanged.

It is noted that satisfaction of the condition is relative to whether that condition detects the need for the modification or the absence of that need. In this embodiment, the condition identifies information to be modified, but the embodiments herein can operate such that the condition identifies information that does not require modification, in which case modification occurs when the information fails to satisfy (or violates) the condition.

Wrapper 2640 can operate in an analogous fashion on the information passed from fourth software module 2604 to identify whether that information satisfies one or more conditions and, if so, modify the result appropriately before passing to second software module 2602. Second software module 2602 can then use the information passed from wrappers 2630 and 2640, each of which may or may not be modified depending on whether the respective conditions for modification were satisfied, to perform its function and produce the information to be passed to first software module 2601. Wrapper 2620 evaluates whether the information passed from second software module 2602 satisfies a condition for modification, in which case it is modified and then passed to first software application 2601.

Thus, FIG. 26 assists in depicting the extensive degree to which wrappers can be utilized in the embodiments described herein. Wrappers can effectively be used any time one software module or function passes information (e.g., data, values, characters, software instructions, etc.) to another module or function.

Figure 27:
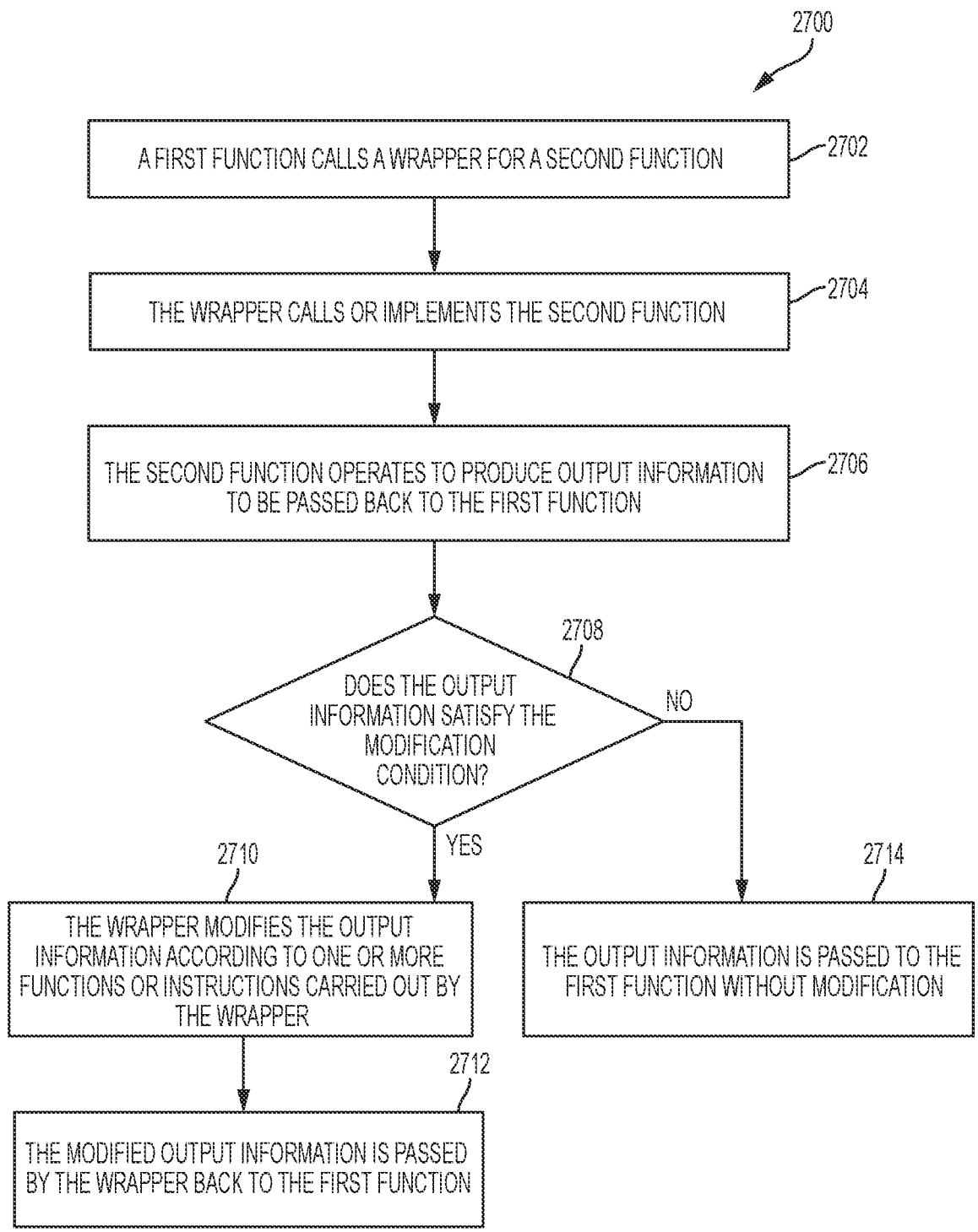
FIGS. 27-28 are flow diagrams depicting example embodiments of methods for operating software with a wrapper.

FIG. 27 is a flow diagram depicting an example embodiment of a method 2700 for operating a reader device 120 in an analyte monitoring system 100, where method 2700 utilizes the existence of a software wrapper to execute a task. At 2702, a first function calls a wrapper for a second function to execute the task. At 2704, the wrapper calls or implements the second function. At 2706, the second function operates to execute the task and produce output information to be passed back to the first function. At 2708, the wrapper determines whether the output information produced by the second function satisfies (or alternatively violates) one or more conditions that detect whether a modification of the information is appropriate. At 2710, if the condition is satisfied, then a modification is appropriate, and the wrapper modifies the output information according to one or more functions or instructions carried out by the wrapper. At 2712, the modified output information is passed by the wrapper back to the first function.

Alternatively, if the condition for modification is not satisfied, then at 2714 the output information is passed to the first function without modification. Method 2700 can be carried out any number of times based on the number of software modules or functions that are required to execute the particular task or tasks. Furthermore, each wrapper can be used to detect multiple conditions and provide multiple modifications correcting for the detected conditions. For example, each wrapper can implement any number of IF-THEN statements, or IF-THEN-ELSE statements, and multiple levels of conditional programming to accomplish the desired information modification function for that wrapper.

Figure 28:
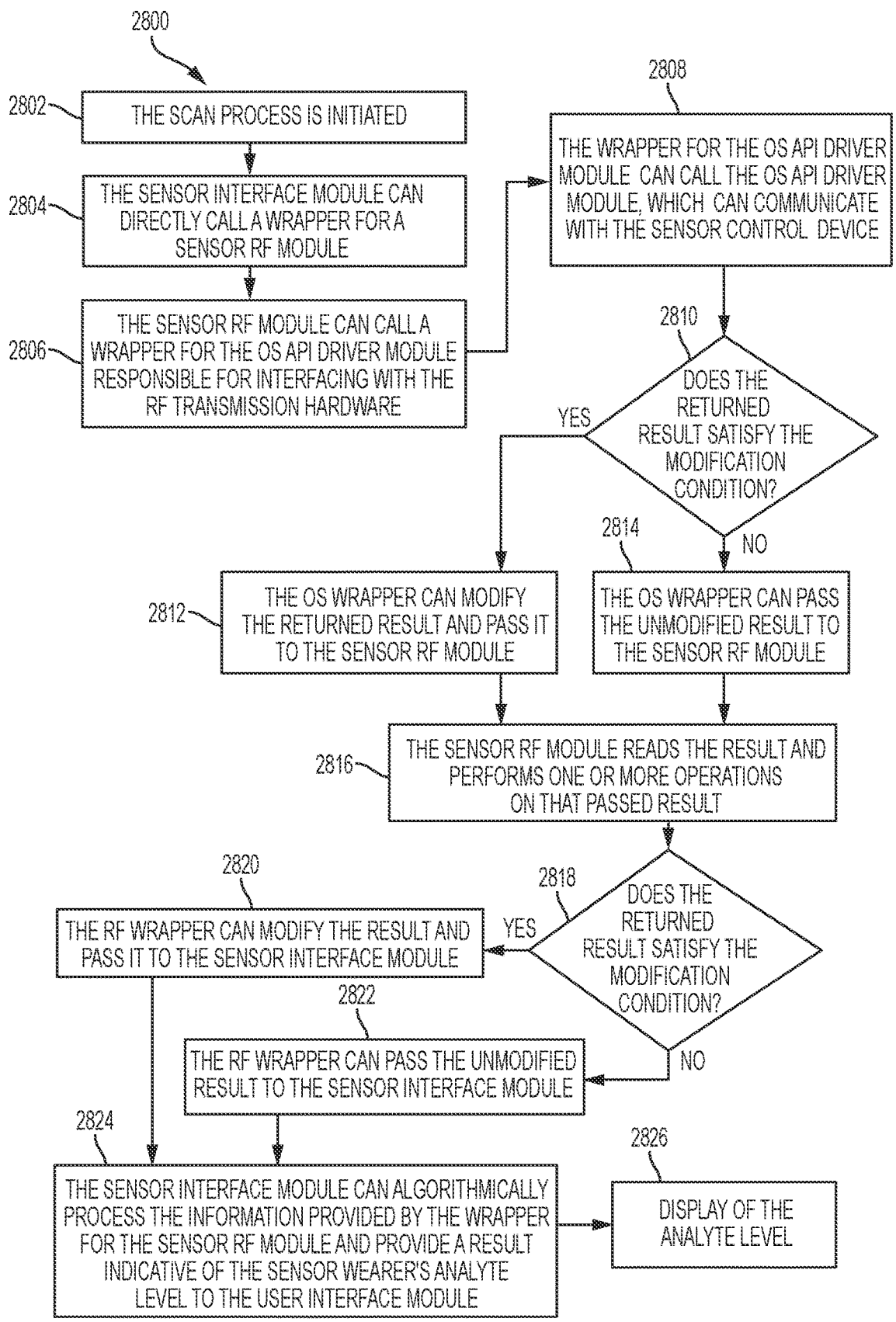

FIG. 28 is a flow diagram depicting an example embodiment of a method 2800 for utilizing reader device 120 to perform a read or a scan or a sensor control device 110 with software functions that utilize one or more wrappers. In this embodiment, reader device 120 is a smartphone executing a downloaded analyte monitoring application having a user interface module and a sensor interface module. At 2802, the scan process is initiated. This can occur, for example, by the user making a selection on a touchscreen display 121 indicating the desire to perform a scan. (During testing, this step can be bypassed with the software.) The user interface module can recognize this input and call the sensor interface module to initiate the scan.

At 2804, the sensor interface module can directly call a wrapper for a sensor RF module. The sensor RF module can be responsible for generating the bit sequence for transmission to the sensor control device 110. At 2806, the sensor RF module can then call a wrapper for the OS API driver module (or plural wrappers for plural modules) responsible for interfacing directly (or indirectly) with the RF transmission hardware (e.g., NFC, Bluetooth, BTLE, etc.).

In this manner, both the interface between the sensor interface module and sensor RF module as well as the interface between the sensor RF module and the OS API driver module are exposed to the application layer of reader device 120. The wrappers at these interfaces can be used for numerous purposes to assist in testing and/or operation of the analyte monitoring application.

At 2808, the wrapper for the OS API driver module can call the OS API driver module, which causes a request to be transmitted to sensor control device 110. The response received from sensor control device 110 is, after demodulation and/or decoding, etc., the result returned from the OS API driver module to its wrapper. At 2810, the wrapper for the OS API driver module can determine if the returned result satisfies a condition for modification, and if so, then at 2812 the wrapper can modify the returned result accordingly and pass it to the sensor RF module. Alternatively, if the condition for modification is not satisfied then at 2814 the result returned from the OS API driver module is passed through in unmodified form to the sensor RF module.

At 2816, the sensor RF module reads the result passed to it and performs the sensor RF module's one or more operations on that passed result. For all embodiments described herein, the performance of a module or function can include the performance of one or more operations on the information provided to that module or function, where those operations can include the performance of a mathematical operation on the information, the formatting of the information, the storing of the information in memory or a buffer, the calling of one or more other functions or modules, and/or other software operations known to those of ordinary skill in the art, and combinations thereof. After the sensor RF module has completed its operations, it returns a result to the wrapper for the sensor RF module.

At 2818, the wrapper for the sensor RF module can determine if the returned result satisfies a condition for modification, and if so, then at 2820 the wrapper can modify the returned result accordingly and pass it to the sensor interface module. Alternatively, if the condition for modification is not satisfied then at 2822 the result returned from the sensor RF module is passed through in unmodified form to the sensor interface module. At 2824, the sensor interface module can algorithmically process the information provided by the wrapper for the sensor RF module and provide a result indicative of the sensor wearer's analyte level to the user interface module in a format that is displayable or capable of rendering on the display such that it can be read and understood by the user. Display of the analyte level can occur at 2826.

Method 2800 and other such embodiments can be used in an almost limitless number of situations where control over the information passed between modules or functions is desirable. For example, the embodiments described herein can be used to modify information produced by the OS of reader device 120 (e.g., smart phone). If a low-level error checking routine fails, then the smartphone OS API drivers can be prone to produce incomplete responses. In one example embodiment, the wrapper for the OS API driver can detect these incomplete responses and add characters as appropriate to complete them.

In addition (or alternatively), the wrapper for the OS API driver can detect an incomplete response and generate an error. Thus, the wrappers utilized in the present embodiments are not limited to the modification of information passed between modules, but can also be used to raise errors, notifications, interrupts, or other flags within the software application while leaving the information passed between modules intact (if desired).

In other embodiments, one or more wrappers can be used to facilitate testing or simulating of the analyte monitoring application by inserting fixed data sets using the wrappers. For example, the wrapper for the sensor RF module could be configured to return fixed information instead of calling other functions. In some embodiments, this wrapper can be added to the analyte monitoring application at run-time, i.e., after the application has been compiled and when the analyte monitoring application is ready to be executed, or while being executed. This fixed information can be data that simulates an edge case scenario, such as a scenario that is very difficult to trigger using the actual hardware and the actual software routines. The triggering of low-level errors (e.g., errors emanating from the software drivers for the hardware components) can be examples of such edge case scenarios. The fixed data coming from the wrapper can propagate to the other software functions of the analyte monitoring application and thereby simulate the effects of those edge case scenarios on the analyte monitoring application (e.g., the sensor interface module and the user interface module, etc.) to assist in debugging and verification of the software as a whole. For example, the processing circuitry (or a software developer or the like) can determine whether an addition error is generated as the fixed data propagates to other software functions.

Computer program instructions for carrying out operations in accordance with the described subject matter may be written in any combination of one or more programming languages, including an object oriented programming language such as Java, JavaScript, Smalltalk, C++, C#, Transact-SQL, XML, PHP or the like and conventional procedural programming languages, such as the "C" programming language or similar programming languages. The program instructions may execute entirely on the user's computing device, partly on the user's computing device, as a stand-alone software package, partly on the user's computing device and partly on a remote computing device or entirely on the remote computing device or server. In the latter scenario, the remote computing device may be connected to the user's computing device through any type of network, including a local area network (LAN) or a wide area network (WAN), or the connection may be made to an external computer (for example, through the Internet using an Internet Service Provider).

For every embodiment described herein, to the extent the capability is described for a user to provide input (e.g., by selecting a selectable field on a touchscreen of a reader device, by providing an input through a mechanical button or switch on a reader device, by selecting a field on a display with a mouse, to name a few) then the associated processing circuitry (e.g., that circuitry executing the software described herein) can be described and claimed as monitoring for that user input. This monitoring can include, for example, monitoring for the occurrence of an interrupt or notification from software associated with the hardware (touchscreen, mouse, etc.) accepting that user input. The processing circuitry can also have instructions that permit the processing circuitry to receive and/or read that user input to determine what selection was made by the user. Similarly, for every graphical user interface and/or screen that is displayed, the processing circuitry can be described and claimed as causing the display of (or generating) that graphical user interface or screen and each and every feature therein (icons, text, images, etc.). Although recognized elsewhere herein, it is reiterated that this processing circuitry can be a single processor chip or can be multiple processor chips or portions of processor chips distributed throughout the overall electronic device or devices that are in communication with each other.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An analyte monitoring system for use in episode detection and evaluation, the system comprising:
   a sensor control device comprising a sensor adapted to obtain a measurement of an analyte level of a patient and wireless communication circuitry adapted to communicate the measurement of the analyte level to a reader device; and
   the reader device comprising;
     a display;
     wireless communication circuitry adapted to receive the measurement of the analyte level from the sensor control device;
     processing circuitry communicatively coupled with the wireless communication circuitry, the display, and a non-transitory memory; and
     the non-transitory memory having stored thereon a plurality of first instructions that, when executed by the processing circuitry, cause the processing circuitry to:
       transmit the received measurement of the analyte level to a server;
       in response to receiving an indication of an episode, cause the display of a prompt related to the episode, a text entry field for a customized response, and a picklist of one or more responses that are selectable in response to a determination that an episode has occurred;
       receive a response to the prompt related to the episode regarding a potential cause of the episode;
       implement a modification to the picklist, wherein the modification is at least one of: the addition to the picklist of the customized response that is selectable or the deletion of a response from the picklist; and
       recommend an adjustment to medication therapy based on the determined episode; and
   the server comprising:
     one or more processors coupled with a memory having stored thereon a plurality of second instructions, wherein the second instructions, when executed by the one or more processors, cause the one or more processors to:
       determine whether the measurement of the analyte level indicates that the episode has occurred; and
       transmit the indication of the episode to the reader device; and
   an insulin delivery device configured to administer the recommended adjustment to the medication therapy.

2. The analyte monitoring system of claim 1, wherein the episode is a bedtime episode, wakeup episode, low analyte episode, high analyte episode, rapid analyte rise episode, or rapid analyte fall episode.

3. The analyte monitoring system of claim 1, wherein the prompt related to the episode and the picklist of one or more responses that are selectable is displayed without displaying the analyte level of the patient.

4. The analyte monitoring system of claim 1, wherein the plurality of second instructions, when executed by the one or more processors, further cause the one or more processors to:
 (a) process a plurality of measurements of analyte levels received from the sensor control device over a multi-day period; and
 (b) during the multi-day period, determine whether the plurality of measurements of the analyte levels indicates that one or more episodes have occurred; and
 (c) transmit one or more indications that that one or more episodes have occurred to the reader device,
 wherein the plurality of first instructions, when executed by the processor circuitry, further cause the processing circuitry to:
 (d) cause the display of a prompt related to each detected episode of the one or more episodes and a picklist of one or more responses that are selectable in response to a determination that the one or more episodes have occurred during the multi-day period,
 wherein the plurality of first instructions cause the processing circuitry to perform (d) without causing the display of any analyte level to the subject during the multi-day period.

5. The analyte monitoring system of claim 4, wherein the plurality of first instructions cause the processing circuitry to perform (d) without causing the display of a type of each detected episode to the patient during the multi-day period.

6. The analyte monitoring system of claim 1, wherein the plurality of first instructions cause the processing circuitry to:
 wait until a predetermined event time and then cause the display of a prompt related to the event time and a picklist of one or more responses that are selectable in response to a determination that no episode occurred.

7. The analyte monitoring system of claim 1, wherein the prompt and the one or more responses that are selectable vary depending on a type of the detected episode.

8. The analyte monitoring system of claim 7, wherein the type of the detected episode is a low glucose episode, a high glucose episode, or a rapid rise episode.

9. The analyte monitoring system of claim 1, wherein the second instructions further cause the one or more processors to determine whether the measurement of the analyte level indicates that the episode has occurred during a first time of day period, and wherein the second instructions cause the one or more processors not to determine whether the measurement of the analyte level indicates that the episode has occurred during a second time of day period.

10. The analyte monitoring system of claim 1, wherein the first instructions further cause the processing circuitry to display a count of a number of times that the one or more responses of the picklist was selected.

11. The analyte monitoring system of claim 1, wherein the picklist is a drop-down menu.

12. A method of enabling the reduction of analyte variability for a patient, comprising:
 receiving, with communication circuitry of a reader device, at least one measurement of an analyte level of a patient from a sensor control device;
 transmitting, with the communication circuitry of the reader device, the at least one measurement of the analyte level to a server;
 determining, with processing circuitry of the server, whether the measurement of the analyte level indicates that an episode has occurred;
 transmit, by the server, an indication of the episode to the reader device;
 causing the display, with processing circuitry of the reader device, of a prompt related to the episode and a picklist of one or more responses that are selectable in response to a determination that an episode has occurred;
 implementing, with processing circuitry of the reader device, a modification to the picklist, wherein the modification is at least one of: the addition of a customized response that is selectable to the picklist or the deletion of a response from the picklist:
 receiving, by the communication circuitry of the reader device, a response to the prompt related to the episode regarding a potential cause of the episode;
 implementing an adjustment to medication therapy using an insulin delivery device based on the determined episode.

13. The method of claim 12, wherein the episode is a bedtime episode, wakeup episode, low analyte episode, high analyte episode, rapid analyte rise episode, or rapid analyte fall episode.

14. The method of claim 12, wherein the prompt related to the episode and the picklist of one or more responses that are selectable is displayed without displaying the analyte level of the patient.

15. The method of claim 12, further comprising:
 (a) processing, with the processing circuitry of the server, a plurality of measurements of analyte levels received over a multi-day period;
 (b) during the multi-day period, determining, with the processing circuitry of the server, whether the plurality of measurements of the analyte levels indicates that one or more episodes have occurred;
 (c) transmitting, by the server, one or more indications of the one or more episodes to the reader device; and
 (d) causing, with the processing circuitry of the reader device, the display of a prompt for each detected episode of the one or more episodes and a picklist of one or more responses that are selectable in response to a determination that the one or more episodes have occurred during the multi-day period,
 wherein the processing circuitry of the reader device performs (d) without causing the display of any analyte level to the patient during the multi-day period.

16. The method of claim 15, wherein the processing circuitry of the reader device performs (d) without causing the display of the type of each detected episode to the patient during the multi-day period.

17. The method of claim 12, further comprising:
 waiting until a predetermined event time and then causing, with the processing circuitry of the reader device, the display of a prompt related to the event time and a picklist of one or more responses that are selectable in response to a determination that no episode occurred.

18. The method of claim 12, wherein the question and the one or more responses that are selectable vary depending on a type of the detected episode.

19. The method of claim 18, wherein the type of the detected episode is a low glucose episode, a high glucose episode, or a rapid rise episode.

20. The method of claim 12, wherein the step of determining whether the measurement of the analyte level indicates that an episode has occurred is performed during a first time of day period and not during a second time of day period.

21. The method of claim 12, further comprising the step of causing, with the processing circuitry of the reader device, the display of a count of a number of times that the one or more responses of the picklist was selected.

22. The method of claim 12, wherein the picklist is a drop-down menu.

* * * * *